US007122180B2

(12) United States Patent
Aldovini

(10) Patent No.: US 7,122,180 B2
(45) Date of Patent: Oct. 17, 2006

(54) DNA VECTORS CONTAINING MUTATED HIV PROVIRUSES

(75) Inventor: Anna Aldovini, Weston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 10/000,511

(22) Filed: Oct. 23, 2001

(65) Prior Publication Data

US 2003/0158131 A1 Aug. 21, 2003

Related U.S. Application Data

(60) Provisional application No. 60/242,589, filed on Oct. 23, 2000, provisional application No. 60/253,432, filed on Nov. 28, 2000.

(51) Int. Cl.
*A61K 48/00* (2006.01)
*A61K 31/70* (2006.01)
*C12N 1/00* (2006.01)
*C12N 15/86* (2006.01)
*C12N 5/08* (2006.01)
*C07H 21/04* (2006.01)

(52) U.S. Cl. .................... 424/93.2; 514/44; 435/320.1; 435/456; 435/366; 536/24.1; 536/23.72

(58) Field of Classification Search ................ 514/44; 424/188.1, 198.1; 435/366, 456, 91.4, 91.41; 536/24.1, 23.72
See application file for complete search history.

(56) References Cited

U.S. PATENT DOCUMENTS

| 5,439,809 | A | | 8/1995 | Haynes et al. |
| 5,571,712 | A | | 11/1996 | Haynes et al. |
| 5,795,737 | A | | 8/1998 | Seed et al. |
| 5,861,282 | A | | 1/1999 | Aldovini et al. |
| 5,866,320 | A | | 2/1999 | Rovinski et al. |
| 5,879,925 | A | | 3/1999 | Rovinski et al. |
| 5,889,176 | A | | 3/1999 | Rovinski et al. |
| 5,912,338 | A | | 6/1999 | Rovinski et al. |
| 5,919,458 | A | | 7/1999 | Aldovini et al. |
| 5,955,342 | A | | 9/1999 | Rovinski et al. |
| 5,985,641 | A | | 11/1999 | Haynes et al. |
| 6,025,125 | A | | 2/2000 | Rovinski et al. |
| 6,080,408 | A | * | 6/2000 | Rovinski et al. ......... 424/188.1 |
| 6,121,021 | A | | 9/2000 | Rovinski et al. |
| 6,197,755 | B1 | | 3/2001 | Carrano et al. |
| 2002/0106798 | A1 | * | 8/2002 | Robinson et al. ........... 435/456 |

OTHER PUBLICATIONS

Smith, The continuing HIV vaccine saga: naked emperors alongside fairy godmothers, Medical Immunity, May 6, 2005, vol. 4, No. 6, pp. 1-5.*
Levy, What can be achieved with an HIV vaccine?, The Lancet, Jan. 20, 2001, vol. 9251, No. 357, pp. 223-224).*

Überla, Developing an HIV Vaccine: The Role of Efficacy Studies in Nonhuman Primates, PLoS Medicine, Apr. 2005, vol. 2, Issue 4, e119.*
Amara et al, Control of a Mucosal Challenge and Prevention of AIDS by a Multiprotein DNA.MVA Vaccine, Science, 2001, vol. 292, pp. 69-74.*
Gopalkrishnan et al. Use of the human EF1-a promoter for expression can significantly increase success in establishing stable cell lines with consistent expression, 1999, NAR, vol. 27(24) pp. 4775-4782.*
Andre et al, Increased Immune Response Elicited by DNA Vaccination with a Synthetic gp120 Sequence with Optimized Codon Usage, 1998, JVI, vol. 72(2) pp. 1497-1503.*
Blast 2 sequence results-HIV-1 HXB2 and HIV-1 BH10, downloaded May 26, 2004.*
pBK phagemid vectors, Stratagene catalog, 1995, p. 26.*
Blast sequence HIV-I HXB2 and pol gene sequence, downloaded May 26, 2004.*
Haynes et al, Production of Immunogenic HIV-1 Virus like Particles in Stably Engineered Monkey Cell lines, Aids Research and Human Retroviruses, 1991, vol. 7(1), pp. 17-27.*
Wain-Hobson et al, Nucleotide Sequence of AIDS Virus, LAV, Cell, 1985, vol. 40 pp. 9-17.*
Aldovini et al. "Mutations of RNA and Protein Sequences Involved in Human Immunodeficiency Virus Type 1 Packaging Result in Production of Noninfectious Virus," *Journal of Virology*, vol. 64, No. 5, May 1990, pp. 1920-1926.

(Continued)

*Primary Examiner*—Dave Trong Nguyen
*Assistant Examiner*—Maria Marvich
(74) *Attorney, Agent, or Firm*—Thomas J. Engellenner; Deborah A. Miller; Nutter McClennen & Fish LLP

(57) ABSTRACT

The present invention pertains to mutated, non-infectious HIV viral particles, vectors for production of such particles and vaccines employing such vectors. The non-infectious particles are obtained by introducing a number of inactivating mutations into a native viral genome. These mutations are designed so as to minimize the probability of genetic reversion to an infectious virus, while retaining the basic protein content and immunogenic properties of a wild-type virion. The altered viral genome expresses proteins that can assemble into non-infectious particles which contain immunogenic components of the virus, but which are unable to infect cells. The preferred mutations are introduced in at least one amino acid position of the nucleocapsid (NC) protein in combination with at least one other mutation in an amino acid position of the reverse transcriptase (RT) protein or the In protein. In one embodiment, the mutations to the native HIV genome may also be made in at least one amino acid position of the NC protein, at least one position in the RT protein, and at least one position in the integrase (In) protein. In another embodiment, the mutations to the native HIV genome may be introduced in clusters, where two or more mutations are made in the NC protein, the RT protein, the In protein, or any combinations thereof.

63 Claims, 2 Drawing Sheets

OTHER PUBLICATIONS

Berthoux et al. "Mutations in the N-Terminal Domain of Human Immunodeficiency Virus Type 1 Nucleocapsid Protein Affect Virion Core Structure and Proviral DNA Synthesis," *Journal of Virology*, vol. 71, No. 9, Sep. 1997, pp. 6973-6981.

Campbell et al. "Self-Assembly *In Vitro* of Purified CA-NC Proteins from Rous Sarcoma Viruus and Human Immunodeficiency Virus Type 1," *Journal of Virology*, vol. 69, No. 10, Oct. 1995, pp. 6487-6497.

Cranage et al. "AIDS Vaccine Developments," *Nature*, vol. 355, Feb. 1992, pp. 685-686.

Dannull et al. "Specific Binding of HIV-1 Nucleocapsid Protein to PSI RNA *In Vitro* Requires N-Terminal Zinc Finger and Flanking Basic Amino Acid Residues," *EMBO J*, vol. 13, No. 7, Apr. 1, 1994, pp. 1525-1533.

Deml et al. "Multiple Effects of Codon Usage Optimization on Expression and Immunogenicity of DNA Candidate Vaccines Encoding the Human Immunodeficiency Virus Type 1 Gag Protein," *Journal of Virology*, vol. 75, No. 22, Nov. 2001, pp. 10991-11001.

Druillennec et al. "A Mimic of HIV-1 Nucleocapsid Protein Impairs Reverse Transcription and Displays Antiviral Activity," *Proc. National Academy of Science USA*, vol. 96, Apr. 1999, pp. 4886-4891.

Druillennec et al. "Evidence of Interactions Between the Nucleocapsid Protein NCp7 and the Reverse Transcriptase of HIV-1," *Journal of Biological Chemistry*, vol. 274, No. 16, Apr. 16, 1999, pp. 11283-11288.

Lins et al. "Molecular Dynamics Studies on the HIV-1 Integrase Catalytic Domain," *Biophysical Journal*, vol. 76, Jun. 1999, pp. 2999-3011.

Osterhaus et al. "AIDS Vaccine Developments," *Nature*, vol. 355, Feb. 1992, pp. 684-685.

Ottmann et al. "The Central Globular Domain of the Nucleocapsid Protein of Human Immunodeficiency Virus Type 1 Is Critical for Virion Structure and Infectivity," *Journal of Virology*, vol. 69, No. 3, Mar. 1995, pp. 1778-1784.

Poon et al. "Charged Amino Acid Residues of Human Immunodeficiency Virus Type 1 Nucleocapsid p7 Protein in RNA Packaging and Infectivity," *Journal of Virology*, vol. 70, No. 10, Oct. 1996, pp. 6607-6616.

Poon et al. "Nucleocapsid and Matrix Protein Contributions to Selective Human Immundeficiency Virus Type 1 Genomic RNA Packaging," *Journal of Virology*, vol. 72, No. 3, Mar. 1998, pp. 1983-1993.

Robinson et al. "Neutralizing Antibody-Independent Containment of Immunodeficiency Virus Challeneges by DNA Priming and Recombinant Pox Virus Booster Immunizations," *Nature Medicine*, vol. 5, No. 5, May 1999, pp. 526-534.

Rodgers et al. "The Structure of Unliganded Reverse Transcriptase from the Human Immunodeficiency Virus Type 1," *Proc. National Academy of Science USA*, vol. 92, Feb. 1995, pp. 1222-1226.

Schmalzbauer et al. "Mutations of Basic Amino Acids of NCp7 of Human Immunodeficiency Virus Type 1 Affect RNA Binding in Vitro," *Journal of Virology*, vol. 70, No. 2, Feb. 1996, pp. 771-777.

Schwartz et al. "Distinct Functions and Requirements for the Cys-His Boxes of the Human Immunodeficiency Virus Type 1 Nucleocapsid Protein During RNA Encapsidation and Replication," *Journal of Virology*, vol. 71, No. 12, Dec. 1997, pp. 9295-9305.

Sharma et al. "AZT-Related Mutation Lys70Arg in Reverse Transcriptase of Human Immunodeficiency Virus Type 1 Confers Decrease in Susceptibility to ddATP in *In Vitro* RT Inhibition Assay," *Virology*, vol. 223, Article No. 0488, 1996, pp. 365-369.

Tanchou et al. "Role of the N-Terminal Zinc Finger of Human Immunodeficiency Virus Type 1 Nucleocapsid Protein in Virus Strucure and Replication," *Journal of Virology*, vol. 72, No. 5, May 1998, pp. 4442-4447.

Turner et al. "Structural Biology of HIV," *Journal of Molecular Biology*, vol. 285, Article No. jmbi. 1998.2354, 1999, pp. 1-32.

Winters et al. "Genotypic, Phenotypic, and Modeling Studies of a Deletion in the β3-β4 Region of the Human Immunodeficiency Virus Type 1 Reverse Transcriptase Gene That Is Associated With Resistance to Nucleoside Reverse Transcriptase Inhibitors," *Journal of Virology*, vol. 74, No. 22, Nov. 2000, pp. 10707-10713.

Wiskerchen et al. "Human Immunodeficiency Virus Type 1 Integrase: Effects of Mutations on Viral Ability to Integrate, Direct Viral Gene Expression from Unintegrated Viral DNA Templates, and Sustain Viral Propagation in Primary Cells," *Journal of Virology*, vol. 69, No. 1, Jan. 1995, pp. 376-386.

Zheng et al. "Zinc Folds the N-Terminal Domain of HIV-1 Integrase, Promotes Multimerization, and Enhances Catalytic Activity," *Proc. National Academy of Science USA*, vol. 93, Nov. 1996, pp. 13659-13664.

Egan et al. "Use of Major Histocompatibility Complex Class I/Peptide/β2M Tetramers to Quantitate CD8+ Cytotoxic T Lymphocytes Specific for Dominant and Nondominant Viral Epitopes in Simian-Human Immunodeficiency Virus-Infected Rhesus Monkeys," *Journal of Virology*, vol. 73, No. 7, Jul. 1999, pp. 5466-5472.

Ellison et al. "An Essential Interaction Between Distinct Domains of HIV-1 Integrase Mediates Assembly of the Active Multimer," *Journal of Biological Chemistry*, vol. 270, No. 7, Feb. 17, 1995, pp. 3320-3326.

Graf et al. "Concerted Action of Multiple *cis*-Acting Sequences Is Required for Rev Dependence of Late Human Immunodeficiency Virus Type 1 Gene Expression," *Journal of Virology*, vol. 74, No. 22, Nov. 2000, pp. 10822-10826.

Guo et al. "Human Immunodeficiency Virus Type 1 Nucleocapsid Protein Promotes Efficient Strand Transfer and Specific Viral DNA Synthesis by Inhibiting TAR-Dependent Self-Priming from Minus-Strand Strong-Stop DNA," *Journal of Virology*, vol. 71, No. 7, Jul. 1997, pp. 5178-5188.

Harris et al. "Functional Analysis of Amino Acid Residues Constituting the dNTP Binding Pocket of HIV-1 Reverse Transcriptase," *Journal of Biological Chemistry*, vol. 273, No. 50, Dec. 11, 1998, pp. 33624-33634.

Heinkelein et al. "Rapid and Selective Depletion of CD4 T Lymphocytes and Preferential Loss of Memory Cells on Interaction of Mononuclear Cells With HIV-1 Glycoprotein-Expressing Cells," *Journal of Acquired Immune Deficiency Syndromes and Human Retrovirology*, vol. 16, 1997, pp. 74-82.

Hosie et al. "DNA Vaccination Affords Significant Protection Against Feline Immunodeficiency Virus Infection Without Inducing Detectable Antiviral Antibodies," *Journal of Virology*, vol. 72, No. 9, Sep. 1998, pp. 7310-7319.

Huang et al. "The Role of Nucleocapsid and U5 Stem/A-Rich Loop Sequences in tRNA$_3^{Lys}$ Genomic Placement and Initiation of Reverse Transcription in Human Immunodeficiency Virus Type 1," *Journal of Virology*, vol. 72, No. 5, May 1998, pp. 3907-3915.

Kim et al. "Human Immunodeficiency Virus Reverse Transcriptase," *Journal of Biological Chemistry*, vol. 271, No. 9, Mar. 1, 1996, pp. 4872-4878.

Kim et al. "New Human Immunodeficiency Virus Type 1 Reverse Transcriptase (HIV-1 RT) Mutants with Increased Fidelity of DNA Synthesis," *Journal of Biological Chemistry*, vol. 274, No. 39, Sep. 24, 1999, pp. 27666-27673.

Kotsopoulou et al. "A Rev-Independent Human Immunodeficiency Virus Type 1 (HIV-1)-Based Vector That Exploits a Codon-Optimized HIV-1 *gag-pol* Gene," *Journal of Virology*, vol. 74, No. 10, May 2000, pp. 4839-4852.

Langlois et al. "The Ability of Certain SIV Vaccines to Provoke Reactions Against Normal Cells," *Science*, vol. 255, pp. 292-293. 1992.

Laurent et al. "Functional Characterization of the Human Immunodeficiency Virus Type 1 Genome by Genetic Footprinting," *Journal of Virology*, vol. 74, No. 6, Mar. 2000, pp. 2760-2769.

Leavitt et al. "Human Immunodeficiency Virus Type 1 Integrase Mutants Retain *In Vitro* Integrase Activity Yet Fail to Integrate Viral DNA Efficiently During Infection," *Journal of Virology*, vol. 70, No. 2, Feb. 1996, pp. 721-728.

Le Grand et al. "AIDS Vaccine Developments," *Nature*, vol. 355, Feb. 1992, p. 684.

Lever et al. "Identification of a Sequence Required for Efficient Packaging of Human Immunodeficiency Virus Type 1 RNA Into Virions," *Journal of Virology*, vol. 63, No. 9 Sep 1989, pp. 4085-4087.

Lewis et al. "Uniquely Altered DNA Replication Fidelity Conferred by an Amino Acid Change in the Nucleotide Binding Pocket of Human Immunodeficiency Virus Type 1 Reverse Transcriptase," *Journal of Biological Chemistry*, vol. 274, No. 46, Nov. 12, 1999, pp. 32924-32930.

* cited by examiner

SEQUENCE LISTING

<160> NUMBER OF SEQ ID NOS: 37

<210> SEQ ID NO 1
<211> LENGTH: 9719
<212> TYPE: DNA
<213> ORGANISM: Human immunodeficiency virus

<400> SEQUENCE: 1

```
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180 acaaggaga gaacaccagc ttgttacacc ctgtgagcct gcatggaatg gatgacccgg      240
agagagaagt gttagagtgg aggtttgaca gccgcctagc atttcatcac atggcccgag     300
agctgcatcc ggagtacttc aagaactgct gacatcgagc ttgctacaag ggactttccg     360
ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata aagcttgcct     540
tgagtgcttc aagtagtgtg tgcccgtctg ttgtgtgact ctggtaacta gagatccctc     600
agaccctttt agtcagtgtg gaaaatctct agcagtggcg cccgaacagg gacctgaaag     660
cgaaagggaa accagaggag ctctctcgac gcaggactcg gcttgctgaa gcgcgcacgg     720
caagaggcga ggggcggcga ctggtgagta cgccaaaaat tttgactagc ggaggctaga     780
```

```
aggagagaga tgggtgcgag agcgtcagta ttaagcgggg gagaattaga tcgatgggaa    840
aaaattcggt taaggccagg gggaaagaaa aaatataaat taaaacatat agtatgggca    900
agcagggagc tagaacgatt cgcagttaat cctggcctgt tagaaacatc agaaggctgt    960
agacaaatac tgggacagct acaaccatcc cttcagacag gatcagaaga acttagatca   1020
ttatataata cagtagcaac cctctattgt gtgcatcaaa ggatagagat aaaagacacc   1080
aaggaagctt tagacaagat agaggaagag caaaacaaaa gtaagaaaaa agcacagcaa   1140
gcagcagctg acacaggaca cagcaatcag gtcagccaaa attaccctat agtgcagaac   1200
atccaggggc aaatggtaca tcaggccata tcacctagaa ctttaaatgc atgggtaaaa   1260
gtagtagaag agaaggcttt cagcccagaa gtgatacccc tgttttcagc attatcagaa   1320
ggagccaccc cacaagattt aaacaccatg ctaaacacag tggggggaca tcaagcagcc   1380
atgcaaatgt taaaagagac catcaatgag gaagctgcag aatgggatag agtgcatcca   1440
gtgcatgcag ggcctattgc accaggccag atgagagaac caaggggaag tgacatagca   1500
ggaactacta gtacccttca ggaacaaata ggatggatga caaataatcc acctatccca   1560
gtaggagaaa tttataaaag atggataatc ctgggattaa ataaaatagt aagaatgtat   1620
agccctacca gcattctgga cataagacaa ggaccaaagg aacccttag agactatgta   1680
gaccggttct ataaaactct aagagccgag caagcttcac aggaggtaaa aaattggatg   1740
acagaaacct tgttggtcca aaatgcgaac ccagattgta agactatttt aaaagcattg   1800
ggaccagcgg ctacactaga agaaatgatg acagcatgtc agggagtagg aggacccggc   1860
cataaggcaa gagttttggc tgaagcaatg agccaagtaa caaattcagc taccataatg   1920
atgcagagag caatttttag gaaccaaaga aagattgtta agtgtttcaa ttgtggcaaa   1980
gaagggcaca cagccagaaa ttgcagggcc cctaggaaaa agggctgttg gaaatgtgga   2040
aaggaaggac accaaatgaa agattgtact gagagacagg ctaattttt agggaagatc   2100
tggccttcct acaagggaag gccagggaat tttcttcaga gcagaccaga gccaacagcc   2160
ccaccagaag agagcttcag gtctggggta gagacaacaa ctccccctca gaagcaggag   2220
ccgatagaca aggaactgta tcctttaact tccctcaggt cactctttgg caacgacccc   2280
tcgtcacaat aaagatagg gggcaactaa aggaagctct attagataca ggagcagatg   2340
atacagtatt agaagaaatg agtttgccag gaagatggaa accaaaaatg ataggggaa   2400
ttggaggttt tatcaaagta agacagtatg atcagatact catagaaatc tgtggacata   2460
aagctatagg tacagtatta gtaggaccta cacctgtcaa cataattgga agaaatctgt   2520
tgactcagat tggttgcact ttaaatttc ccattagccc tattgagact gtaccagtaa   2580
aattaaagcc aggaatggat ggcccaaaag ttaaacaatg gccattgaca gaagaaaaaa   2640
taaaagcatt agtagaaatt tgtacagaga tggaaaagga agggaaaatt tcaaaaattg   2700
ggcctgaaaa tccatacaat actccagtat ttgccataaa gaaaaagac agtactaaat   2760
ggagaaaatt agtagatttc agagaactta ataagagaac tcaagacttc tgggaagttc   2820
aattaggaat accacatccc gcagggttaa aaagaaaaa atcagtaaca gtactggatg   2880
tgggtgatgc atatttttca gttcccttag atgaagactt caggaagtat actgcattta   2940
ccatacctag tataaacaat gagacaccag ggattagata tcagtacaat gtgcttccac   3000
agggatggaa aggatcacca gcaatattcc aaagtagcat gacaaaaatc ttagagcctt   3060
ttagaaaaca aaatccagac atagttatct atcaatacat ggatgatttg tatgtaggat   3120
ctgacttaga aatagggcag catagaacaa aaatagagga gctgagacaa catctgttga   3180
```

-continued

```
ggtggggact taccacacca gacaaaaaac atcagaaaga acctccattc ctttggatgg    3240
gttatgaact ccatcctgat aaatggacag tacagcctat agtgctgcca gaaaaagaca    3300
gctggactgt caatgacata cagaagttag tggggaaatt gaattgggca agtcagattt    3360
acccagggat taaagtaagg caattatgta aactccttag aggaaccaaa gcactaacag    3420
aagtaatacc actaacagaa gaagcagagc tagaactggc agaaaacaga gagattctaa    3480
aagaaccagt acatggagtg tattatgacc catcaaaaga cttaatagca gaaatacaga    3540
agcaggggca aggccaatgg acatatcaaa tttatcaaga gccatttaaa aatctgaaaa    3600
caggaaaata tgcaagaatg aggggtgccc acactaatga tgtaaaacaa ttaacagagg    3660
cagtgcaaaa aataaccaca gaaagcatag taatatgggg aaagactcct aaatttaaac    3720
tgcccataca aaaggaaaca tgggaaacat ggtggacaga gtattggcaa gccacctgga    3780
ttcctgagtg ggagtttgtt aatacccctc ccttagtgaa attatggtac cagttagaga    3840
aagaacccat agtaggagca gaaaccttct atgtagatgg ggcagctaac agggagacta    3900
aattaggaaa agcaggatat gttactaata gaggaagaca aaaagttgtc accctaactg    3960
acacaacaaa tcagaagact gagttacaag caatttatct agctttgcag gattcgggat    4020
tagaagtaaa catagtaaca gactcacaat atgcattagg aatcattcaa gcacaaccag    4080
atcaaagtga atcagagtta gtcaatcaaa taatagagca gttaataaaa aaggaaaagg    4140
tctatctggc atgggtacca gcacacaaag gaattggagg aaatgaacaa gtagataaat    4200
tagtcagtgc tggaatcagg aaagtactat ttttagatgg aatagataag gcccaagatg    4260
aacatgagaa atatcacagt aattggagag caatggctag tgattttaac ctgccacctg    4320
tagtagcaaa agaaatagta gccagctgtg ataaatgtca gctaaaagga gaagccatgc    4380
atggacaagt agactgtagt ccaggaatat ggcaactaga ttgtacacat ttagaaggaa    4440
aagttatcct ggtagcagtt catgtagcca gtggatatat agaagcagaa gttattccag    4500
cagaaacagg gcaggaaaca gcatatttc ttttaaaatt agcaggaaga tggccagtaa    4560
aaacaataca tactgacaat ggcagcaatt tcaccggtgc tacggttagg ccgcctgtt    4620 ggtgggcggg aatcaagcag gaatttggaa ttccctacaa tccccaaagt caaggagtag    4680
tagaatctat gaataaagaa ttaagaaaaa ttataggaca ggtaagagat caggctgaac    4740
atcttaagac agcagtacaa atggcagtat tcatccacaa ttttaaaaga aaagggggga    4800
ttggggggta cagtgcaggg gaaagaatag tagacataat agcaacagac atacaaacta    4860
aagaattaca aaaacaaatt acaaaaattc aaaattttcg ggtttattac agggacagca    4920
gaaatccact ttggaaagga ccagcaaagc tcctctggaa aggtgaaggg gcagtagtaa    4980
tacaagataa tagtgacata aaagtagtgc caagaagaaa agcaaagatc attagggatt    5040
atggaaaaca gatggcaggt gatgattgtg tggcaagtag acaggatgag gattagaaca    5100
tggaaaagtt tagtaaaaca ccatatgtat gtttcaggga agctagggga tggttttat    5160 agacatcact atgaaagccc tcatccaaga ataagttcag aagtacacat cccactaggg    5220
gatgctagat tggtaataac aacatattgg ggtctgcata caggagaaag agactggcat    5280
ttgggtcagg gagtctccat agaatggagg aaaaagagat atagcacaca agtagaccct    5340
gaactagcag accaactaat tcatctgtat tactttgact gtttttcaga ctctgctata    5400
agaaaggcct tattaggaca catagttagc cctaggtgtg aatatcaagc aggacataac    5460
aaggtaggat ctctacaata cttggcacta gcagcattaa taacaccaaa aaagataaag    5520
```

```
ccacctttgc ctagtgttac gaaactgaca gaggatagat ggaacaagcc ccagaagacc    5580
aagggccaca gagggagcca cacaatgaat ggacactaga gcttttagag gagcttaaga    5640
atgaagctgt tagacatttt cctaggattt ggctccatgg cttagggcaa catatctatg    5700
aaacttatgg ggatacttgg gcaggagtgg aagccataat aagaattctg caacaactgc    5760
tgtttatcca ttttcagaat tgggtgtcga catagcagaa taggcgttac tcgacagagg    5820
agagcaagaa atggagccag tagatcctag actagagccc tggaagcatc caggaagtca    5880
gcctaaaact gcttgtacca attgctattg taaaagtgt tgctttcatt gccaagtttg    5940
tttcataaca aagccttag gcatctccta tggcaggaag aagcggagac agcgacgaag    6000
agctcatcag aacagtcaga ctcatcaagc ttctctatca aagcagtaag tagtacatgt    6060
aacgcaacct ataccaatag tagcaatagt agcattagta gtagcaataa taatagcaat    6120
agttgtgtgg tccatagtaa tcatagaata taggaaaata ttaagacaaa gaaaaataga    6180
caggttaatt gatagactaa tagaaagagc agaagacagt ggcaatgaga gtgaaggaga    6240
aatatcagca cttgtggaga tgggggtgga gatggggcac catgctcctt gggatgttga    6300
tgatctgtag tgctacagaa aaattgtggg tcacagtcta ttatgggta cctgtgtgga    6360 aggaagcaac caccactcta ttttgtgcat cagatgctaa agcatatgat acagaggtac    6420
ataatgtttg ggccacacat gcctgtgtac ccacagaccc caaccacaa gaagtagtat    6480 tggtaaatgt gacagaaaat tttaacatgt ggaaaatga catggtagaa cagatgcatg    6540
aggatataat cagtttatgg gatcaaagcc taaagccatg tgtaaaatta accccactct    6600
gtgttagttt aaagtgcact gatttgaaga atgatactaa taccaatagt agtagcggga    6660
gaatgataat ggagaaagga gagataaaaa actgctcttt caatatcagc acaagcataa    6720
gaggtaaggt gcagaaagaa tatgcatttt tttataaact tgatataata ccaatagata    6780
atgatactac cagctataag ttgacaagtt gtaacacctc agtcattaca caggcctgtc    6840
caaaggtatc ctttgagcca attcccatac attattgtgc cccggctggt tttgcgattc    6900
taaaatgtaa taataagacg ttcaatggaa caggaccatg tacaaatgtc agcacagtac    6960
aatgtacaca tggaattagg ccagtagtat caactcaact gctgttaaat ggcagtctag    7020
cagaagaaga ggtagtaatt agatctgtca atttcacgga caatgctaaa accataatag    7080
tacagctgaa cacatctgta gaaattaatt gtacaagacc caacaacaat acaagaaaaa    7140
gaatccgtat ccagagagga ccagggagag catttgttac aatagaaaaa ataggaaata    7200
tgagacaagc acattgtaac attagtagag caaaatggaa taacacttta aaacagatag    7260
ctagcaaatt aagagaacaa tttggaaata taaaacaat aatctttaag caatcctcag    7320
gaggggaccc agaaattgta acgcacagtt ttaattgtgg agggaatttt ttctactgta    7380
attcaacaca actgtttaat agtacttggt taatagtac ttggagtact gaagggtcaa    7440
ataacactga aggaagtgac acaatcaccc tcccatgcag aataaaacaa attataaaca    7500
tgtggcagaa agtaggaaaa gcaatgtatg cccctcccat cagtggacaa attagatgtt    7560
catcaaatat tacagggctg ctattaacaa gagatggtgg taatagcaac aatgagtccg    7620
agatcttcag acctggagga ggagatatga gggacaattg gagaagtgaa ttatataaat    7680
ataaagtagt aaaaattgaa ccattaggag tagcacccac caaggcaaag agaagagtgg    7740
tgcagagaga aaaaagagca gtgggaatag gagctttgtt ccttgggttc ttgggagcag    7800
caggaagcac tatgggcgca gcctcaatga cgctgacggt acaggccaga caattattgt    7860
ctggtatagt gcagcagcag aacaatttgc tgagggctat tgaggcgcaa cagcatctgt    7920
```

-continued

```
tgcaactcac agtctggggc atcaagcagc tccaggcaag aatcctggct gtggaaagat    7980
acctaaagga tcaacagctc ctggggattt ggggttgctc tggaaaactc atttgcacca    8040
ctgctgtgcc ttggaatgct agttggagta ataaatctct ggaacagatt tggaatcaca    8100
cgacctggat ggagtgggac agagaaatta acaattacac aagcttaata cactccttaa    8160
ttgaagaatc gcaaaaccag caagaaaaga atgaacaaga attattggaa ttagataaat    8220
gggcaagttt gtggaattgg tttaacataa caaattggct gtggtatata aaattattca    8280
taatgatagt aggaggcttg gtaggtttaa gaatagtttt tgctgtactt tctatagtga    8340
atagagttag gcagggatat tcaccattat cgtttcagac ccacctccca accccgaggg    8400
gacccgacag gcccgaagga atagaagaag aaggtggaga gagagacaga gacagatcca    8460
ttcgattagt gaacggatcc ttggcactta tctgggacga tctgcggagc ctgtgcctct    8520
tcagctacca ccgcttgaga gacttactct tgattgtaac gaggattgtg gaacttctgg    8580
gacgcagggg gtgggaagcc ctcaaatatt ggtggaatct cctacagtat tggagtcagg    8640
aactaaagaa tagtgctgtt agcttgctca atgccacagc catagcagta gctgagggga    8700
cagatagggt tatagaagta gtacaaggag cttgtagagc tattcgccac atacctagaa    8760
gaataagaca gggcttggaa aggatttttgc tataagatgg gtggcaagtg gtcaaaaagt    8820
agtgtgattg gatggcctac tgtaagggaa agaatgagac gagctgagcc agcagcagat    8880
agggtgggag cagcatctcg agacctggaa aaacatggag caatcacaag tagcaataca    8940
gcagctacca atgctgcttg tgcctggcta gaagcacaag aggaggagga ggtgggtttt    9000
ccagtcacac ctcaggtacc tttaagacca atgacttaca aggcagctgt agatcttagc    9060
cacttttttaa aagaaaaggg gggactgaa gggctaattc actcccaaag aagacaagat    9120
atccttgatc tgtggatcta ccacacacaa ggctacttcc ctgattagca gaactacaca    9180
ccagggccag gggtcagata tccactgacc tttggatggt gctacaagct agtaccagtt    9240
gagccagata agatagaaga ggccaataaa ggagagaaca ccagcttgtt acaccctgtg    9300
agcctgcatg gatggatga cccggagaga gaagtgttag agtggaggtt tgacagccgc    9360
ctagcatttc atcacgtggc ccgagagctg catccggagt acttcaagaa ctgctgacat    9420
cgagcttgct acaagggact ttccgctggg gactttccag ggaggcgtgg cctgggcggg    9480
actggggagt ggcgagccct cagatcctgc atataagcag ctgctttttg cctgtactgg    9540
gtctctctgg ttagaccaga tctgagcctg ggagctctct ggctaactag ggaacccact    9600
gcttaagcct caataaagct tgccttgagt gcttcaagta gtgtgtgccc gtctgttgtg    9660
tgactctggt aactagagat ccctcagacc ctttttagtca gtgtggaaaa tctctagca    9719
```

<210> SEQ ID NO 2
<211> LENGTH: 9719
<212> TYPE: DNA
<213> ORGANISM: Human immunodeficiency virus
<220> FEATURE:
<221> NAME/KEY: CDS
<222> LOCATION: (1)..(9717)

<400> SEQUENCE: 2

```
tgg aag ggc taa ttc act ccc aac gaa gac aag ata tcc ttg atc tgt      48
Trp Lys Gly     Phe Thr Pro Asn Glu Asp Lys Ile Ser Leu Ile Cys
  1               5                  10                  15 gga tct acc aca cac aag gct act tcc ctg att agc aga act aca cac      96
Gly Ser Thr Thr His Lys Ala Thr Ser Leu Ile Ser Arg Thr Thr His
             20                  25                  30
```

-continued

```
cag ggc cag gga tca gat atc cac tga cct ttg gat ggt gct aca agc      144
Gln Gly Gln Gly Ser Asp Ile His     Pro Leu Asp Gly Ala Thr Ser
        35              40                  45 tag tac cag ttg agc cag aga agt tag aag aag cca aca aag gag aga      192
    Tyr Gln Leu Ser Gln Arg Ser     Lys Lys Pro Thr Lys Glu Arg
    50                  55                  60 aca cca gct tgt tac acc ctg tga gcc tgc atg gaa tgg atg acc cgg      240
Thr Pro Ala Cys Tyr Thr Leu     Ala Cys Met Glu Trp Met Thr Arg
65              70                  75                  80 aga gag aag tgt tag agt gga ggt ttg aca gcc gcc tag cat ttc atc      288
Arg Glu Lys Cys     Ser Gly Gly Leu Thr Ala Ala     His Phe Ile
                85                  90                  95 aca tgg ccc gag agc tgc atc cgg agt act tca aga act gct gac atc      336
Thr Trp Pro Glu Ser Cys Ile Arg Ser Thr Ser Arg Thr Ala Asp Ile
                100                 105                 110 gag ctt gct aca agg gac ttt ccg ctg ggg act ttc cag gga ggc gtg      384
Glu Leu Ala Thr Arg Asp Phe Pro Leu Gly Thr Phe Gln Gly Gly Val
            115                 120                 125 gcc tgg gcg gga ctg ggg agt ggc gag ccc tca gat cct gca tat aag      432
Ala Trp Ala Gly Leu Gly Ser Gly Glu Pro Ser Asp Pro Ala Tyr Lys
130                 135                 140 cag ctg ctt ttt gcc tgt act ggg tct ctc tgg tta gac cag atc tga      480
Gln Leu Leu Phe Ala Cys Thr Gly Ser Leu Trp Leu Asp Gln Ile
145                 150                 155                 160 gcc tgg gag ctc tct ggc taa cta ggg aac cca ctg ctt aag cct caa      528
Ala Trp Glu Leu Ser Gly     Leu Gly Asn Pro Leu Leu Lys Pro Gln
                165                 170                 175 taa agc ttg cct tga gtg ctt caa gta gtg tgt gcc cgt ctg ttg tgt      576
    Ser Leu Pro     Val Leu Gln Val Val Cys Ala Arg Leu Leu Cys
            180                 185                 190 gac tct ggt aac tag aga tcc ctc aga ccc ttt tag tca gtg tgg aaa      624
Asp Ser Gly Asn     Arg Ser Leu Arg Pro Phe     Ser Val Trp Lys
            195                 200                 205 atc tct agc agt ggc gcc cga aca ggg acc tga aag cga aag gga aac      672
Ile Ser Ser Ser Gly Ala Arg Thr Gly Thr     Lys Arg Lys Gly Asn
210                 215                 220 cag agg agc tct ctc gac gca gga ctc ggc ttg ctg aag cgc gca cgg      720
Gln Arg Ser Ser Leu Asp Ala Gly Leu Gly Leu Leu Lys Arg Ala Arg
225                 230                 235                 240 caa gag gcg agg ggc ggc gac tgg tga gta cgc caa aaa ttt tga cta      768
Gln Glu Ala Arg Gly Gly Asp Trp     Val Arg Gln Lys Phe     Leu
                245                 250                 255 gcg gag gct aga agg aga gag atg ggt gcg aga gcg tca gta tta agc      816
Ala Glu Ala Arg Arg Arg Glu Met Gly Ala Arg Ala Ser Val Leu Ser
                260                 265                 270 ggg gga gaa tta gat cga tgg gaa aaa att cgg tta agg cca ggg gga      864
Gly Gly Glu Leu Asp Arg Trp Glu Lys Ile Arg Leu Arg Pro Gly Gly
            275                 280                 285 aag aaa aaa tat aaa tta aaa cat ata gta tgg gca agc agg gag cta      912
Lys Lys Lys Tyr Lys Leu Lys His Ile Val Trp Ala Ser Arg Glu Leu
290                 295                 300 gaa cga ttc gca gtt aat cct ggc ctg tta gaa aca tca gaa ggc tgt      960
Glu Arg Phe Ala Val Asn Pro Gly Leu Leu Glu Thr Ser Glu Gly Cys
305                 310                 315                 320 aga caa ata ctg gga cag cta caa cca tcc ctt cag aca gga tca gaa     1008
Arg Gln Ile Leu Gly Gln Leu Gln Pro Ser Leu Gln Thr Gly Ser Glu
            325                 330                 335 gaa ctt aga tca tta tat aat aca gta gca acc ctc tat tgt gtg cat     1056
Glu Leu Arg Ser Leu Tyr Asn Thr Val Ala Thr Leu Tyr Cys Val His
```

```
caa agg ata gag ata aaa gac acc aag gaa gct tta gac aag ata gag    1104
Gln Arg Ile Glu Ile Lys Asp Thr Lys Glu Ala Leu Asp Lys Ile Glu
            355                 360                 365 gaa gag caa aac aaa agt aag aaa aaa gca cag caa gca gca gct gac    1152
Glu Glu Gln Asn Lys Ser Lys Lys Lys Ala Gln Gln Ala Ala Ala Asp
        370                 375                 380 aca gga cac agc aat cag gtc agc caa aat tac cct ata gtg cag aac    1200
Thr Gly His Ser Asn Gln Val Ser Gln Asn Tyr Pro Ile Val Gln Asn
385                 390                 395                 400 atc cag ggg caa atg gta cat cag gcc ata tca cct aga act tta aat    1248
Ile Gln Gly Gln Met Val His Gln Ala Ile Ser Pro Arg Thr Leu Asn
                405                 410                 415 gca tgg gta aaa gta gta gaa gag aag gct ttc agc cca gaa gtg ata    1296
Ala Trp Val Lys Val Val Glu Glu Lys Ala Phe Ser Pro Glu Val Ile
            420                 425                 430 ccc atg ttt tca gca tta tca gaa gga gcc acc cca caa gat tta aac    1344
Pro Met Phe Ser Ala Leu Ser Glu Gly Ala Thr Pro Gln Asp Leu Asn
        435                 440                 445 acc atg cta aac aca gtg ggg gga cat caa gca gcc atg caa atg tta    1392
Thr Met Leu Asn Thr Val Gly Gly His Gln Ala Ala Met Gln Met Leu
    450                 455                 460 aaa gag acc atc aat gag gaa gct gca gaa tgg gat aga gtg cat cca    1440
Lys Glu Thr Ile Asn Glu Glu Ala Ala Glu Trp Asp Arg Val His Pro
465                 470                 475                 480 gtg cat gca ggg cct att gca cca ggc cag atg aga gaa cca agg gga    1488
Val His Ala Gly Pro Ile Ala Pro Gly Gln Met Arg Glu Pro Arg Gly
                485                 490                 495 agt gac ata gca gga act act agt acc ctt cag gaa caa ata gga tgg    1536
Ser Asp Ile Ala Gly Thr Thr Ser Thr Leu Gln Glu Gln Ile Gly Trp
            500                 505                 510 atg aca aat aat cca cct atc cca gta gga gaa att tat aaa aga tgg    1584
Met Thr Asn Asn Pro Pro Ile Pro Val Gly Glu Ile Tyr Lys Arg Trp
        515                 520                 525 ata atc ctg gga tta aat aaa ata gta aga atg tat agc cct acc agc    1632
Ile Ile Leu Gly Leu Asn Lys Ile Val Arg Met Tyr Ser Pro Thr Ser
    530                 535                 540 att ctg gac ata aga caa gga cca aag gaa ccc ttt aga gac tat gta    1680
Ile Leu Asp Ile Arg Gln Gly Pro Lys Glu Pro Phe Arg Asp Tyr Val
545                 550                 555                 560 gac cgg ttc tat aaa act cta aga gcc gag caa gct tca cag gag gta    1728
Asp Arg Phe Tyr Lys Thr Leu Arg Ala Glu Gln Ala Ser Gln Glu Val
                565                 570                 575 aaa aat tgg atg aca gaa acc ttg ttg gtc caa aat gcg aac cca gat    1776
Lys Asn Trp Met Thr Glu Thr Leu Leu Val Gln Asn Ala Asn Pro Asp
            580                 585                 590 tgt aag act att tta aaa gca ttg gga cca gcg gct aca cta gaa gaa    1824
Cys Lys Thr Ile Leu Lys Ala Leu Gly Pro Ala Ala Thr Leu Glu Glu
        595                 600                 605 atg atg aca gca tgt cag gga gta gga gga ccc ggc cat aag gca aga    1872
Met Met Thr Ala Cys Gln Gly Val Gly Gly Pro Gly His Lys Ala Arg
    610                 615                 620 gtt ttg gct gaa gca atg agc caa gta aca aat tca gct acc ata atg    1920
Val Leu Ala Glu Ala Met Ser Gln Val Thr Asn Ser Ala Thr Ile Met
625                 630                 635                 640 atg cag aga ggc aat ttt agg aac caa aga aag att gtt aag tgt ttc    1968
Met Gln Arg Gly Asn Phe Arg Asn Gln Arg Lys Ile Val Lys Cys Phe
                645                 650                 655 aat tgt ggc aaa gaa ggg cac aca gcc aga aat tgc agg gcc cct agg    2016
```

```
                Asn Cys Gly Lys Glu Gly His Thr Ala Arg Asn Cys Arg Ala Pro Arg
                                660                 665                 670 aaa aag ggc tgt tgg aaa tgt gga aag gaa gga cac caa atg aaa gat                    2064
Lys Lys Gly Cys Trp Lys Cys Gly Lys Glu Gly His Gln Met Lys Asp
            675                 680                 685 tgt act gag aga cag gct aat ttt tta ggg aag atc tgg cct tcc tac                    2112
Cys Thr Glu Arg Gln Ala Asn Phe Leu Gly Lys Ile Trp Pro Ser Tyr
690                 695                 700 aag gga agg cca ggg aat ttt ctt cag agc aga cca gag cca aca gcc                    2160
Lys Gly Arg Pro Gly Asn Phe Leu Gln Ser Arg Pro Glu Pro Thr Ala
705                 710                 715                 720 cca cca gaa gag agc ttc agg tct ggg gta gag aca aca act ccc cct                    2208
Pro Pro Glu Glu Ser Phe Arg Ser Gly Val Glu Thr Thr Thr Pro Pro
                725                 730                 735 cag aag cag gag ccg ata gac aag gaa ctg tat cct tta act tcc ctc                    2256
Gln Lys Gln Glu Pro Ile Asp Lys Glu Leu Tyr Pro Leu Thr Ser Leu
            740                 745                 750 agg tca ctc ttt ggc aac gac ccc tcg tca caa taa aga tag ggg ggc                    2304
Arg Ser Leu Phe Gly Asn Asp Pro Ser Ser Gln     Arg     Gly Gly
        755                 760                 765 aac taa agg aag ctc tat tag ata cag gag cag atg ata cag tat tag                    2352
Asn     Arg Lys Leu Tyr     Ile Gln Glu Gln Met Ile Gln Tyr
770                 775                 780 aag aaa tga gtt tgc cag gaa gat gga aac caa aaa tga tag ggg gaa                    2400
Lys Lys     Val Cys Gln Glu Asp Gly Asn Gln Lys         Gly Glu
785             790                 795                     800 ttg gag gtt tta tca aag taa gac agt atg atc aga tac tca tag aaa                    2448
Leu Glu Val Leu Ser Lys     Asp Ser Met Ile Arg Tyr Ser     Lys
                805                 810                 815 tct gtg gac ata aag cta tag gta cag tat tag tag gac cta cac ctg                    2496
Ser Val Asp Ile Lys Leu     Val Gln Tyr         Asp Leu His Leu
                820                 825                 830 tca aca taa ttg gaa gaa atc tgt tga ctc aga ttg gtt gca ctt taa                    2544
Ser Thr     Leu Glu Glu Ile Cys     Leu Arg Leu Val Ala Leu
            835                 840                 845 att ttc cca tta gcc cta ttg aga ctg tac cag taa aat taa agc cag                    2592
Ile Phe Pro Leu Ala Leu Leu Arg Leu Tyr Gln     Asn     Ser Gln
850                 855                 860 gaa tgg atg gcc caa aag tta aac aat ggc cat tga cag aag aaa aaa                    2640
Glu Trp Met Ala Gln Lys Leu Asn Asn Gly His     Gln Lys Lys Lys
865                 870                 875                 880 taa aag cat tag tag aaa ttt gta cag aga tgg aaa agg aag gga aaa                    2688
    Lys His         Lys Phe Val Gln Arg Trp Lys Arg Lys Gly Lys
            885                 890                 895 ttt caa aaa ttg ggc ctg aaa atc cat aca ata ctc cag tat ttg cca                    2736
Phe Gln Lys Leu Gly Leu Lys Ile His Thr Ile Leu Gln Tyr Leu Pro
            900                 905                 910 taa aga aaa aag aca gta cta aat gga gaa aat tag tag att tca gag                    2784
    Arg Lys Lys Thr Val Leu Asn Gly Glu Asn         Ile Ser Glu
        915                 920                 925 aac tta ata aga gaa ctc aag act tct ggg aag ttc aat tag gaa tac                    2832
Asn Leu Ile Arg Glu Leu Lys Thr Ser Gly Lys Phe Asn     Glu Tyr
930                 935                 940 cac atc ccg cag ggt taa aaa aga aaa aat cag taa cag tac tgg atg                    2880
His Ile Pro Gln Gly     Lys Arg Lys Asn Gln     Gln Tyr Trp Met
945                 950                 955                 960 tgg gtg atg cat att ttt cag ttc cct tag atg aag act tca gga agt                    2928
Trp Val Met His Ile Phe Gln Phe Pro     Met Lys Thr Ser Gly Ser
                965                 970                 975
```

```
ata ctg cat tta cca tac cta gta taa aca atg aga cac cag gga tta      2976
Ile Leu His Leu Pro Tyr Leu Val     Thr Met Arg His Gln Gly Leu
            980                 985                 990 gat atc agt aca atg tgc ttc cac agg gat gga aag gat cac cag caa      3024
Asp Ile Ser Thr Met Cys Phe His Arg Asp Gly Lys Asp His Gln Gln
            995                1000                1005 tat tcc aaa gta gca tga caa aaa tct tag agc ctt tta gaa aac aaa      3072
Tyr Ser Lys Val Ala     Gln Lys Ser     Ser Leu Leu Glu Asn Lys
        1010                1015                1020 atc cag aca tag tta tct atc aat aca tgg atg att tgt atg tag gat      3120
Ile Gln Thr     Leu Ser Ile Asn Thr Trp Met Ile Cys Met     Asp
1025                1030                1035                1040 ctg act tag aaa tag ggc agc ata gaa caa aaa tag agg agc tga gac      3168
Leu Thr     Lys     Gly Ser Ile Glu Gln Lys     Arg Ser     Asp
                1045                1050                1055 aac atc tgt tga ggt ggg gac tta cca cac cag aca aaa aac atc aga      3216
Asn Ile Cys     Gly Gly Asp Leu Pro His Gln Thr Lys Asn Ile Arg
                1060                1065                1070 aag aac ctc cat tcc ttt gga tgg gtt atg aac tcc atc ctg ata aat      3264
Lys Asn Leu His Ser Phe Gly Trp Val Met Asn Ser Ile Leu Ile Asn
            1075                1080                1085 gga cag tac agc cta tag tgc tgc cag aaa aag aca gct gga ctg tca      3312
Gly Gln Tyr Ser Leu     Cys Cys Gln Lys Lys Thr Ala Gly Leu Ser
            1090                1095                1100 atg aca tac aga agt tag tgg gga aat tga att ggg caa gtc aga ttt      3360
Met Thr Tyr Arg Ser     Trp Gly Asn     Ile Gly Gln Val Arg Phe
1105                1110                1115                1120 acc cag gga tta aag taa ggc aat tat gta aac tcc tta gag gaa cca      3408
Thr Gln Gly Leu Lys     Gly Asn Tyr Val Asn Ser Leu Glu Glu Pro
                1125                1130                1135 aag cac taa cag aag taa tac cac taa cag aag aag cag agc tag aac      3456
Lys His     Gln Lys     Tyr His     Gln Lys Lys Gln Ser     Asn
            1140                1145                1150 tgg cag aaa aca gag aga ttc taa aag aac cag tac atg gag tgt att      3504
Trp Gln Lys Thr Glu Arg Phe     Lys Asn Gln Tyr Met Glu Cys Ile
            1155                1160                1165 atg acc cat caa aag act taa tag cag aaa tac aga agc agg ggc aag      3552
Met Thr His Gln Lys Thr         Gln Lys Tyr Arg Ser Arg Gly Lys
1170                1175                1180 gcc aat gga cat atc aaa ttt atc aag agc cat tta aaa atc tga aaa      3600
Ala Asn Gly His Ile Lys Phe Ile Lys Ser His Leu Lys Ile     Lys
1185                1190                1195                1200 cag gaa aat atg caa gaa tga ggg gtg ccc aca cta atg atg taa aac      3648
Gln Glu Asn Met Gln Glu     Gly Val Pro Thr Leu Met Met     Asn
                1205                1210                1215 aat taa cag agg cag tgc aaa aaa taa cca cag aaa gca tag taa tat      3696
Asn     Gln Arg Gln Cys Lys Lys     Pro Gln Lys Ala     Tyr
            1220                1225                1230 ggg gaa aga ctc cta aat tta aac tgc cca tac aaa agg aaa cat ggg      3744
Gly Glu Arg Leu Leu Asn Leu Asn Cys Pro Tyr Lys Arg Lys His Gly
            1235                1240                1245 aaa cat ggt gga cag agt att ggc aag cca cct gga ttc ctg agt ggg      3792
Lys His Gly Gly Gln Ser Ile Gly Lys Pro Pro Gly Phe Leu Ser Gly
1250                1255                1260 agt ttg tta ata ccc ctc cct tag tga aat tat ggt acc agt tag aga      3840
Ser Leu Leu Ile Pro Leu Pro         Asn Tyr Gly Thr Ser     Arg
1265                1270                1275                1280 aag aac cca tag tag gag cag aaa cct tct atg tag atg ggg cag cta      3888
Lys Asn Pro     Glu Gln Lys Pro Ser Met     Met Gly Gln Leu
            1285                1290                1295
```

-continued

| | | |
|---|---|---|
| aca ggg aga cta aat tag gaa aag cag gat atg tta cta ata gag gaa<br>Thr Gly Arg Leu Asn     Glu Lys Gln Asp Met Leu Leu Ile Glu Glu<br>            1300                1305                    1310 | 3936 |
| gac aaa aag ttg tca ccc taa ctg aca caa caa atc aga aga ctg agt<br>Asp Lys Lys Leu Ser Pro     Leu Thr Gln Gln Ile Arg Arg Leu Ser<br>        1315                1320                1325 | 3984 |
| tac aag caa ttt atc tag ctt tgc agg att cgg gat tag aag taa aca<br>Tyr Lys Gln Phe Ile     Leu Cys Arg Ile Arg Asp     Lys     Thr<br>        1330                1335            1340 | 4032 |
| tag taa cag act cac aat atg cat tag gaa tca ttc aag cac aac cag<br>        Gln Thr His Asn Met His     Glu Ser Phe Lys His Asn Gln<br>1345                1350                1355                1360 | 4080 |
| atc aaa gtg aat cag agt tag tca atc aaa taa tag agc agt taa taa<br>Ile Lys Val Asn Gln Ser     Ser Ile Lys         Ser Ser<br>            1365            1370                1375 | 4128 |
| aaa agg aaa agg tct atc tgg cat ggg tac cag cac aca aag gaa ttg<br>Lys Arg Lys Arg Ser Ile Trp His Gly Tyr Gln His Thr Lys Glu Leu<br>            1380                1385                1390 | 4176 |
| gag gaa atg aac aag tag ata aat tag tca gtg ctg gaa tca gga aag<br>Glu Glu Met Asn Lys     Ile Asn     Ser Val Leu Glu Ser Gly Lys<br>            1395            1400                1405 | 4224 |
| tac tat ttt tag atg gaa tag ata agg ccc aag atg aac atg aga aat<br>Tyr Tyr Phe     Met Glu     Ile Arg Pro Lys Met Asn Met Arg Asn<br>    1410            1415                1420 | 4272 |
| atc aca gta att gga gag caa tgg cta gtg att tta acc tgc cac ctg<br>Ile Thr Val Ile Gly Glu Gln Trp Leu Val Ile Leu Thr Cys His Leu<br>1425                1430                1435                1440 | 4320 |
| tag tag caa aag aaa tag tag cca gct gtg ata aat gtc agc taa aag<br>        Gln Lys Lys         Pro Ala Val Ile Asn Val Ser     Lys<br>            1445                1450                1455 | 4368 |
| gag aag cca tgc atg gac aag tag act gta gtc cag gaa tat ggc aac<br>Glu Lys Pro Cys Met Asp Lys     Thr Val Val Gln Glu Tyr Gly Asn<br>            1460                1465                1470 | 4416 |
| tag att gta cac att tag aag gaa aag tta tcc tgg tag cag ttc atg<br>    Ile Val His Ile     Lys Glu Lys Leu Ser Trp     Gln Phe Met<br>        1475                1480                1485 | 4464 |
| tag cca gtg gat ata tag aag cag aag tta ttc cag cag aaa cag ggc<br>    Pro Val Asp Ile     Lys Gln Lys Leu Phe Gln Gln Lys Gln Gly<br>        1490                1495                1500 | 4512 |
| agg aaa cag cat att ttc ttt taa aat tag cag gaa gat ggc cag taa<br>Arg Lys Gln His Ile Phe Phe     Asn     Gln Glu Asp Gly Gln<br>1505                1510                1515                1520 | 4560 |
| aaa caa tac ata ctg aca atg gca gca att tca ccg gtg cta cgg tta<br>Lys Gln Tyr Ile Leu Thr Met Ala Ala Ile Ser Pro Val Leu Arg Leu<br>            1525                1530                1535 | 4608 |
| ggg ccg cct gtt ggt ggg cgg gaa tca agc agg aat ttg gaa ttc cct<br>Gly Pro Pro Val Gly Gly Arg Glu Ser Ser Arg Asn Leu Glu Phe Pro<br>            1540                1545                1550 | 4656 |
| aca atc ccc aaa gtc aag gag tag tag aat cta tga ata aag aat taa<br>Thr Ile Pro Lys Val Lys Glu     Asn Leu     Ile Lys Asn<br>            1555                1560            1565 | 4704 |
| aga aaa tta tag gac agg taa gag atc agg ctg aac atc tta aga cag<br>Arg Lys Leu     Asp Arg     Glu Ile Arg Leu Asn Ile Leu Arg Gln<br>        1570            1575                1580 | 4752 |
| cag tac aaa tgg cag tat tca tcc aca att tta aaa gaa aag ggg gga<br>Gln Tyr Lys Trp Gln Tyr Ser Ser Thr Ile Leu Lys Glu Lys Gly Gly<br>1585                1590                1595                1600 | 4800 |
| ttg ggg ggt aca gtg cag ggg aaa gaa tag tag aca taa tag caa cag<br>Leu Gly Gly Thr Val Gln Gly Lys Glu         Thr         Gln Gln | 4848 |

-continued

| | | | |
|---|---|---|---|
| aca tac aaa cta aag aat tac aaa aac aaa tta caa aaa ttc aaa att<br>Thr Tyr Lys Leu Lys Asn Tyr Lys Asn Lys Leu Gln Lys Phe Lys Ile<br>                1620                1625                1630 | 4896 |
| ttc ggg ttt att aca ggg aca gca gaa atc cac ttt gga aag gac cag<br>Phe Gly Phe Ile Thr Gly Thr Ala Glu Ile His Phe Gly Lys Asp Gln<br>                1635                1640                1645 | 4944 |
| caa agc tcc tct gga aag gtg aag ggg cag tag taa tac aag ata ata<br>Gln Ser Ser Ser Gly Lys Val Lys Gly Gln         Tyr Lys Ile Ile<br>                1650                1655                1660 | 4992 |
| gtg aca taa aag tag tgc caa gaa gaa aag caa aga tca tta ggg att<br>Val Thr      Lys      Cys Gln Glu Glu Lys Gln Arg Ser Leu Gly Ile<br>1665                1670                1675                1680 | 5040 |
| atg gaa aac aga tgg cag gtg atg att gtg tgg caa gta gac agg atg<br>Met Glu Asn Arg Trp Gln Val Met Ile Val Trp Gln Val Asp Arg Met<br>                1685                1690                1695 | 5088 |
| agg att aga aca tgg aaa agt tta gta aaa cac cat atg tat gtt tca<br>Arg Ile Arg Thr Trp Lys Ser Leu Val Lys His His Met Tyr Val Ser<br>                1700                1705                1710 | 5136 |
| ggg aaa gct agg gga tgg ttt tat aga cat cac tat gaa agc cct cat<br>Gly Lys Ala Arg Gly Trp Phe Tyr Arg His His Tyr Glu Ser Pro His<br>        1715                1720                1725 | 5184 |
| cca aga ata agt tca gaa gta cac atc cca cta ggg gat gct aga ttg<br>Pro Arg Ile Ser Ser Glu Val His Ile Pro Leu Gly Asp Ala Arg Leu<br>        1730                1735                1740 | 5232 |
| gta ata aca aca tat tgg ggt ctg cat aca gga gaa aga gac tgg cat<br>Val Ile Thr Thr Tyr Trp Gly Leu His Thr Gly Glu Arg Asp Trp His<br>1745                1750                1755                1760 | 5280 |
| ttg ggt cag gga gtc tcc ata gaa tgg agg aaa aag aga tat agc aca<br>Leu Gly Gln Gly Val Ser Ile Glu Trp Arg Lys Lys Arg Tyr Ser Thr<br>                1765                1770                1775 | 5328 |
| caa gta gac cct gaa cta gca gac caa cta att cat ctg tat tac ttt<br>Gln Val Asp Pro Glu Leu Ala Asp Gln Leu Ile His Leu Tyr Tyr Phe<br>        1780                1785                1790 | 5376 |
| gac tgt ttt tca gac tct gct ata aga aag gcc tta tta gga cac ata<br>Asp Cys Phe Ser Asp Ser Ala Ile Arg Lys Ala Leu Leu Gly His Ile<br>        1795                1800                1805 | 5424 |
| gtt agc cct agg tgt gaa tat caa gca gga cat aac aag gta gga tct<br>Val Ser Pro Arg Cys Glu Tyr Gln Ala Gly His Asn Lys Val Gly Ser<br>        1810                1815                1820 | 5472 |
| cta caa tac ttg gca cta gca gca tta ata aca cca aaa aag ata aag<br>Leu Gln Tyr Leu Ala Leu Ala Ala Leu Ile Thr Pro Lys Lys Ile Lys<br>1825                1830                1835                1840 | 5520 |
| cca cct ttg cct agt gtt acg aaa ctg aca gag gat aga tgg aac aag<br>Pro Pro Leu Pro Ser Val Thr Lys Leu Thr Glu Asp Arg Trp Asn Lys<br>                1845                1850                1855 | 5568 |
| ccc cag aag acc aag ggc cac aga ggg agc cac aca atg aat gga cac<br>Pro Gln Lys Thr Lys Gly His Arg Gly Ser His Thr Met Asn Gly His<br>        1860                1865                1870 | 5616 |
| tag agc ttt tag agg agc tta aga atg aag ctg tta gac att ttc cta<br>    Ser Phe      Arg Ser Leu Arg Met Lys Leu Leu Asp Ile Phe Leu<br>        1875                1880                1885 | 5664 |
| gga ttt ggc tcc atg gct tag ggc aac ata tct atg aaa ctt atg ggg<br>Gly Phe Gly Ser Met Ala      Gly Asn Ile Ser Met Lys Leu Met Gly<br>        1890                1895                1900 | 5712 |
| ata ctt ggg cag gag tgg aag cca taa taa gaa ttc tgc aac aac tgc<br>Ile Leu Gly Gln Glu Trp Lys Pro            Glu Phe Cys Asn Asn Cys<br>1905                1910                1915                1920 | 5760 |
| tgt tta tcc att ttc aga att ggg tgt cga cat agc aga ata ggc gtt | 5808 |

| | | | |
|---|---|---|---|
| Cys Leu Ser Ile Phe Arg Ile Gly Cys Arg His Ser Arg Ile Gly Val<br>　　　　　　1925　　　　　　　　1930　　　　　　　　1935 | | | |
| act cga cag agg aga gca aga aat gga gcc agt aga tcc tag act aga<br>Thr Arg Gln Arg Arg Ala Arg Asn Gly Ala Ser Arg Ser　　　Thr Arg<br>　　　　　　1940　　　　　　　　1945　　　　　　1950 | | | 5856 |
| gcc ctg gaa gca tcc agg aag tca gcc taa aac tgc ttg tac caa ttg<br>Ala Leu Glu Ala Ser Arg Lys Ser Ala　　　Asn Cys Leu Tyr Gln Leu<br>　　　　　　1955　　　　　　　　1960　　　　　　　　1965 | | | 5904 |
| cta ttg taa aaa gtg ttg ctt tca ttg cca agt ttg ttt cat aac aaa<br>Leu Leu　　　Lys Val Leu Leu Ser Leu Pro Ser Leu Phe His Asn Lys<br>　　　　　1970　　　　　　　　1975　　　　　　　1980 | | | 5952 |
| agc ctt agg cat ctc cta tgg cag gaa gaa gcg gag aca gcg acg aag<br>Ser Leu Arg His Leu Leu Trp Gln Glu Glu Ala Glu Thr Ala Thr Lys<br>1985　　　　　　　　1990　　　　　　　　1995　　　　　　　　2000 | | | 6000 |
| agc tca tca gaa cag tca gac tca tca agc ttc tct atc aaa gca gta<br>Ser Ser Ser Glu Gln Ser Asp Ser Ser Ser Phe Ser Ile Lys Ala Val<br>　　　　　　2005　　　　　　　　2010　　　　　　　　2015 | | | 6048 |
| agt agt aca tgt aac gca acc tat acc aat agt agc aat agt agc att<br>Ser Ser Thr Cys Asn Ala Thr Tyr Thr Asn Ser Ser Asn Ser Ser Ile<br>　　　　　　2020　　　　　　　　2025　　　　　　　　2030 | | | 6096 |
| agt agt agc aat aat aat agc aat agt tgt gtg gtc cat agt aat cat<br>Ser Ser Ser Asn Asn Asn Ser Asn Ser Cys Val Val His Ser Asn His<br>　　　　　　2035　　　　　　　　2040　　　　　　　　2045 | | | 6144 |
| aga ata tag gaa aat att aag aca aag aaa aat aga cag gtt aat tga<br>Arg Ile　　　Glu Asn Ile Lys Thr Lys Lys Asn Arg Gln Val Asn<br>　　　2050　　　　　　　　2055　　　　　　　　2060 | | | 6192 |
| tag act aat aga aag agc aga aga cag tgg caa tga gag tga agg aga<br>　　　Thr Asn Arg Lys Ser Arg Arg Gln Trp Gln　　　Glu　　　Arg Arg<br>2065　　　　　　　　2070　　　　　　　2075　　　　　　　　2080 | | | 6240 |
| aat atc agc act tgt gga gat ggg ggt gga gat ggg gca cca tgc tcc<br>Asn Ile Ser Thr Cys Gly Asp Gly Gly Gly Asp Gly Ala Pro Cys Ser<br>　　　　　　2085　　　　　　　　2090　　　　　　　　2095 | | | 6288 |
| ttg gga tgt tga tga tct gta gtg cta cag aaa aat tgt ggg tca cag<br>Leu Gly Cys　　　　　Ser Val Val Leu Gln Lys Asn Cys Gly Ser Gln<br>　　　　　　2100　　　　　　　　2105　　　　　　　　2110 | | | 6336 |
| tct att atg ggg tac ctg tgt gga agg aag caa cca cca ctc tat ttt<br>Ser Ile Met Gly Tyr Leu Cys Gly Arg Lys Gln Pro Pro Leu Tyr Phe<br>　　　　　　2115　　　　　　　　2120　　　　　　　　2125 | | | 6384 |
| gtg cat cag atg cta aag cat atg ata cag agg tac ata atg ttt ggg<br>Val His Gln Met Leu Lys His Met Ile Gln Arg Tyr Ile Met Phe Gly<br>　　　　　　2130　　　　　　　　2135　　　　　　　　2140 | | | 6432 |
| cca cac atg cct gtg tac cca cag acc cca acc cac aag aag tag tat<br>Pro His Met Pro Val Tyr Pro Gln Thr Pro Thr His Lys Lys　　　Tyr<br>2145　　　　　　　　2150　　　　　　　　2155　　　　　　　　2160 | | | 6480 |
| tgg taa atg tga cag aaa att tta aca tgt gga aaa atg aca tgg tag<br>Trp　　　Met　　　Gln Lys Ile Leu Thr Cys Gly Lys Met Thr Trp<br>　　　　　　2165　　　　　　　　2170　　　　　　　　2175 | | | 6528 |
| aac aga tgc atg agg ata taa tca gtt tat ggg atc aaa gcc taa agc<br>Asn Arg Cys Met Arg Ile　　　Ser Val Tyr Gly Ile Lys Ala　　　Ser<br>　　　　　　2180　　　　　　　　2185　　　　　　　　2190 | | | 6576 |
| cat gtg taa aat taa ccc cac tct gtg tta gtt taa agt gca ctg att<br>His Val　　　Asn　　　Pro His Ser Val Leu Val　　　Ser Ala Leu Ile<br>　　　　　　2195　　　　　　　　2200　　　　　　　　2205 | | | 6624 |
| tga aga atg ata cta ata cca ata gta gta gcg gga gaa tga taa tgg<br>　　　Arg Met Ile Leu Ile Pro Ile Val Val Ala Gly Glu　　　　　Trp<br>　　　2210　　　　　　　　2215　　　　　　　　2220 | | | 6672 |
| aga aag gag aga taa aaa act gct ctt tca ata tca gca caa gca taa<br>Arg Lys Glu Arg　　　Lys Thr Ala Leu Ser Ile Ser Ala Gln Ala<br>2225　　　　　　　　2230　　　　　　　　2235　　　　　　　　2240 | | | 6720 |

-continued

```
gag gta agg tgc aga aag aat atg cat ttt ttt ata aac ttg ata taa      6768
Glu Val Arg Cys Arg Lys Asn Met His Phe Phe Ile Asn Leu Ile
            2245                2250                2255 tac caa tag ata atg ata cta cca gct ata agt tga caa gtt gta aca      6816
Tyr Gln     Ile Met Ile Leu Pro Ala Ile Ser     Gln Val Val Thr
        2260                2265                2270 cct cag tca tta cac agg cct gtc caa agg tat cct ttg agc caa ttc      6864
Pro Gln Ser Leu His Arg Pro Val Gln Arg Tyr Pro Leu Ser Gln Phe
            2275                2280                2285 cca tac att att gtg ccc cgg ctg gtt ttg cga ttc taa aat gta ata      6912
Pro Tyr Ile Ile Val Pro Arg Leu Val Leu Arg Phe     Asn Val Ile
        2290                2295                2300 ata aga cgt tca atg gaa cag gac cat gta caa atg tca gca cag tac      6960
Ile Arg Arg Ser Met Glu Gln Asp His Val Gln Met Ser Ala Gln Tyr
2305                2310                2315                2320 aat gta cac atg gaa tta ggc cag tag tat caa ctc aac tgc tgt taa      7008
Asn Val His Met Glu Leu Gly Gln     Tyr Gln Leu Asn Cys Cys
            2325                2330                2335 atg gca gtc tag cag aag aag agg tag taa tta gat ctg tca att tca      7056
Met Ala Val     Gln Lys Lys Arg         Leu Asp Leu Ser Ile Ser
        2340                2345                2350 cgg aca atg cta aaa cca taa tag tac agc tga aca cat ctg tag aaa      7104
Arg Thr Met Leu Lys Pro     Tyr Ser     Thr His Leu     Lys
            2355                2360                2365 tta att gta caa gac cca aca aca ata caa gaa aaa gaa tcc gta tcc      7152
Leu Ile Val Gln Asp Pro Thr Thr Ile Gln Glu Lys Glu Ser Val Ser
        2370                2375                2380 aga gag gac cag gga gag cat ttg tta caa tag gaa aaa tag gaa ata      7200
Arg Glu Asp Gln Gly Glu His Leu Leu Gln     Glu Lys     Glu Ile
2385                2390                2395                2400 tga gac aag cac att gta aca tta gta gag caa aat gga ata aca ctt      7248
    Asp Lys His Ile Val Thr Leu Val Glu Gln Asn Gly Ile Thr Leu
        2405                2410                2415 taa aac aga tag cta gca aat taa gag aac aat ttg gaa ata ata aaa      7296
    Asn Arg     Leu Ala Asn     Glu Asn Asn Leu Glu Ile Ile Lys
            2420                2425                2430 caa taa tct tta agc aat cct cag gag ggg acc cag aaa ttg taa cgc      7344
Gln     Ser Leu Ser Asn Pro Gln Glu Gly Thr Gln Lys Leu     Arg
            2435                2440                2445 aca gtt tta att gtg gag ggg aat ttt tct act gta att caa cac aac      7392
Thr Val Leu Ile Val Glu Gly Asn Phe Ser Thr Val Ile Gln His Asn
        2450                2455                2460 tgt tta ata gta ctt ggt tta ata gta ctt gga gta ctg aag ggt caa      7440
Cys Leu Ile Val Leu Gly Leu Ile Val Leu Gly Val Leu Lys Gly Gln
2465                2470                2475                2480 ata aca ctg aag gaa gtg aca caa tca ccc tcc cat gca gaa taa aac      7488
Ile Thr Leu Lys Glu Val Thr Gln Ser Pro Ser His Ala Glu     Asn
            2485                2490                2495 aaa tta taa aca tgt ggc aga aag tag gaa aag caa tgt atg ccc ctc      7536
Lys Leu     Thr Cys Gly Arg Lys     Glu Lys Gln Cys Met Pro Leu
        2500                2505                2510 cca tca gtg gac aaa tta gat gtt cat caa ata tta cag ggc tgc tat      7584
Pro Ser Val Asp Lys Leu Asp Val His Gln Ile Leu Gln Gly Cys Tyr
        2515                2520                2525 taa caa gag atg gtg gta ata gca aca atg agt ccg aga tct tca gac      7632
    Gln Glu Met Val Val Ile Ala Thr Met Ser Pro Arg Ser Ser Asp
        2530                2535                2540 ctg gag gag gag ata tga ggg aca att gga gaa gtg aat tat ata aat      7680
Leu Glu Glu Glu Ile     Gly Thr Ile Gly Glu Val Asn Tyr Ile Asn
2545                2550                2555                2560
```

-continued

| | | |
|---|---|---|
| ata aag tag taa aaa ttg aac cat tag gag tag cac cca cca agg caa<br>Ile Lys        Lys Leu Asn His        Glu        His Pro Pro Arg Gln<br>          2565                                  2570                           2575 | 7728 |
| aga gaa gag tgg tgc aga gag aaa aaa gag cag tgg gaa tag gag ctt<br>Arg Glu Glu Trp Cys Arg Glu Lys Lys Glu Gln Trp Glu        Glu Leu<br>          2580                               2585                        2590 | 7776 |
| tgt tcc ttg ggt tct tgg gag cag cag gaa gca cta tgg gcg cag cct<br>Cys Ser Leu Gly Ser Trp Glu Gln Gln Glu Ala Leu Trp Ala Gln Pro<br>          2595                             2600                       2605 | 7824 |
| caa tga cgc tga cgg tac agg cca gac aat tat tgt ctg gta tag tgc<br>Gln     Arg     Arg Tyr Arg Pro Asp Asn Tyr Cys Leu Val     Cys<br>        2610                       2615                       2620 | 7872 |
| agc agc aga aca att tgc tga ggg cta ttg agg cgc aac agc atc tgt<br>Ser Ser Arg Thr Ile Cys     Gly Leu Leu Arg Arg Asn Ser Ile Cys<br>2625                  2630                    2635                  2640 | 7920 |
| tgc aac tca cag tct ggg gca tca agc agc tcc agg caa gaa tcc tgg<br>Cys Asn Ser Gln Ser Gly Ala Ser Ser Ser Arg Gln Glu Ser Trp<br>               2645                             2650                    2655 | 7968 |
| ctg tgg aaa gat acc taa agg atc aac agc tcc tgg gga ttt ggg gtt<br>Leu Trp Lys Asp Thr     Arg Ile Asn Ser Ser Trp Gly Phe Gly Val<br>              2660                         2665                    2670 | 8016 |
| gct ctg gaa aac tca ttt gca cca ctg ctg tgc ctt gga atg cta gtt<br>Ala Leu Glu Asn Ser Phe Ala Pro Leu Leu Cys Leu Gly Met Leu Val<br>            2675                           2680                      2685 | 8064 |
| gga gta ata aat ctc tgg aac aga ttt gga atc aca cga cct gga tgg<br>Gly Val Ile Asn Leu Trp Asn Arg Phe Gly Ile Thr Arg Pro Gly Trp<br>          2690                         2695                      2700 | 8112 |
| agt ggg aca gag aaa tta aca att aca caa gct taa tac act cct taa<br>Ser Gly Thr Glu Lys Leu Thr Ile Thr Gln Ala     Tyr Thr Pro<br>2705                  2710                    2715                    2720 | 8160 |
| ttg aag aat cgc aaa acc agc aag aaa aga atg aac aag aat tat tgg<br>Leu Lys Asn Arg Lys Thr Ser Lys Lys Arg Met Asn Lys Asn Tyr Trp<br>                 2725                         2730                    2735 | 8208 |
| aat tag ata aat ggg caa gtt tgt gga att ggt tta aca taa caa att<br>Asn     Ile Asn Gly Gln Val Cys Gly Ile Gly Leu Thr     Gln Ile<br>                    2740                        2745                    2750 | 8256 |
| ggc tgt ggt ata taa aat tat tca taa tga tag tag gag gct tgg tag<br>Gly Cys Gly Ile     Asn Tyr Ser                         Glu Ala Trp<br>        2755                       2760                               2765 | 8304 |
| gtt taa gaa tag ttt ttg ctg tac ttt cta tag tga ata gag tta ggc<br>Val     Glu     Phe Leu Leu Tyr Phe Leu          Ile Glu Leu Gly<br>        2770                       2775                    2780 | 8352 |
| agg gat att cac cat tat cgt ttc aga ccc acc tcc caa ccc cga ggg<br>Arg Asp Ile His His Tyr Arg Phe Arg Pro Thr Ser Gln Pro Arg Gly<br>2785                  2790                    2795                    2800 | 8400 |
| gac ccg aca ggc ccg aag gaa tag aag aag aag gtg gag aga gag aca<br>Asp Pro Thr Gly Pro Lys Glu     Lys Lys Lys Val Glu Arg Glu Thr<br>                    2805                         2810                       2815 | 8448 |
| gag aca gat cca ttc gat tag tga acg gat cct tgg cac tta tct ggg<br>Glu Thr Asp Pro Phe Asp          Thr Asp Pro Trp His Leu Ser Gly<br>              2820                          2825                    2830 | 8496 |
| acg atc tgc gga gcc tgt gcc tct tca gct acc acc gct tga gag act<br>Thr Ile Cys Gly Ala Cys Ala Ser Ser Ala Thr Thr Ala     Glu Thr<br>            2835                           2840                      2845 | 8544 |
| tac tct tga ttg taa cga gga ttg tgg aac ttc tgg gac gca ggg ggt<br>Tyr Ser     Leu         Arg Gly Leu Trp Asn Phe Trp Asp Ala Gly Gly<br>          2850                          2855                    2860 | 8592 |
| ggg aag ccc tca aat att ggt gga atc tcc tac agt att gga gtc agg<br>Gly Lys Pro Ser Asn Ile Gly Gly Ile Ser Tyr Ser Ile Gly Val Arg | 8640 |

-continued

| | |
|---|---|
| aac taa aga ata gtg ctg tta gct tgc tca atg cca cag cca tag cag<br>Asn      Arg Ile Val Leu Leu Ala Cys Ser Met Pro Gln Pro      Gln<br>                        2885                            2890                         2895 | 8688 |
| tag ctg agg gga cag ata ggg tta tag aag tag tac aag gag ctt gta<br>      Leu Arg Gly Gln Ile Gly Leu      Lys      Tyr Lys Glu Leu Val<br>                      2900                        2905                          2910 | 8736 |
| gag cta ttc gcc aca tac cta gaa gaa taa gac agg gct tgg aaa gga<br>Glu Leu Phe Ala Thr Tyr Leu Glu Glu      Asp Arg Ala Trp Lys Gly<br>            2915                        2920                        2925 | 8784 |
| ttt tgc tat aag atg ggt ggc aag tgg tca aaa agt agt gtg att gga<br>Phe Cys Tyr Lys Met Gly Gly Lys Trp Ser Lys Ser Ser Val Ile Gly<br>            2930                        2935                        2940 | 8832 |
| tgg cct act gta agg gaa aga atg aga cga gct gag cca gca gca gat<br>Trp Pro Thr Val Arg Glu Arg Met Arg Arg Ala Glu Pro Ala Ala Asp<br>2945                        2950                        2955                        2960 | 8880 |
| agg gtg gga gca gca tct cga gac ctg gaa aaa cat gga gca atc aca<br>Arg Val Gly Ala Ala Ser Arg Asp Leu Glu Lys His Gly Ala Ile Thr<br>                    2965                        2970                        2975 | 8928 |
| agt agc aat aca gca gct acc aat gct gct tgt gcc tgg cta gaa gca<br>Ser Ser Asn Thr Ala Ala Thr Asn Ala Ala Cys Ala Trp Leu Glu Ala<br>            2980                        2985                        2990 | 8976 |
| caa gag gag gag gag gtg ggt ttt cca gtc aca cct cag gta cct tta<br>Gln Glu Glu Glu Glu Val Gly Phe Pro Val Thr Pro Gln Val Pro Leu<br>                2995                        3000                        3005 | 9024 |
| aga cca atg act tac aag gca gct gta gat ctt agc cac ttt tta aaa<br>Arg Pro Met Thr Tyr Lys Ala Ala Val Asp Leu Ser His Phe Leu Lys<br>            3010                        3015                        3020 | 9072 |
| gaa aag ggg gga ctg gaa ggg cta att cac tcc caa aga aga caa gat<br>Glu Lys Gly Gly Leu Glu Gly Leu Ile His Ser Gln Arg Arg Gln Asp<br>3025                        3030                        3035                        3040 | 9120 |
| atc ctt gat ctg tgg atc tac cac aca caa ggc tac ttc cct gat tag<br>Ile Leu Asp Leu Trp Ile Tyr His Thr Gln Gly Tyr Phe Pro Asp<br>                    3045                        3050                        3055 | 9168 |
| cag aac tac aca cca ggg cca ggg gtc aga tat cca ctg acc ttt gga<br>Gln Asn Tyr Thr Pro Gly Pro Gly Val Arg Tyr Pro Leu Thr Phe Gly<br>            3060                        3065                        3070 | 9216 |
| tgg tgc tac aag cta gta cca gtt gag cca gat aag ata gaa gag gcc<br>Trp Cys Tyr Lys Leu Val Pro Val Glu Pro Asp Lys Ile Glu Glu Ala<br>            3075                        3080                        3085 | 9264 |
| aat aaa gga gag aac acc agc ttg tta cac cct gtg agc ctg cat ggg<br>Asn Lys Gly Glu Asn Thr Ser Leu Leu His Pro Val Ser Leu His Gly<br>            3090                        3095                        3100 | 9312 |
| atg gat gac ccg gag aga gaa gtg tta gag tgg agg ttt gac agc cgc<br>Met Asp Asp Pro Glu Arg Glu Val Leu Glu Trp Arg Phe Asp Ser Arg<br>3105                        3110                        3115                        3120 | 9360 |
| cta gca ttt cat cac gtg gcc cga gag ctg cat ccg gag tac ttc aag<br>Leu Ala Phe His His Val Ala Arg Glu Leu His Pro Glu Tyr Phe Lys<br>            3125                        3130                        3135 | 9408 |
| aac tgc tga cat cga gct tgc tac aag gga ctt tcc gct ggg gac ttt<br>Asn Cys      His Arg Ala Cys Tyr Lys Gly Leu Ser Ala Gly Asp Phe<br>                      3140                        3145                        3150 | 9456 |
| cca ggg agg cgt ggc ctg ggc ggg act ggg gag tgg cga gcc ctc aga<br>Pro Gly Arg Arg Gly Leu Gly Gly Thr Gly Glu Trp Arg Ala Leu Arg<br>            3155                        3160                        3165 | 9504 |
| tcc tgc ata taa gca gct gct ttt gcc tgt act ggg tct ctg gtt<br>Ser Cys Ile      Ala Ala Ala Phe Cys Leu Tyr Trp Val Ser Leu Val<br>            3170                        3175                        3180 | 9552 |
| aga cca gat ctg agc ctg gga gct ctc tgg cta act agg gaa ccc act | 9600 |

```
Arg Pro Asp Leu Ser Leu Gly Ala Leu Trp Leu Thr Arg Glu Pro Thr
3185                3190                3195                3200 gct taa gcc tca ata aag ctt gcc ttg agt gct tca agt agt gtg tgc   9648
Ala     Ala Ser Ile Lys Leu Ala Leu Ser Ala Ser Ser Ser Val Cys
                3205                3210                3215 ccg tct gtt gtg tga ctc tgg taa cta gag atc cct cag acc ctt tta   9696
Pro Ser Val Val     Leu Trp     Leu Glu Ile Pro Gln Thr Leu Leu
            3220                3225                3230 gtc agt gtg gaa aat ctc tag ca                                    9719
Val Ser Val Glu Asn Leu
        3235

<210> SEQ ID NO 3
<211> LENGTH: 1674
<212> TYPE: DNA
<213> ORGANISM: Human immunodeficiency virus

<400> SEQUENCE: 3
cccattagcc ctattgagac tgtaccagta aaattaaagc caggaatgga tggcccaaaa     60
gttaaacaat ggccattgac agaagaaaaa ataaaagcat tagtagaaat ttgtacagag    120
atggaaaagg aagggaaaat ttcaaaaatt gggcctgaaa atccatacaa tactccagta    180
tttgccataa agaaaaaaga cagtactaaa tggagaaaat tagtagattt cagagaactt    240
aataagagaa ctcaagactt ctgggaagtt caattaggaa taccacatcc cgcagggtta    300
aaaaagaaaa aatcagtaac agtactggat gtgggtgatg catatttttc agttccctta    360
gatgaagact tcaggaagta tactgcattt accataccta gtataaacaa tgagacacca    420
gggattagat atcagtacaa tgtgcttcca cagggatgga aaggatcacc agcaatattc    480
caaagtagca tgacaaaaat cttagagcct tttagaaaac aaaatccaga catagttatc    540
tatcaataca tggatgattt gtatgtagga tctgacttag aaatagggca gcatagaaca    600
aaaatagagg agctgagaca acatctgttg aggtggggac ttaccacacc agacaaaaaa    660
catcagaaag aacctccatt cctttggatg ggttatgaac tccatcctga taaatggaca    720
gtacagccta tagtgctgcc agaaaaagac agctggactg tcaatgacat acagaagtta    780
gtggggaaat tgaattgggc aagtcagatt tacccaggga ttaaagtaag gcaattatgt    840
aaactcctta gaggaaccaa agcactaaca gaagtaatac cactaacaga agaagcagag    900
ctagaactgg cagaaaacag agagattcta aaagaaccag tacatggagt gtattatgac    960
ccatcaaaag acttaatagc agaaatacag aagcaggggc aaggccaatg gacatatcaa   1020
atttatcaag agccatttaa aaatctgaaa acaggaaaat atgcaagaat gaggggtgcc   1080
cacactaatg atgtaaaaca attaacagag gcagtgcaaa aaataaccac agaaagcata   1140
gtaatatggg gaaagactcc taaatttaaa ctgcccatac aaaaggaaac atgggaaaca   1200
tggtggacag agtattggca agccacctgg attcctgagt gggagtttgt taatacccct   1260
cccttagtga aattatggta ccagttagag aaagaaccca tagtaggagc agaaaccttc   1320
tatgtagatg gggcagctaa cagggagact aaattaggaa agcaggata tgttactaat   1380 agaggaagac aaaaagttgt caccctaact gacacaacaa atcagaagac tgagttacaa   1440
gcaatttatc tagctttgca ggattcggga ttagaagtaa acatagtaac agactcacaa   1500
tatgcattag gaatcattca agcacaacca gatcaaagtg aatcagagtt agtcaatcaa   1560
ataatagagc agttaataaa aaaggaaaag gtctatctgg catgggtacc agcacacaaa   1620
ggaattggag gaaatgaaca agtagataaa ttagtcagtg ctggaatcag gaaa         1674
```

```
<210> SEQ ID NO 4
<211> LENGTH: 1674
<212> TYPE: DNA
<213> ORGANISM: Human immunodeficiency virus
<220> FEATURE:
<221> NAME/KEY: CDS
<222> LOCATION: (1)..(1674)

<400> SEQUENCE: 4 ccc att agc cct att gag act gta cca gta aaa tta aag cca gga atg        48
Pro Ile Ser Pro Ile Glu Thr Val Pro Val Lys Leu Lys Pro Gly Met
  1               5                  10                  15 gat ggc cca aaa gtt aaa caa tgg cca ttg aca gaa gaa aaa ata aaa        96
Asp Gly Pro Lys Val Lys Gln Trp Pro Leu Thr Glu Glu Lys Ile Lys
             20                  25                  30 gca tta gta gaa att tgt aca gag atg gaa aag gaa ggg aaa att tca       144
Ala Leu Val Glu Ile Cys Thr Glu Met Glu Lys Glu Gly Lys Ile Ser
         35                  40                  45 aaa att ggg cct gaa aat cca tac aat act cca gta ttt gcc ata aag       192
Lys Ile Gly Pro Glu Asn Pro Tyr Asn Thr Pro Val Phe Ala Ile Lys
     50                  55                  60 aaa aaa gac agt act aaa tgg aga aaa tta gta gat ttc aga gaa ctt       240
Lys Lys Asp Ser Thr Lys Trp Arg Lys Leu Val Asp Phe Arg Glu Leu
 65                  70                  75                  80 aat aag aga act caa gac ttc tgg gaa gtt caa tta gga ata cca cat       288
Asn Lys Arg Thr Gln Asp Phe Trp Glu Val Gln Leu Gly Ile Pro His
                 85                  90                  95 ccc gca ggg tta aaa aag aaa aaa tca gta aca gta ctg gat gtg ggt       336
Pro Ala Gly Leu Lys Lys Lys Lys Ser Val Thr Val Leu Asp Val Gly
            100                 105                 110 gat gca tat ttt tca gtt ccc tta gat gaa gac ttc agg aag tat act       384
Asp Ala Tyr Phe Ser Val Pro Leu Asp Glu Asp Phe Arg Lys Tyr Thr
        115                 120                 125 gca ttt acc ata cct agt ata aac aat gag aca cca ggg att aga tat       432
Ala Phe Thr Ile Pro Ser Ile Asn Asn Glu Thr Pro Gly Ile Arg Tyr
    130                 135                 140 cag tac aat gtg ctt cca cag gga tgg aaa gga tca cca gca ata ttc       480
Gln Tyr Asn Val Leu Pro Gln Gly Trp Lys Gly Ser Pro Ala Ile Phe
145                 150                 155                 160 caa agt agc atg aca aaa atc tta gag cct ttt aga aaa caa aat cca       528
Gln Ser Ser Met Thr Lys Ile Leu Glu Pro Phe Arg Lys Gln Asn Pro
                165                 170                 175 gac ata gtt atc tat caa tac atg gat gat ttg tat gta gga tct gac       576
Asp Ile Val Ile Tyr Gln Tyr Met Asp Asp Leu Tyr Val Gly Ser Asp
            180                 185                 190 tta gaa ata ggg cag cat aga aca aaa ata gag gag ctg aga caa cat       624
Leu Glu Ile Gly Gln His Arg Thr Lys Ile Glu Glu Leu Arg Gln His
        195                 200                 205 ctg ttg agg tgg gga ctt acc aca cca gac aaa aaa cat cag aaa gaa       672
Leu Leu Arg Trp Gly Leu Thr Thr Pro Asp Lys Lys His Gln Lys Glu
    210                 215                 220 cct cca ttc ctt tgg atg ggt tat gaa ctc cat cct gat aaa tgg aca       720
Pro Pro Phe Leu Trp Met Gly Tyr Glu Leu His Pro Asp Lys Trp Thr
225                 230                 235                 240 gta cag cct ata gtg ctg cca gaa aaa gac agc tgg act gtc aat gac       768
Val Gln Pro Ile Val Leu Pro Glu Lys Asp Ser Trp Thr Val Asn Asp
                245                 250                 255 ata cag aag tta gtg ggg aaa ttg aat tgg gca agt cag att tac cca       816
Ile Gln Lys Leu Val Gly Lys Leu Asn Trp Ala Ser Gln Ile Tyr Pro
            260                 265                 270
```

| | | |
|---|---|---|
| ggg att aaa gta agg caa tta tgt aaa ctc ctt aga gga acc aaa gca<br>Gly Ile Lys Val Arg Gln Leu Cys Lys Leu Leu Arg Gly Thr Lys Ala<br>275 280 285 | | 864 |
| cta aca gaa gta ata cca cta aca gaa gaa gca gag cta gaa ctg gca<br>Leu Thr Glu Val Ile Pro Leu Thr Glu Glu Ala Glu Leu Glu Leu Ala<br>290 295 300 | | 912 |
| gaa aac aga gag att cta aaa gaa cca gta cat gga gtg tat tat gac<br>Glu Asn Arg Glu Ile Leu Lys Glu Pro Val His Gly Val Tyr Tyr Asp<br>305 310 315 320 | | 960 |
| cca tca aaa gac tta ata gca gaa ata cag aag cag ggg caa ggc caa<br>Pro Ser Lys Asp Leu Ile Ala Glu Ile Gln Lys Gln Gly Gln Gly Gln<br>325 330 335 | | 1008 |
| tgg aca tat caa att tat caa gag cca ttt aaa aat ctg aaa aca gga<br>Trp Thr Tyr Gln Ile Tyr Gln Glu Pro Phe Lys Asn Leu Lys Thr Gly<br>340 345 350 | | 1056 |
| aaa tat gca aga atg agg ggt gcc cac act aat gat gta aaa caa tta<br>Lys Tyr Ala Arg Met Arg Gly Ala His Thr Asn Asp Val Lys Gln Leu<br>355 360 365 | | 1104 |
| aca gag gca gtg caa aaa ata acc aca gaa agc ata gta ata tgg gga<br>Thr Glu Ala Val Gln Lys Ile Thr Thr Glu Ser Ile Val Ile Trp Gly<br>370 375 380 | | 1152 |
| aag act cct aaa ttt aaa ctg ccc ata caa aag gaa aca tgg gaa aca<br>Lys Thr Pro Lys Phe Lys Leu Pro Ile Gln Lys Glu Thr Trp Glu Thr<br>385 390 395 400 | | 1200 |
| tgg tgg aca gag tat tgg caa gcc acc tgg att cct gag tgg gag ttt<br>Trp Trp Thr Glu Tyr Trp Gln Ala Thr Trp Ile Pro Glu Trp Glu Phe<br>405 410 415 | | 1248 |
| gtt aat acc cct ccc tta gtg aaa tta tgg tac cag tta gag aaa gaa<br>Val Asn Thr Pro Pro Leu Val Lys Leu Trp Tyr Gln Leu Glu Lys Glu<br>420 425 430 | | 1296 |
| ccc ata gta gga gca gaa acc ttc tat gta gat ggg gca gct aac agg<br>Pro Ile Val Gly Ala Glu Thr Phe Tyr Val Asp Gly Ala Ala Asn Arg<br>435 440 445 | | 1344 |
| gag act aaa tta gga aaa gca gga tat gtt act aat aga gga aga caa<br>Glu Thr Lys Leu Gly Lys Ala Gly Tyr Val Thr Asn Arg Gly Arg Gln<br>450 455 460 | | 1392 |
| aaa gtt gtc acc cta act gac aca aca aat cag aag act gag tta caa<br>Lys Val Val Thr Leu Thr Asp Thr Thr Asn Gln Lys Thr Glu Leu Gln<br>465 470 475 480 | | 1440 |
| gca att tat cta gct ttg cag gat tcg gga tta gaa gta aac ata gta<br>Ala Ile Tyr Leu Ala Leu Gln Asp Ser Gly Leu Glu Val Asn Ile Val<br>485 490 495 | | 1488 |
| aca gac tca caa tat gca tta gga atc att caa gca caa cca gat caa<br>Thr Asp Ser Gln Tyr Ala Leu Gly Ile Ile Gln Ala Gln Pro Asp Gln<br>500 505 510 | | 1536 |
| agt gaa tca gag tta gtc aat caa ata ata gag cag tta ata aaa aag<br>Ser Glu Ser Glu Leu Val Asn Gln Ile Ile Glu Gln Leu Ile Lys Lys<br>515 520 525 | | 1584 |
| gaa aag gtc tat ctg gca tgg gta cca gca cac aaa gga att gga gga<br>Glu Lys Val Tyr Leu Ala Trp Val Pro Ala His Lys Gly Ile Gly Gly<br>530 535 540 | | 1632 |
| aat gaa caa gta gat aaa tta gtc agt gct gga atc agg aaa<br>Asn Glu Gln Val Asp Lys Leu Val Ser Ala Gly Ile Arg Lys<br>545 550 555 | | 1674 |

<210> SEQ ID NO 5
<211> LENGTH: 870
<212> TYPE: DNA
<213> ORGANISM: Human immunodeficiency virus

<400> SEQUENCE: 5

```
gtactatttt tagatggaat agataaggcc caagatgaac atgagaaata tcacagtaat    60
tggagagcaa tggctagtga ttttaacctg ccacctgtag tagcaaaaga aatagtagcc   120
agctgtgata aatgtcagct aaaaggagaa gccatgcatg gacaagtaga ctgtagtcca   180
ggaatatggc aactagattg tacacattta gaaggaaaag ttatcctggt agcagttcat   240
gtagccagtg gatatataga agcagaagtt attccagcag aaacagggca ggaaacagca   300
tattttcttt taaaattagc aggaagatgg ccagtaaaaa caatacatac tgacaatggc   360
agcaatttca ccggtgctac ggttagggcc gcctgttggt gggcgggaat caagcaggaa   420
tttggaattc cctacaatcc ccaaagtcaa ggagtagtag aatctatgaa taaagaatta   480
aagaaaatta taggacaggt aagagatcag gctgaacatc ttaagacagc agtacaaatg   540
gcagtattca tccacaattt taaaagaaaa ggggggattg ggggtacag tgcagggaa   600 agaatagtag acataatagc aacagacata caaactaaag aattacaaaa acaaattaca   660
aaaattcaaa attttcgggt ttattacagg gacagcagaa atccactttg gaaaggacca   720
gcaaagctcc tctggaaagg tgaagggca gtagtaatac aagataatag tgacataaaa   780
gtagtgccaa gaagaaaagc aaagatcatt agggattatg gaaaacagat ggcaggtgat   840
gattgtgtgg caagtagaca ggatgaggat                                     870
```

<210> SEQ ID NO 6
<211> LENGTH: 870
<212> TYPE: DNA
<213> ORGANISM: Human immunodeficiency virus
<220> FEATURE:
<221> NAME/KEY: CDS
<222> LOCATION: (1)..(870)

<400> SEQUENCE: 6

```
gta cta ttt tta gat gga ata gat aag gcc caa gat gaa cat gag aaa        48
Val Leu Phe Leu Asp Gly Ile Asp Lys Ala Gln Asp Glu His Glu Lys
 1               5                  10                  15 tat cac agt aat tgg aga gca atg gct agt gat ttt aac ctg cca cct        96
Tyr His Ser Asn Trp Arg Ala Met Ala Ser Asp Phe Asn Leu Pro Pro
             20                  25                  30 gta gta gca aaa gaa ata gta gcc agc tgt gat aaa tgt cag cta aaa       144
Val Val Ala Lys Glu Ile Val Ala Ser Cys Asp Lys Cys Gln Leu Lys
         35                  40                  45 gga gaa gcc atg cat gga caa gta gac tgt agt cca gga ata tgg caa       192
Gly Glu Ala Met His Gly Gln Val Asp Cys Ser Pro Gly Ile Trp Gln
     50                  55                  60 cta gat tgt aca cat tta gaa gga aaa gtt atc ctg gta gca gtt cat       240
Leu Asp Cys Thr His Leu Glu Gly Lys Val Ile Leu Val Ala Val His
 65                  70                  75                  80 gta gcc agt gga tat ata gaa gca gaa gtt att cca gca gaa aca ggg       288
Val Ala Ser Gly Tyr Ile Glu Ala Glu Val Ile Pro Ala Glu Thr Gly
                 85                  90                  95 cag gaa aca gca tat ttt ctt tta aaa tta gca gga aga tgg cca gta       336
Gln Glu Thr Ala Tyr Phe Leu Leu Lys Leu Ala Gly Arg Trp Pro Val
            100                 105                 110 aaa aca ata cat act gac aat ggc agc aat ttc acc ggt gct acg gtt       384
Lys Thr Ile His Thr Asp Asn Gly Ser Asn Phe Thr Gly Ala Thr Val
        115                 120                 125 agg gcc gcc tgt tgg tgg gcg gga atc aag cag gaa ttt gga att ccc       432
Arg Ala Ala Cys Trp Trp Ala Gly Ile Lys Gln Glu Phe Gly Ile Pro
    130                 135                 140 tac aat ccc caa agt caa gga gta gta gaa tct atg aat aaa gaa tta       480
Tyr Asn Pro Gln Ser Gln Gly Val Val Glu Ser Met Asn Lys Glu Leu
```

-continued

| | | |
|---|---|---|
| Tyr Asn Pro Gln Ser Gln Gly Val Val Glu Ser Met Asn Lys Glu Leu<br>145                                 150                    155                    160 | | |
| aag aaa att ata gga cag gta aga gat cag gct gaa cat ctt aag aca<br>Lys Lys Ile Ile Gly Gln Val Arg Asp Gln Ala Glu His Leu Lys Thr<br>                         165                    170                    175 | 528 | |
| gca gta caa atg gca gta ttc atc cac aat ttt aaa aga aaa ggg ggg<br>Ala Val Gln Met Ala Val Phe Ile His Asn Phe Lys Arg Lys Gly Gly<br>        180                    185                    190 | 576 | |
| att ggg ggg tac agt gca ggg gaa aga ata gta gac ata ata gca aca<br>Ile Gly Gly Tyr Ser Ala Gly Glu Arg Ile Val Asp Ile Ile Ala Thr<br>             195                    200                    205 | 624 | |
| gac ata caa act aaa gaa tta caa aaa caa att aca aaa att caa aat<br>Asp Ile Gln Thr Lys Glu Leu Gln Lys Gln Ile Thr Lys Ile Gln Asn<br>210                               215                         220 | 672 | |
| ttt cgg gtt tat tac agg gac agc aga aat cca ctt tgg aaa gga cca<br>Phe Arg Val Tyr Tyr Arg Asp Ser Arg Asn Pro Leu Trp Lys Gly Pro<br>225                               230                    235                240 | 720 | |
| gca aag ctc ctc tgg aaa ggt gaa ggg gca gta gta ata caa gat aat<br>Ala Lys Leu Leu Trp Lys Gly Glu Gly Ala Val Val Ile Gln Asp Asn<br>                        245                    250                    255 | 768 | |
| agt gac ata aaa gta gtg cca aga aga aaa gca aag atc att agg gat<br>Ser Asp Ile Lys Val Val Pro Arg Arg Lys Ala Lys Ile Ile Arg Asp<br>            260                    265                    270 | 816 | |
| tat gga aaa cag atg gca ggt gat gat tgt gtg gca agt aga cag gat<br>Tyr Gly Lys Gln Met Ala Gly Asp Asp Cys Val Ala Ser Arg Gln Asp<br>               275                    280                    285 | 864 | |
| gag gat<br>Glu Asp<br>    290 | 870 | |

<210> SEQ ID NO 7
<211> LENGTH: 168
<212> TYPE: DNA
<213> ORGANISM: Human immunodeficiency virus

<400> SEQUENCE: 7

| | |
|---|---|
| atgcagagag gcaatttag gaaccaaaga aagattgtta agtgtttcaa ttgtggcaaa | 60 |
| gaagggcaca cagccagaaa ttgcagggcc cctaggaaaa agggctgttg gaaatgtgga | 120 |
| aaggaaggac accaaatgaa agattgtact gagagacagg ctaatttt | 168 |

<210> SEQ ID NO 8
<211> LENGTH: 168
<212> TYPE: DNA
<213> ORGANISM: Human immunodeficiency virus
<220> FEATURE:
<221> NAME/KEY: CDS
<222> LOCATION: (1)..(168)

<400> SEQUENCE: 8

| | |
|---|---|
| atg cag aga ggc aat ttt agg aac caa aga aag att gtt aag tgt ttc<br>Met Gln Arg Gly Asn Phe Arg Asn Gln Arg Lys Ile Val Lys Cys Phe<br>1                      5                        10                    15 | 48 |
| aat tgt ggc aaa gaa ggg cac aca gcc aga aat tgc agg gcc cct agg<br>Asn Cys Gly Lys Glu Gly His Thr Ala Arg Asn Cys Arg Ala Pro Arg<br>                  20                    25                    30 | 96 |
| aaa aag ggc tgt tgg aaa tgt gga aag gaa gga cac caa atg aaa gat<br>Lys Lys Gly Cys Trp Lys Cys Gly Lys Glu Gly His Gln Met Lys Asp<br>            35                    40                    45 | 144 |
| tgt act gag aga cag gct aat ttt<br>Cys Thr Glu Arg Gln Ala Asn Phe<br>50                             55 | 168 |

<210> SEQ ID NO 9
<211> LENGTH: 1503
<212> TYPE: DNA
<213> ORGANISM: Human immunodeficiency virus

<400> SEQUENCE: 9

| | |
|---|---|
| atgggtgcga gagcgtcagt attaagcggg ggagaattag atcgatggga aaaaattcgg | 60 |
| ttaaggccag ggggaaagaa aaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggac atcaagcagc catgcaaatg | 600 |
| ttaaaagaga ccatcaatga ggaagctgca gaatgggata gagtgcatcc agtgcatgca | 660 |
| gggcctattg caccaggcca gatgagagaa ccaaggggaa gtgacatagc aggaactact | 720 |
| agtacccttc aggaacaaat aggatggatg acaaataatc cacctatccc agtaggagaa | 780 |
| atttataaaa gatggataat cctgggatta aataaaatag taagaatgta tagccctacc | 840 |
| agcattctgg acataagaca aggaccaaag gaaccctta gagactatgt agaccggttc | 900 |
| tataaaactc taagagccga gcaagcttca caggaggtaa aaaattggat gacagaaacc | 960 |
| ttgttggtcc aaaatgcgaa cccagattgt aagactattt taaaagcatt gggaccagcg | 1020 |
| gctacactag aagaaatgat gacagcatgt cagggagtag gaggacccgg ccataaggca | 1080 |
| agagttttgg ctgaagcaat gagccaagta acaaattcag ctaccataat gatgcagaga | 1140 |
| ggcaatttta ggaaccaaag aaagattgtt aagtgtttca attgtggcaa agaagggcac | 1200 |
| acagccagaa attgcagggc ccctaggaaa aagggctgtt ggaaatgtgg aaggaagga | 1260 |
| caccaaatga aagattgtac tgagagacag gctaattttt tagggaagat ctggccttcc | 1320 |
| tacaagggaa ggccagggaa ttttcttcag agcagaccag agccaacagc cccaccagaa | 1380 |
| gagagcttca ggtctggggt agagacaaca actccccctc agaagcagga gccgatagac | 1440 |
| aaggaactgt atcctttaac ttccctcagg tcactctttg caacgacccc tcgtcacaa | 1500 |
| taa | 1503 |

<210> SEQ ID NO 10
<211> LENGTH: 1503
<212> TYPE: DNA
<213> ORGANISM: Human immunodeficiency virus
<220> FEATURE:
<221> NAME/KEY: CDS
<222> LOCATION: (1)..(1503)

<400> SEQUENCE: 10

| | |
|---|---|
| atg ggt gcg aga gcg tca gta tta agc ggg gga gaa tta gat cga tgg | 48 |
| Met Gly Ala Arg Ala Ser Val Leu Ser Gly Gly Glu Leu Asp Arg Trp | |
| 1               5                   10                  15 | |
| gaa aaa att cgg tta agg cca ggg gga aag aaa aaa tat aaa tta aaa | 96 |
| Glu Lys Ile Arg Leu Arg Pro Gly Gly Lys Lys Lys Tyr Lys Leu Lys | |
|             20                  25                  30 | |

-continued

| | |
|---|---|
| cat ata gta tgg gca agc agg gag cta gaa cga ttc gca gtt aat cct<br>His Ile Val Trp Ala Ser Arg Glu Leu Glu Arg Phe Ala Val Asn Pro<br>           35                     40                   45 | 144 |
| ggc ctg tta gaa aca tca gaa ggc tgt aga caa ata ctg gga cag cta<br>Gly Leu Leu Glu Thr Ser Glu Gly Cys Arg Gln Ile Leu Gly Gln Leu<br>    50                     55                    60 | 192 |
| caa cca tcc ctt cag aca gga tca gaa gaa ctt aga tca tta tat aat<br>Gln Pro Ser Leu Gln Thr Gly Ser Glu Glu Leu Arg Ser Leu Tyr Asn<br>65                    70                    75                80 | 240 |
| aca gta gca acc ctc tat tgt gtg cat caa agg ata gag ata aaa gac<br>Thr Val Ala Thr Leu Tyr Cys Val His Gln Arg Ile Glu Ile Lys Asp<br>                  85                    90                95 | 288 |
| acc aag gaa gct tta gac aag ata gag gaa gag caa aac aaa agt aag<br>Thr Lys Glu Ala Leu Asp Lys Ile Glu Glu Glu Gln Asn Lys Ser Lys<br>           100                  105                110 | 336 |
| aaa aaa gca cag caa gca gca gct gac aca gga cac agc aat cag gtc<br>Lys Lys Ala Gln Gln Ala Ala Ala Asp Thr Gly His Ser Asn Gln Val<br>115                     120                125 | 384 |
| agc caa aat tac cct ata gtg cag aac atc cag ggg caa atg gta cat<br>Ser Gln Asn Tyr Pro Ile Val Gln Asn Ile Gln Gly Gln Met Val His<br>          130                  135                140 | 432 |
| cag gcc ata tca cct aga act tta aat gca tgg gta aaa gta gta gaa<br>Gln Ala Ile Ser Pro Arg Thr Leu Asn Ala Trp Val Lys Val Val Glu<br>145                     150                155                160 | 480 |
| gag aag gct ttc agc cca gaa gtg ata ccc atg ttt tca gca tta tca<br>Glu Lys Ala Phe Ser Pro Glu Val Ile Pro Met Phe Ser Ala Leu Ser<br>                  165                170                175 | 528 |
| gaa gga gcc acc cca caa gat tta aac acc atg cta aac aca gtg ggg<br>Glu Gly Ala Thr Pro Gln Asp Leu Asn Thr Met Leu Asn Thr Val Gly<br>          180                  185                190 | 576 |
| gga cat caa gca gcc atg caa atg tta aaa gag acc atc aat gag gaa<br>Gly His Gln Ala Ala Met Gln Met Leu Lys Glu Thr Ile Asn Glu Glu<br>                  195                200                205 | 624 |
| gct gca gaa tgg gat aga gtg cat cca gtg cat gca ggg cct att gca<br>Ala Ala Glu Trp Asp Arg Val His Pro Val His Ala Gly Pro Ile Ala<br>          210                  215                220 | 672 |
| cca ggc cag atg aga gaa cca agg gga agt gac ata gca gga act act<br>Pro Gly Gln Met Arg Glu Pro Arg Gly Ser Asp Ile Ala Gly Thr Thr<br>225                     230                235                240 | 720 |
| agt acc ctt cag gaa caa ata gga tgg atg aca aat aat cca cct atc<br>Ser Thr Leu Gln Glu Gln Ile Gly Trp Met Thr Asn Asn Pro Pro Ile<br>                  245                250                255 | 768 |
| cca gta gga gaa att tat aaa aga tgg ata atc ctg gga tta aat aaa<br>Pro Val Gly Glu Ile Tyr Lys Arg Trp Ile Ile Leu Gly Leu Asn Lys<br>          260                  265                270 | 816 |
| ata gta aga atg tat agc cct acc agc att ctg gac ata aga caa gga<br>Ile Val Arg Met Tyr Ser Pro Thr Ser Ile Leu Asp Ile Arg Gln Gly<br>            275                  280                285 | 864 |
| cca aag gaa ccc ttt aga gac tat gta gac cgg ttc tat aaa act cta<br>Pro Lys Glu Pro Phe Arg Asp Tyr Val Asp Arg Phe Tyr Lys Thr Leu<br>          290                  295                300 | 912 |
| aga gcc gag caa gct tca cag gag gta aaa aat tgg atg aca gaa acc<br>Arg Ala Glu Gln Ala Ser Gln Glu Val Lys Asn Trp Met Thr Glu Thr<br>305                     310                315                320 | 960 |
| ttg ttg gtc caa aat gcg aac cca gat tgt aag act att tta aaa gca<br>Leu Leu Val Gln Asn Ala Asn Pro Asp Cys Lys Thr Ile Leu Lys Ala<br>                  325                330                335 | 1008 |
| ttg gga cca gcg gct aca cta gaa gaa atg atg aca gca tgt cag gga<br>Leu Gly Pro Ala Ala Thr Leu Glu Glu Met Met Thr Ala Cys Gln Gly | 1056 |

-continued

```
              340                 345                 350
gta gga gga ccc ggc cat aag gca aga gtt ttg gct gaa gca atg agc    1104
Val Gly Gly Pro Gly His Lys Ala Arg Val Leu Ala Glu Ala Met Ser
            355                 360                 365 caa gta aca aat tca gct acc ata atg atg cag aga ggc aat ttt agg    1152
Gln Val Thr Asn Ser Ala Thr Ile Met Met Gln Arg Gly Asn Phe Arg
        370                 375                 380 aac caa aga aag att gtt aag tgt ttc aat tgt ggc aaa gaa ggg cac    1200
Asn Gln Arg Lys Ile Val Lys Cys Phe Asn Cys Gly Lys Glu Gly His
385                 390                 395                 400 aca gcc aga aat tgc agg gcc cct agg aaa aag ggc tgt tgg aaa tgt    1248
Thr Ala Arg Asn Cys Arg Ala Pro Arg Lys Lys Gly Cys Trp Lys Cys
                405                 410                 415 gga aag gaa gga cac caa atg aaa gat tgt act gag aga cag gct aat    1296
Gly Lys Glu Gly His Gln Met Lys Asp Cys Thr Glu Arg Gln Ala Asn
            420                 425                 430 ttt tta ggg aag atc tgg cct tcc tac aag gga agg cca ggg aat ttt    1344
Phe Leu Gly Lys Ile Trp Pro Ser Tyr Lys Gly Arg Pro Gly Asn Phe
        435                 440                 445 ctt cag agc aga cca gag cca aca gcc cca cca gaa gag agc ttc agg    1392
Leu Gln Ser Arg Pro Glu Pro Thr Ala Pro Pro Glu Glu Ser Phe Arg
    450                 455                 460 tct ggg gta gag aca aca act ccc cct cag aag cag gag ccg ata gac    1440
Ser Gly Val Glu Thr Thr Thr Pro Pro Gln Lys Gln Glu Pro Ile Asp
465                 470                 475                 480 aag gaa ctg tat cct tta act tcc ctc agg tca ctc ttt ggc aac gac    1488
Lys Glu Leu Tyr Pro Leu Thr Ser Leu Arg Ser Leu Phe Gly Asn Asp
                485                 490                 495 ccc tcg tca caa taa                                                1503
Pro Ser Ser Gln
            500

<210> SEQ ID NO 11
<211> LENGTH: 43
<212> TYPE: DNA
<213> ORGANISM: Human immunodeficiency virus

<400> SEQUENCE: 11
cagtactaaa gcggcaaaat tagtagattt cgcagaactt aat                    43

<210> SEQ ID NO 12
<211> LENGTH: 43
<212> TYPE: DNA
<213> ORGANISM: Human immunodeficiency virus

<400> SEQUENCE: 12
attaagttct gcgaaatcta ctaattttgc cgctttagta ctg                    43

<210> SEQ ID NO 13
<211> LENGTH: 37
<212> TYPE: DNA
<213> ORGANISM: Human immunodeficiency virus

<400> SEQUENCE: 13
ggcccaagat gaagctgaga aatatgccag taattgg                           37

<210> SEQ ID NO 14
<211> LENGTH: 37
<212> TYPE: DNA
<213> ORGANISM: Human immunodeficiency virus

<400> SEQUENCE: 14
```

```
ccaattactg gcatatttct cagcttcatc ttgggcc                                37

<210> SEQ ID NO 15
<211> LENGTH: 32
<212> TYPE: DNA
<213> ORGANISM: Human immunodeficiency virus

<400> SEQUENCE: 15
gtagccagcg ctgataaagc tcagctaaaa gg                                     32

<210> SEQ ID NO 16
<211> LENGTH: 32
<212> TYPE: DNA
<213> ORGANISM: Human immunodeficiency virus

<400> SEQUENCE: 16 cctttagct gagctttatc agcgctggct ac                                      32

<210> SEQ ID NO 17
<211> LENGTH: 28
<212> TYPE: DNA
<213> ORGANISM: Human immunodeficiency virus

<400> SEQUENCE: 17
ggcaactagc ttgtacacat ttagaagg                                          28

<210> SEQ ID NO 18
<211> LENGTH: 28
<212> TYPE: DNA
<213> ORGANISM: Human immunodeficiency virus

<400> SEQUENCE: 18
ccttctaaat gtgtacaagc tagttgcc                                          28

<210> SEQ ID NO 19
<211> LENGTH: 23
<212> TYPE: DNA
<213> ORGANISM: Human immunodeficiency virus

<400> SEQUENCE: 19
caatacatac tgccaatggc agc                                               23

<210> SEQ ID NO 20
<211> LENGTH: 23
<212> TYPE: DNA
<213> ORGANISM: Human immunodeficiency virus

<400> SEQUENCE: 20
gctgccattg gcagtatgta ttg                                               23

<210> SEQ ID NO 21
<211> LENGTH: 25
<212> TYPE: DNA
<213> ORGANISM: Human immunodeficiency virus

<400> SEQUENCE: 21
ggagtagtag catctatgaa taaag                                             25

<210> SEQ ID NO 22
<211> LENGTH: 25
<212> TYPE: DNA
<213> ORGANISM: Human immunodeficiency virus
```

```
<400> SEQUENCE: 22
ctttattcat agatgctact actcc                                          25

<210> SEQ ID NO 23
<211> LENGTH: 30
<212> TYPE: DNA
<213> ORGANISM: Human immunodeficiency virus

<400> SEQUENCE: 23
aattgcgcgg cccctgcggc agcgggctgt                                     30

<210> SEQ ID NO 24
<211> LENGTH: 30
<212> TYPE: DNA
<213> ORGANISM: Human immunodeficiency virus

<400> SEQUENCE: 24
acagcccgct gccgcagggg ccgcgcaatt                                     30

<210> SEQ ID NO 25
<211> LENGTH: 69
<212> TYPE: DNA
<213> ORGANISM: Human immunodeficiency virus

<400> SEQUENCE: 25
agggccccta ggaaaaaggg ctgttgggca tgtggagcgg aaggacacca aatggcagat    60
tgtactgag                                                            69

<210> SEQ ID NO 26
<211> LENGTH: 75
<212> TYPE: DNA
<213> ORGANISM: Human immunodeficiency virus

<400> SEQUENCE: 26 gcccttttc ctaggggccc tgcaatttgc ggctgtgtgc ccttctgcgc cacaattgaa     60
acacgcaaca atctt                                                     75

<210> SEQ ID NO 27
<211> LENGTH: 1674
<212> TYPE: DNA
<213> ORGANISM: hiv

<400> SEQUENCE: 27
cccattagcc ctattgagac tgtaccagta aaattaaagc caggaatgga tgcccaaaa     60 gttaaacaat ggccattgac agaagaaaaa ataaaagcat tagtagaaat ttgtacagag   120
atggaaaagg aagggaaaat ttcaaaaatt gggcctgaaa atccatacaa tactccagta   180
tttgccataa agaaaaaaga cagtactaaa gcggcaaaat tagtagattt cgcagaactt   240
aataagagaa ctcaagactt ctgggaagtt caattaggaa taccacatcc cgcagggtta   300
aaaaagaaaa aatcagtaac agtactggat gtgggtgatg catatttttc agttccctta   360
gatgaagact tcaggaagta tactgcattt accataccta gtataaacaa tgagacacca   420
gggattagat atcagtacaa tgtgcttcca cagggatgga aggatcacc agcaatattc    480 caaagtagca tgacaaaaat cttagagcct tttagaaaac aaaatccaga catagttatc   540
tatcaataca tggatgattt gtatgtagga tctgacttag aaatagggca gcatagaaca   600
aaaatagagg agctgagaca acatctgttg aggtggggac ttaccacacc agacaaaaaa   660
catcagaaag aacctccatt cctttggatg ggttatgaac tccatcctga taaatggaca   720
```

-continued

```
gtacagccta tagtgctgcc agaaaaagac agctggactg tcaatgacat acagaagtta    780
gtggggaaat tgaattgggc aagtcagatt tacccaggga ttaaagtaag gcaattatgt    840
aaactcctta gaggaaccaa agcactaaca gaagtaatac cactaacaga agaagcagag    900
ctagaactgg cagaaaacag agagattcta aaagaaccag tacatggagt gtattatgac    960
ccatcaaaag acttaatagc agaaatacag aagcaggggc aaggccaatg gacatatcaa   1020
atttatcaag agccatttaa aaatctgaaa acaggaaaat atgcaagaat gagggtgcc    1080 cacactaatg atgtaaaaca attaacagag gcagtgcaaa aaataaccac agaaagcata   1140
gtaatatggg gaaagactcc taaatttaaa ctgcccatac aaaaggaaac atgggaaaca   1200
tggtggacag agtattggca agccacctgg attcctgagt gggagtttgt taatacccct   1260
cccttagtga aattatggta ccagttagag aaagaaccca tagtaggagc agaaaccttc   1320
tatgtagatg gggcagctaa cagggagact aaattaggaa aagcaggata tgttactaat   1380
agaggaagac aaaaagttgt caccctaact gacacaacaa atcagaagac tgagttacaa   1440
gcaatttatc tagctttgca ggattcggga ttagaagtaa acatagtaac agactcacaa   1500
tatgcattag gaatcattca agcacaacca gatcaaagtg aatcagagtt agtcaatcaa   1560
ataatagagc agttaataaa aaaggaaaag gtctatctgg catgggtacc agcacacaaa   1620
ggaattggag gaaatgaaca agtagataaa ttagtcagtg ctggaatcag gaaa         1674
```

<210> SEQ ID NO 28
<211> LENGTH: 1674
<212> TYPE: DNA
<213> ORGANISM: hiv
<220> FEATURE:
<221> NAME/KEY: CDS
<222> LOCATION: (1)..(1674)

<400> SEQUENCE: 28

```
ccc att agc cct att gag act gta cca gta aaa tta aag cca gga atg     48
Pro Ile Ser Pro Ile Glu Thr Val Pro Val Lys Leu Lys Pro Gly Met
 1               5                  10                  15 gat ggc cca aaa gtt aaa caa tgg cca ttg aca gaa gaa aaa ata aaa     96
Asp Gly Pro Lys Val Lys Gln Trp Pro Leu Thr Glu Glu Lys Ile Lys
             20                  25                  30 gca tta gta gaa att tgt aca gag atg gaa aag gaa ggg aaa att tca    144
Ala Leu Val Glu Ile Cys Thr Glu Met Glu Lys Glu Gly Lys Ile Ser
         35                  40                  45 aaa att ggg cct gaa aat cca tac aat act cca gta ttt gcc ata aag    192
Lys Ile Gly Pro Glu Asn Pro Tyr Asn Thr Pro Val Phe Ala Ile Lys
     50                  55                  60 aaa aaa gac agt act aaa gcg gca aaa tta gta gat ttc gca gaa ctt    240
Lys Lys Asp Ser Thr Lys Ala Ala Lys Leu Val Asp Phe Ala Glu Leu
 65                  70                  75                  80 aat aag aga act caa gac ttc tgg gaa gtt caa tta gga ata cca cat    288
Asn Lys Arg Thr Gln Asp Phe Trp Glu Val Gln Leu Gly Ile Pro His
                 85                  90                  95 ccc gca ggg tta aaa aag aaa aaa tca gta aca gta ctg gat gtg ggt    336
Pro Ala Gly Leu Lys Lys Lys Lys Ser Val Thr Val Leu Asp Val Gly
            100                 105                 110 gat gca tat ttt tca gtt ccc tta gat gaa gac ttc agg aag tat act    384
Asp Ala Tyr Phe Ser Val Pro Leu Asp Glu Asp Phe Arg Lys Tyr Thr
        115                 120                 125 gca ttt acc ata cct agt ata aac aat gag aca cca ggg att aga tat    432
Ala Phe Thr Ile Pro Ser Ile Asn Asn Glu Thr Pro Gly Ile Arg Tyr
    130                 135                 140
```

```
cag tac aat gtg ctt cca cag gga tgg aaa gga tca cca gca ata ttc      480
Gln Tyr Asn Val Leu Pro Gln Gly Trp Lys Gly Ser Pro Ala Ile Phe
145                 150                 155                 160 caa agt agc atg aca aaa atc tta gag cct ttt aga aaa caa aat cca      528
Gln Ser Ser Met Thr Lys Ile Leu Glu Pro Phe Arg Lys Gln Asn Pro
            165                 170                 175 gac ata gtt atc tat caa tac atg gat gat ttg tat gta gga tct gac      576
Asp Ile Val Ile Tyr Gln Tyr Met Asp Asp Leu Tyr Val Gly Ser Asp
        180                 185                 190 tta gaa ata ggg cag cat aga aca aaa ata gag gag ctg aga caa cat      624
Leu Glu Ile Gly Gln His Arg Thr Lys Ile Glu Glu Leu Arg Gln His
    195                 200                 205 ctg ttg agg tgg gga ctt acc aca cca gac aaa aaa cat cag aaa gaa      672
Leu Leu Arg Trp Gly Leu Thr Thr Pro Asp Lys Lys His Gln Lys Glu
210                 215                 220 cct cca ttc ctt tgg atg ggt tat gaa ctc cat cct gat aaa tgg aca      720
Pro Pro Phe Leu Trp Met Gly Tyr Glu Leu His Pro Asp Lys Trp Thr
225                 230                 235                 240 gta cag cct ata gtg ctg cca gaa aaa gac agc tgg act gtc aat gac      768
Val Gln Pro Ile Val Leu Pro Glu Lys Asp Ser Trp Thr Val Asn Asp
            245                 250                 255 ata cag aag tta gtg ggg aaa ttg aat tgg gca agt cag att tac cca      816
Ile Gln Lys Leu Val Gly Lys Leu Asn Trp Ala Ser Gln Ile Tyr Pro
        260                 265                 270 ggg att aaa gta agg caa tta tgt aaa ctc ctt aga gga acc aaa gca      864
Gly Ile Lys Val Arg Gln Leu Cys Lys Leu Leu Arg Gly Thr Lys Ala
    275                 280                 285 cta aca gaa gta ata cca cta aca gaa gaa gca gag cta gaa ctg gca      912
Leu Thr Glu Val Ile Pro Leu Thr Glu Glu Ala Glu Leu Glu Leu Ala
290                 295                 300 gaa aac aga gag att cta aaa gaa cca gta cat gga gtg tat tat gac      960
Glu Asn Arg Glu Ile Leu Lys Glu Pro Val His Gly Val Tyr Tyr Asp
305                 310                 315                 320 cca tca aaa gac tta ata gca gaa ata cag aag cag ggg caa ggc caa     1008
Pro Ser Lys Asp Leu Ile Ala Glu Ile Gln Lys Gln Gly Gln Gly Gln
            325                 330                 335 tgg aca tat caa att tat caa gag cca ttt aaa aat ctg aaa aca gga     1056
Trp Thr Tyr Gln Ile Tyr Gln Glu Pro Phe Lys Asn Leu Lys Thr Gly
        340                 345                 350 aaa tat gca aga atg agg ggt gcc cac act aat gat gta aaa caa tta     1104
Lys Tyr Ala Arg Met Arg Gly Ala His Thr Asn Asp Val Lys Gln Leu
    355                 360                 365 aca gag gca gtg caa aaa ata acc aca gaa agc ata gta ata tgg gga     1152
Thr Glu Ala Val Gln Lys Ile Thr Thr Glu Ser Ile Val Ile Trp Gly
370                 375                 380 aag act cct aaa ttt aaa ctg ccc ata caa aag gaa aca tgg gaa aca     1200
Lys Thr Pro Lys Phe Lys Leu Pro Ile Gln Lys Glu Thr Trp Glu Thr
385                 390                 395                 400 tgg tgg aca gag tat tgg caa gcc acc tgg att cct gag tgg gag ttt     1248
Trp Trp Thr Glu Tyr Trp Gln Ala Thr Trp Ile Pro Glu Trp Glu Phe
            405                 410                 415 gtt aat acc cct ccc tta gtg aaa tta tgg tac cag tta gag aaa gaa     1296
Val Asn Thr Pro Pro Leu Val Lys Leu Trp Tyr Gln Leu Glu Lys Glu
        420                 425                 430 ccc ata gta gga gca gaa acc ttc tat gta gat ggg gca gct aac agg     1344
Pro Ile Val Gly Ala Glu Thr Phe Tyr Val Asp Gly Ala Ala Asn Arg
    435                 440                 445 gag act aaa tta gga aaa gca gga tat gtt act aat aga gga aga caa     1392
Glu Thr Lys Leu Gly Lys Ala Gly Tyr Val Thr Asn Arg Gly Arg Gln
```

-continued

| | | | | | | | | | | | | | | | |
|---|---|---|---|---|---|---|---|---|---|---|---|---|---|---|---|
| | | | | 450 | | | | | 455 | | | | | 460 | |
| aaa | gtt | gtc | acc | cta | act | gac | aca | aca | aat | cag | aag | act | gag | tta | caa | 1440 |
| Lys | Val | Val | Thr | Leu | Thr | Asp | Thr | Thr | Asn | Gln | Lys | Thr | Glu | Leu | Gln |
| 465 | | | | 470 | | | | | 475 | | | | | 480 | |

| gca | att | tat | cta | gct | ttg | cag | gat | tcg | gga | tta | gaa | gta | aac | ata | gta | 1488 |
|---|---|---|---|---|---|---|---|---|---|---|---|---|---|---|---|---|
| Ala | Ile | Tyr | Leu | Ala | Leu | Gln | Asp | Ser | Gly | Leu | Glu | Val | Asn | Ile | Val |
| | | | | 485 | | | | | 490 | | | | | 495 | |

| aca | gac | tca | caa | tat | gca | tta | gga | atc | att | caa | gca | caa | cca | gat | caa | 1536 |
|---|---|---|---|---|---|---|---|---|---|---|---|---|---|---|---|---|
| Thr | Asp | Ser | Gln | Tyr | Ala | Leu | Gly | Ile | Ile | Gln | Ala | Gln | Pro | Asp | Gln |
| | | | 500 | | | | | 505 | | | | | 510 | | |

| agt | gaa | tca | gag | tta | gtc | aat | caa | ata | ata | gag | cag | tta | ata | aaa | aag | 1584 |
|---|---|---|---|---|---|---|---|---|---|---|---|---|---|---|---|---|
| Ser | Glu | Ser | Glu | Leu | Val | Asn | Gln | Ile | Ile | Glu | Gln | Leu | Ile | Lys | Lys |
| | | | 515 | | | | | 520 | | | | | 525 | | |

| gaa | aag | gtc | tat | ctg | gca | tgg | gta | cca | gca | cac | aaa | gga | att | gga | gga | 1632 |
|---|---|---|---|---|---|---|---|---|---|---|---|---|---|---|---|---|
| Glu | Lys | Val | Tyr | Leu | Ala | Trp | Val | Pro | Ala | His | Lys | Gly | Ile | Gly | Gly |
| | 530 | | | | | 535 | | | | | 540 | | | | |

| aat | gaa | caa | gta | gat | aaa | tta | gtc | agt | gct | gga | atc | agg | aaa | | | 1674 |
|---|---|---|---|---|---|---|---|---|---|---|---|---|---|---|---|---|
| Asn | Glu | Gln | Val | Asp | Lys | Leu | Val | Ser | Ala | Gly | Ile | Arg | Lys | | | |
| 545 | | | | 550 | | | | 555 | | | | | | | | |

<210> SEQ ID NO 29
<211> LENGTH: 863
<212> TYPE: DNA
<213> ORGANISM: hiv

<400> SEQUENCE: 29

| | | |
|---|---|---|
| gtactatttt tagatggaat agataaggcc caagatgaag ctgagaaata tgccagtaat | 60 |
| tggagagcaa tggctagtga ttttaacctg ccacctgtag tagcaaaaga aatagtagcc | 120 |
| agcgctgata agctcagct aaaaggagaa gccatgcatg acaagtaga ctgtagtcca | 180 |
| ggaatatggc aactagcttg tacacattta gaaggaaaag ttatcctggt agcagttcat | 240 |
| gtagccagtg gatatataga agcagaagtt attccagcag aaacagggca ggaaacagca | 300 |
| tattttcttt taaaattagc aggaagatgg ccagtaaaaa caatacatac tgccaatggc | 360 |
| agcaatttca ccggtgctac ggttagggcc gcctgttggt gggcgggaat caagcaggaa | 420 |
| tttggaattc cctacaatcc ccaaagtcaa ggagtagtag catctatgaa taagaatta | 480 |
| aagaaaatta taggacaggt aagagatcag gctgaacatc ttaagacagc agtacaaatg | 540 |
| gcagtattca tccacaattt taaaagaaaa ggggggattg gggggtacag tgcaggggaa | 600 |
| agaatagtag acataatagc aacagacata caaactaaag aattacaaaa acaaattaca | 660 |
| aaaattcaaa attttcgggt ttattacagg gacagcagaa atccactttg gaaaggacca | 720 |
| gcaaagctcc tctggaaagg tgaaggggca gtagtaatac aagataatag tgacataaaa | 780 |
| gtagtgccaa gaagaaaagc aaagatcatt agggattatg gaaaacagat ggcaggtgat | 840 |
| gattgtgtgg caagtagaca gga | 863 |

<210> SEQ ID NO 30
<211> LENGTH: 863
<212> TYPE: DNA
<213> ORGANISM: hiv
<220> FEATURE:
<221> NAME/KEY: CDS
<222> LOCATION: (1)..(861)

<400> SEQUENCE: 30

| | | | | | | | | | | | | | | | |
|---|---|---|---|---|---|---|---|---|---|---|---|---|---|---|---|
| gta | cta | ttt | tta | gat | gga | ata | gat | aag | gcc | caa | gat | gaa | gct | gag | aaa | 48 |
| Val | Leu | Phe | Leu | Asp | Gly | Ile | Asp | Lys | Ala | Gln | Asp | Glu | Ala | Glu | Lys |
| 1 | | | | 5 | | | | | 10 | | | | | 15 | |

| | | | | | | | | | | | | | | | |
|---|---|---|---|---|---|---|---|---|---|---|---|---|---|---|---|
| tat | gcc | agt | aat | tgg | aga | gca | atg | gct | agt | gat | ttt | aac | ctg | cca | cct | 96 |
| Tyr | Ala | Ser | Asn | Trp | Arg | Ala | Met | Ala | Ser | Asp | Phe | Asn | Leu | Pro | Pro |
| | | 20 | | | | 25 | | | | 30 | | | | | |
| gta | gta | gca | aaa | gaa | ata | gta | gcc | agc | gct | gat | aaa | gct | cag | cta | aaa | 144 |
| Val | Val | Ala | Lys | Glu | Ile | Val | Ala | Ser | Ala | Asp | Lys | Ala | Gln | Leu | Lys |
| | 35 | | | | 40 | | | | 45 | | | | | | |
| gga | gaa | gcc | atg | cat | gga | caa | gta | gac | tgt | agt | cca | gga | ata | tgg | caa | 192 |
| Gly | Glu | Ala | Met | His | Gly | Gln | Val | Asp | Cys | Ser | Pro | Gly | Ile | Trp | Gln |
| 50 | | | | 55 | | | | 60 | | | | | | | |
| cta | gct | tgt | aca | cat | tta | gaa | gga | aaa | gtt | atc | ctg | gta | gca | gtt | cat | 240 |
| Leu | Ala | Cys | Thr | His | Leu | Glu | Gly | Lys | Val | Ile | Leu | Val | Ala | Val | His |
| 65 | | | | 70 | | | | 75 | | | | 80 | | | |
| gta | gcc | agt | gga | tat | ata | gaa | gca | gaa | gtt | att | cca | gca | gaa | aca | ggg | 288 |
| Val | Ala | Ser | Gly | Tyr | Ile | Glu | Ala | Glu | Val | Ile | Pro | Ala | Glu | Thr | Gly |
| | | | | 85 | | | | 90 | | | | | 95 | | |
| cag | gaa | aca | gca | tat | ttt | ctt | tta | aaa | tta | gca | gga | aga | tgg | cca | gta | 336 |
| Gln | Glu | Thr | Ala | Tyr | Phe | Leu | Leu | Lys | Leu | Ala | Gly | Arg | Trp | Pro | Val |
| | | 100 | | | | | 105 | | | | 110 | | | | |
| aaa | aca | ata | cat | act | gcc | aat | ggc | agc | aat | ttc | acc | ggt | gct | acg | gtt | 384 |
| Lys | Thr | Ile | His | Thr | Ala | Asn | Gly | Ser | Asn | Phe | Thr | Gly | Ala | Thr | Val |
| | | 115 | | | | | 120 | | | | 125 | | | | |
| agg | gcc | gcc | tgt | tgg | tgg | gcg | gga | atc | aag | cag | gaa | ttt | gga | att | ccc | 432 |
| Arg | Ala | Ala | Cys | Trp | Trp | Ala | Gly | Ile | Lys | Gln | Glu | Phe | Gly | Ile | Pro |
| 130 | | | | | 135 | | | | 140 | | | | | | |
| tac | aat | ccc | caa | agt | caa | gga | gta | gta | gca | tct | atg | aat | aaa | gaa | tta | 480 |
| Tyr | Asn | Pro | Gln | Ser | Gln | Gly | Val | Val | Ala | Ser | Met | Asn | Lys | Glu | Leu |
| 145 | | | | | 150 | | | | 155 | | | | | 160 | |
| aag | aaa | att | ata | gga | cag | gta | aga | gat | cag | gct | gaa | cat | ctt | aag | aca | 528 |
| Lys | Lys | Ile | Ile | Gly | Gln | Val | Arg | Asp | Gln | Ala | Glu | His | Leu | Lys | Thr |
| | | | | 165 | | | | 170 | | | | 175 | | | |
| gca | gta | caa | atg | gca | gta | ttc | atc | cac | aat | ttt | aaa | aga | aaa | ggg | ggg | 576 |
| Ala | Val | Gln | Met | Ala | Val | Phe | Ile | His | Asn | Phe | Lys | Arg | Lys | Gly | Gly |
| | | 180 | | | | | 185 | | | | 190 | | | | |
| att | ggg | ggg | tac | agt | gca | ggg | gaa | aga | ata | gta | gac | ata | ata | gca | aca | 624 |
| Ile | Gly | Gly | Tyr | Ser | Ala | Gly | Glu | Arg | Ile | Val | Asp | Ile | Ile | Ala | Thr |
| | | 195 | | | | 200 | | | | 205 | | | | | |
| gac | ata | caa | act | aaa | gaa | tta | caa | aaa | caa | att | aca | aaa | att | caa | aat | 672 |
| Asp | Ile | Gln | Thr | Lys | Glu | Leu | Gln | Lys | Gln | Ile | Thr | Lys | Ile | Gln | Asn |
| 210 | | | | | 215 | | | | 220 | | | | | | |
| ttt | cgg | gtt | tat | tac | agg | gac | agc | aga | aat | cca | ctt | tgg | aaa | gga | cca | 720 |
| Phe | Arg | Val | Tyr | Tyr | Arg | Asp | Ser | Arg | Asn | Pro | Leu | Trp | Lys | Gly | Pro |
| 225 | | | | 230 | | | | | 235 | | | | | 240 | |
| gca | aag | ctc | ctc | tgg | aaa | ggt | gaa | ggg | gca | gta | gta | ata | caa | gat | aat | 768 |
| Ala | Lys | Leu | Leu | Trp | Lys | Gly | Glu | Gly | Ala | Val | Val | Ile | Gln | Asp | Asn |
| | | | | 245 | | | | 250 | | | | 255 | | | |
| agt | gac | ata | aaa | gta | gtg | cca | aga | aga | aaa | gca | aag | atc | att | agg | gat | 816 |
| Ser | Asp | Ile | Lys | Val | Val | Pro | Arg | Arg | Lys | Ala | Lys | Ile | Ile | Arg | Asp |
| | | 260 | | | | | 265 | | | | 270 | | | | |
| tat | gga | aaa | cag | atg | gca | ggt | gat | gat | tgt | gtg | gca | agt | aga | cag | ga | 863 |
| Tyr | Gly | Lys | Gln | Met | Ala | Gly | Asp | Asp | Cys | Val | Ala | Ser | Arg | Gln |
| | 275 | | | | | 280 | | | | 285 | | | | | |

<210> SEQ ID NO 31
<211> LENGTH: 168
<212> TYPE: DNA
<213> ORGANISM: hiv

<400> SEQUENCE: 31
atgcagagag gcaattttag gaaccaaaga aagattgttg cgtgtttcaa ttgtggcgca    60
gaagggcaca cagccgcaaa ttgcgcggcc cctgcggcag cgggctgttg ggcatgtgga   120

```
gcggaaggac accaaatggc agattgtact gagagacagg ctaatttt            168
```

```
<210> SEQ ID NO 32
<211> LENGTH: 168
<212> TYPE: DNA
<213> ORGANISM: hiv
<220> FEATURE:
<221> NAME/KEY: CDS
<222> LOCATION: (1)..(168)

<400> SEQUENCE: 32
```

```
atg cag aga ggc aat ttt agg aac caa aga aag att gtt gcg tgt ttc       48
Met Gln Arg Gly Asn Phe Arg Asn Gln Arg Lys Ile Val Ala Cys Phe
 1               5                  10                  15 aat tgt ggc gca gaa ggg cac aca gcc gca aat tgc gcg gcc cct gcg       96
Asn Cys Gly Ala Glu Gly His Thr Ala Ala Asn Cys Ala Ala Pro Ala
             20                  25                  30 gca gcg ggc tgt tgg gca tgt gga gcg gaa gga cac caa atg gca gat      144
Ala Ala Gly Cys Trp Ala Cys Gly Ala Glu Gly His Gln Met Ala Asp
         35                  40                  45 tgt act gag aga cag gct aat ttt                                      168
Cys Thr Glu Arg Gln Ala Asn Phe
     50                  55
```

```
<210> SEQ ID NO 33
<211> LENGTH: 12425
<212> TYPE: DNA
<213> ORGANISM: hiv

<400> SEQUENCE: 33
```

```
ggcctcagag gccttcaata ttggccatta gccatattat tcattggtta tatagcataa     60
atcaatattg gctattggcc attgcatacg ttgtatctat atcataatat gtacatttat    120
attggctcat gtccaatatg accgccatgt tggcattgat tattgactag ttattaatag    180
taatcaatta cggggtcatt agttcatagc ccatatatgg agttccgcgt tacataactt    240
acggtaaatg gcccgcctgg ctgaccgccc aacgaccccc gcccattgac gtcaataatg    300
acgtatgttc ccatagtaac gccaataggg actttccatt gacgtcaatg ggtggagtat    360
ttacggtaaa ctgcccactt ggcagtacat caagtgtatc atatgccaag tccgccccct    420
attgacgtca atgacggtaa atggcccgcc tggcattatg cccagtacat gaccttacgg    480
gactttccta cttggcagta catctacgta ttagtcatcg ctattaccat ggtgatgcgg    540
ttttggcagt acaccaatgg gcgtggatag cggtttgact cacggggatt tccaagtctc    600
cacccccattg acgtcaatgg gagtttgttt tggcaccaaa atcaacggga ctttccaaaa    660
tgtcgtaata accccgcccc gttgacgcaa atgggcggta ggcgtgtacg gtgggaggtc    720
tatataagca gagctcgttt agtgaaccgt cagatcacta aagctttat tgcggtagtt    780
tatcacagtt aaattgctaa cgcagtcagt gctccggcgc cgaacaggg acctgaaagc    840
gaaagggaaa ccagaggagc tctctcgacg caggactcgg cttgctgaag cgcgcacggc    900
aagaggcgag gggcggcgac tggtgagtac gccaaaaatt ttgactagcg gaggctagaa    960
ggagagagat gggtgcgaga gcgtcagtat taagcggggg agaattagat cgatgggaaa   1020
aaattcggtt aaggccaggg ggaaagaaaa aatataaatt aaaacatata gtatgggcaa   1080
gcagggagct agaacgattc gcagttaatc ctggcctgtt agaaacatca gaaggctgta   1140
gacaaatact gggacagcta caaccatccc ttcagacagg atcagaagaa cttagatcat   1200
tatataatac agtagcaacc ctctattgtg tgcatcaaag gatagagata aagacacca   1260
```

-continued

```
aggaagcttt agacaagata gaggaagagc aaaacaaaag taagaaaaaa gcacagcaag    1320
cagcagctga cacaggacac agcaatcagg tcagccaaaa ttaccctata gtgcagaaca    1380
tccaggggca aatggtacat caggccatat cacctgaaac tttaaatgca tgggtaaaag    1440
tagtagaaga gaaggctttc agcccagaag tgatacccat gttttcagca ttatcagaag    1500
gagccacccc acaagattta aacaccatgc taaacacagt gggggacat caagcagcca     1560 tgcaaatgtt aaaagagacc atcaatgagg aagctgcaga atgggataga gtgcatccag    1620
tgcatgcagg gcctattgca ccaggccaga tgagagaacc aaggggaagt gacatagcag    1680
gaactactag tacccttcag gaacaaatag gatggatgac aaataatcca cctatcccag    1740
taggagaaat ttataaaaga tggataatcc tgggattaaa taaaatagta agaatgtata    1800
gccctaccag cattctggac ataagacaag gaccaaagga acccttagat gactatgtag    1860
accggttcta taaaactcta agagccgagc aagcttcaca ggaggtaaaa aattggatga    1920
cagaaccctt gttggtccaa aatgcgaacc cagattgtaa gactatttta aaagcattgg    1980
gaccagcggc tacactagaa gaaatgatga cagcatgtca gggagtagga ggacccggcc    2040
ataaggcaag agttttggct gaagcaatga gccaagtaac aaattcagct accataatga    2100
tgcagagagg caattttagg aaccaaagaa agattgttgc gtgtttcaat tgtggcgcag    2160
aagggcacac agccgcaaat tgcgcggccc ctgcggcagc gggctgttgg gcatgtggag    2220
cggaaggaca ccaaatggca gattgtactg agagacaggc taattttta gggaagatct    2280 ggccttccta caagggaagg ccagggaatt tccttcagag cagaccagag ccaacagccc    2340
caccagaaga gagcttcagg tctggggtag agacaacaac tccccctcag aagcaggagc    2400
cgatagacaa ggaactgtat cctttaactt ccctcaggtc actctttggc aacgacccct    2460
cgtcacaata agatagggg ggcaactaaa ggaagctcta ttagatacag gagcagatga    2520
tacagtatta gaagaaatga gtttgccagg aagatggaaa ccaaaaatga taggggaat    2580 tggaggtttt atcaaagtaa gacagtatga tcagatactc atagaaatct gtggacataa    2640
agctataggt acagtattag taggacctac acctgtcaac ataattggaa gaaatctgtt    2700
gactcagatt ggttgcactt taaattttcc cattagccct attgagactg taccagtaaa    2760
attaaagcca ggaatggatg gcccaaaagt taaacaatgg ccattgacag aagaaaaat    2820 aaaagcatta gtagaaattt gtacagagat ggaaaaggaa gggaaaattt caaaaattgg    2880
gcctgaaaat ccatacaata ctccagtatt tgccataaag aaaaaagaca gtactaaagc    2940
ggcaaaatta gtagatttcg cagaacttaa taagagaact caagacttct gggaagttca    3000
attaggaata ccacatcccg cagggttaaa aaagaaaaaa tcagtaacag tactggatgt    3060
gggtgatgca tatttttcag ttcccttaga tgaagacttc aggaagtata ctgcatttac    3120
catacctagt ataaacaatg agacaccagg gattagatat cagtacaatg tgcttccaca    3180
gggatggaaa ggatcaccag caatattcca aagtagcatg acaaaaatct tagagccttt    3240
tagaaaacaa aatccagaca tagttatcta tcaatacatg gatgatttgt atgtaggatc    3300
tgacttagaa ataggcagc atagaacaaa aatagaggag ctgagacaac atctgttgag    3360
gtggggactt accacaccag acaaaaaaca tcagaaagaa cctccattcc tttggatggg    3420
ttatgaactc catcctgata atggacagt acagcctata gtgctgccag aaaaagacag    3480
ctggactgtc aatgacatac agaagttagt ggggaaattg aattgggcaa gtcagattta    3540
cccagggatt aaagtaaggc aattatgtaa actccttaga ggaaccaaag cactaacaga    3600
```

```
agtaataccc ctaacagaag aagcagagct agaactggca gaaaacagag agattctaaa   3660
agaaccagta catggagtgt attatgaccc atcaaaagac ttaatagcag aaatacagaa   3720 gcagggcaa ggccaatgga catatcaaat ttatcaagag ccatttaaaa atctgaaaac    3780
aggaaaatat gcaagaatga ggggtgccca cactaatgat gtaaacaat taacagaggc    3840 agtgcaaaaa ataaccacag aaagcatagt aatatgggga aagactccta aatttaaact   3900
gcccatacaa aaggaaacat gggaaacatg gtggacagag tattggcaag ccacctggat   3960
tcctgagtgg gagtttgtta ataccctcc cttagtgaaa ttatggtacc agttagagaa     4020
agaacccata gtaggagcag aaaccttcta tgtagatggg gcagctaaca gggagactaa   4080
attaggaaaa gcaggatatg ttactaatag aggaagacaa aaagttgtca ccctaactga   4140
cacaacaaat cagaagactg agttacaagc aatttatcta gctttgcagg attcgggatt   4200
agaagtaaac atagtaacag actcacaata tgcattagga atcattcaag cacaaccaga   4260
tcaaagtgaa tcagagttag tcaatcaaat aatagagcag ttaataaaaa aggaaaaggt   4320
ctatctggca tgggtaccag cacacaaagg aattggagga aatgaacaag tagataaatt   4380
agtcagtgct ggaatcagga aagtactatt tttagatgga atagataagg cccaagatga   4440
agctgagaaa tatgccagta attggagagc aatggctagt gattttaacc tgccacctgt   4500
agtagcaaaa gaaatagtag ccagcgctga taaagctcag ctaaaaggag aagccatgca   4560
tggacaagta gactgtagtc caggaatatg gcaactagct tgtacacatt tagaaggaaa   4620
agttatcctg gtagcagttc atgtagccag tggatatata gaagcagaag ttattccagc   4680
agaaacaggg caggaaacag catattttct tttaaaatta gcaggaagat ggccagtaaa   4740
aacaatacat actgccaatg gcagcaattt caccggtgct acggttaggg ccgcctgttg   4800
gtgggcggga atcaagcagg aatttggaat tccctacaat ccccaaagtc aaggagtagt   4860
agcatctatg aataaagaat taaagaaaat tataggacag gtaagagatc aggctgaaca   4920
tcttaagaca gcagtacaaa tggcagtatt catccacaat tttaaaagaa aaggggggat   4980
tggggggtac agtgcagggg aaagaatagt agacataata gcaacagaca tacaaactaa   5040
agaattacaa aaacaaatta caaaaattca aaattttcgg gtttattaca gggacagcag   5100
aaatccactt tggaaaggac cagcaaagct cctctggaaa ggtgaagggg cagtagtaat   5160
acaagataat agtgacataa aagtagtgcc aagaagaaaa gcaaagatca ttagggatta   5220
tggaaaacag atggcaggtg atgattgtgt ggcaagtaga caggatgagg attagaacat   5280
ggaaaagttt agtaaaacac catatgtatg tttcagggaa agctagggga tggttttata   5340
gacatcacta tgaaagccct catccaagaa taagttcaga agtacacatc ccactagggg   5400
atgctagatt ggtaataaca acatattggg gtctgcatac aggagaaaga gactggcatt   5460
tgggtcaggg agtctccata gaatggagga aaaagagata tagcacacaa gtagaccctg   5520
aactagcaga ccaactaatt catctgtatt actttgactg ttttttcagac tctgctataa   5580 gaaaggcctt attaggacac atagttagcc ctaggtgtga atatcaagca ggacataaca   5640
aggtaggatc tctacaatac ttggcactag cagcattaat aacaccaaaa aagataaagc   5700 caccttttgcc tagtgttacg aaactgacag aggatagatg gaacaagccc cagaagacca   5760
agggccacag agggagccac acaatgaatg gacactagag cttttagagg agcttaagaa   5820
tgaagctgtt agacattttc ctaggatttg gctccatggc ttagggcaac atatctatga   5880
aacttatggg gatacttggg caggagtgga agccataata agaattctgc aacaactgct   5940
gtttatccat tttcagaatt gggtgtcgac atagcagaat aggcgttact cgacagagga   6000
```

-continued

```
gagcaagaaa tggagccagt agatcctaga ctagagccct ggaagcatcc aggaagtcag    6060
cctaaaactg cttgtaccaa ttgctattgt aaaaagtgtt gctttcattg ccaagtttgt    6120
ttcataacaa aagccttagg catctcctat ggcaggaaga agcggagaca gcgacgaaga    6180
gctcatcaga acagtcagac tcatcaagct tctctatcaa agcagtaagt agtacatgta    6240
acgcaaccta taccaatagt agcaatagta gcattagtag tagcaataat aatagcaata    6300
gttgtgtggt ccatagtaat catagaatat aggaaaatat taagacaaag aaaaatagac    6360
aggttaattg atagactaat agaaagagca gaagacagtg gcaatgagag tgaaggagaa    6420
atatcagcac ttgtggagat ggggggtggag atggggcacc atgctccttg ggatgttgat    6480
gatctgtagt gctacagaaa aattgtgggt cacagtctat tatggggtac ctgtgtggaa    6540
ggaagcaacc accactctat tttgtgcatc agatgctaaa gcatatgata cagaggtaca    6600
taatgtttgg gccacacatg cctgtgtacc cacagacccc aacccacaag aagtagtatt    6660
ggtaaatgtg acagaaaatt ttaacatgtg gaaaaatgac atggtagaac agatgcatga    6720
ggatataatc agtttatggg atcaaagcct aaagccatgt gtaaaattaa ccccactctg    6780
tgttagttta aagtgcactg atttgaagaa tgatactaat accaatagta gtagcgggag    6840
aatgataatg gagaaggag agataaaaaa ctgctctttc aatatcagca caagcataag    6900
aggtaaggtg cagaaagaat atgcattttt ttataaactt gatataatac caatagataa    6960
tgatactacc agctataagt tgacaagttg taacacctca gtcattacac aggcctgtcc    7020
aaaggtatcc tttgagccaa ttcccataca ttattgtgcc ccggctggtt ttgcgattct    7080
aaaatgtaat aataagacgt tcaatggaac aggaccatgt acaaatgtca gcacagtaca    7140
atgtacacat ggaattaggc cagtagtatc aactcaactg ctgttaaatg gcagtctagc    7200
agaagaagag gtagtaatta gatctgtcaa tttcacggac aatgctaaaa ccataatagt    7260
acagctgaac acatctgtag aaattaattg tacaagaccc aacaacaata caagaaaaag    7320
aatccgtatc cagagaggac cagggagagc atttgttaca ataggaaaaa taggaaatat    7380
gagacaagca cattgtaaca ttagtagagc aaaatggaat aacactttaa aacagatagc    7440
tagcaaatta agagaacaat ttggaaataa taaaacaata atctttaagc aatcctcagg    7500
aggggaccca gaaattgtaa cgcacagttt taattgtgga ggggaatttt tctactgtaa    7560
ttcaacacaa ctgtttaata gtacttggtt taatagtact tggagtactg aagggtcaaa    7620
taacactgaa ggaagtgaca caatcaccct cccatgcaga ataaaacaaa ttataaacat    7680
gtggcagaaa gtaggaaaag caatgtatgc ccctcccatc agtggacaaa ttagatgttc    7740
atcaaatatt acagggctgc tattaacaag agatggtggt aatagcaaca atgagtccga    7800
gatcttcaga cctggaggag gagatatgag ggacaattgg agaagtgaat tatataaata    7860
taaagtagta aaaattgaac cattaggagt agcacccacc aaggcaaaga gaagagtggt    7920
gcagagagaa aaaagagcag tgggaatagg agctttgttc cttgggttct gggagcagc    7980 aggaagcact atgggcgcag cctcaatgac gctgacggta caggccagac aattattgtc    8040
tggtatagtg cagcagcaga acaatttgct gagggctatt gaggcgcaac agcatctgtt    8100
gcaactcaca gtctgggggca tcaagcagct ccaggcaaga atcctggctg tggaaagata    8160
cctaaaggat caacagctcc tggggatttg gggttgctct ggaaaactca tttgcaccac    8220
tgctgtgcct tggaatgcta gttggagtaa taaatctctg gaacagattt ggaatcacac    8280
gacctggatg gagtgggaca gagaaattaa caattacaca agcttaatac actccttaat    8340
```

```
tgaagaatcg caaaaccagc aagaaaagaa tgaacaagaa ttattggaat tagataaatg    8400
ggcaagtttg tggaattggt ttaacataac aaattggctg tggtatataa aattattcat    8460
aatgatagta ggaggcttgg taggtttaag aatagttttt gctgtacttt ctatagtgaa    8520
tagagttagg cagggatatt caccattatc gtttcagacc cacctcccaa ccccgagggg    8580
acccgacagg cccgaaggaa tagaagaaga aggtggagag agagacagag acagatccat    8640
tcgattagtg aacggatcct tggcacttat ctgggacgat ctgcggagcc tgtgcctctt    8700
cagctaccac cgcttgagag acttactctt gattgtaacg aggattgtgg aacttctggg    8760 acgcagggggg tgggaagccc tcaaatattg gtggaatctc ctacagtatt ggagtcagga    8820 actaagaat agtgctgtta gcttgctcaa tgccacagcc atagcagtag ctgaggggac    8880
agatagggtt atagaagtag tacaaggagc ttgtagagct attcgccaca tacctagaag    8940
aataagacag ggcttggaaa ggattttgct ataagatggg tggcaagtgg tcaaaaagta    9000
gtgtgattgg atggcctact gtaagggaaa gaatgagacg agctgagcca gcagcagata    9060
gggtgggagc agcatctcga gtatattaaa gcagaacttg tttattgcag cttataatgg    9120
ttacaaataa agcaatagca tcacaaattt cacaaataaa gcattttttt cactgcattc    9180
tagttgtggt ttgtccaaac tcatcaatgt atcttatcat gtctggtcga ctctagagct    9240
aagcaagtat gcaaaatgca gtgctgcttc gcattgggaa atccccaatc tggtgccaag    9300
aggttcataa atacagtaat ggaccctctt atgtcaaaag tgagtactgt ttaacagcgt    9360
aagttggaac agccttcagg atgctttgca gctgcagttg ttccactgca agacatcaca    9420
aacttcatga tgatggttgt cacaccaggt cctggaaagg caacctactt cagtctgcaa    9480
agtgaactaa aagggaatgg ttgttcatac atggccctga tgccactgac ataagaaacg    9540
caatgacaag agcgatgaag taggaatttg gtggcagatg gtcaggtctg caggaagtgt    9600
ccacccagct ttgtttggcc catattctga acaactaga ataaacactt agtgtcataa    9660
tttataagca tatcagtacc aataaatcag aatcatgcaa acagtcatgt ttattatatt    9720
cttgttgctt aatattcatg acagtaattt attttttatag tacagtttta ctgttctctc    9780
caccattgct ctctgcattt aaggctggca agttgtacta gcagaagttc aggtaaccct    9840
ttgaagactg caaaattcat tagcctggtc aaaagacttg atttgctcat ttaattttttc    9900 cctttttctc tcataaactt ttaagccact gagatgaaat ttctggaaac taagtagtaa    9960
taatacttct tcgacttgta gaaaatgtga atactagagt ccacctagtc ctctggtagt    10020
agctgtataa cagcgaattc ggcgtaatca tggtcatagc tgtttcctgt gtgaaattgt    10080
tatccgctca caattccaca caacatacga gccggaagca taaagtgtaa agcctggggt    10140
gcctaatgag tgagctaact cacattaatt gcgttgcgct cactgcccgc tttccagtcg    10200
ggaaacctgt cgtgccagct gcattaatga atcggccaac gcgcggggag aggcggtttg    10260
cgtattgggc gctcttccgc ttcctcgctc actgactcgc tgcgctcggt cgttcggctg    10320
cggcgagcgg tatcagctca ctcaaaggcg gtaatacggt tatccacaga atcaggggat    10380
aacgcaggaa agaacatgtg agcaaaaggc cagcaaaagg ccaggaaccg taaaaaggcc    10440
gcgttgctgg cgttttttcca taggctccgc cccctgacg agcatcacaa aaatcgacgc    10500
tcaagtcaga ggtggcgaaa cccgacagga ctataaagat accaggcgtt tccccctgga    10560
agctccctcg tgcgctctcc tgttccgacc ctgccgctta ccggatacct gtccgccttt    10620
ctcccttcgg gaagcgtggc gctttctcaa tgctcacgct gtaggtatct cagttcggtg    10680
taggtcgttc gctccaagct gggctgtgtg cacgaacccc ccgttcagcc cgaccgctgc    10740
```

```
gccttatccg gtaactatcg tcttgagtcc aacccggtaa gacacgactt atcgccactg    10800
gcagcagcca ctggtaacag gattagcaga gcgaggtatg taggcggtgc tacagagttc    10860
ttgaagtggt ggcctaacta cggctacact agaaggacag tatttggtat ctgcgctctg    10920
ctgaagccag ttaccttcgg aaaaagagtt ggtagctctt gatccggcaa acaaaccacc    10980
gctggtagcg gtggtttttt tgtttgcaag cagcagatta cgcgcagaaa aaaggatct     11040 caagaagatc ctttgatctt ttctacgggg tctgacgctc agtggaacga aaactcacgt    11100
taagggattt tggtcatgag attatcaaaa aggatcttca cctagatcct tttaaattaa    11160
aaatgaagtt ttaaatcaat ctaaagtata tatgagtaaa cttggtctga cagttaccaa    11220
tgcttaatca gtgaggcacc tatctcagcg atctgtctat ttcgttcatc catagttgcc    11280
tgactccccg tcgtgtagat aactacgata cgggagggct taccatctgg ccccagtgct    11340
gcaatgatac cgcgagaccc acgctcaccg gctccagatt tatcagcaat aaaccagcca    11400
gccggaaggg ccgagcgcag aagtggtcct gcaactttat ccgcctccat ccagtctatt    11460
aattgttgcc gggaagctag agtaagtagt tcgccagtta atagtttgcg caacgttgtt    11520
gccattgcta caggcatcgt ggtgtcacgc tcgtcgtttg gtatggcttc attcagctcc    11580
ggttcccaac gatcaaggcg agttacatga tcccccatgt tgtgcaaaaa agcggttagc    11640
tccttcggtc ctccgatcgt tgtcagaagt aagttggccg cagtgttatc actcatggtt    11700
atggcagcac tgcataattc tcttactgtc atgccatccg taagatgctt ttctgtgact    11760
ggtgagtact caaccaagtc attctgagaa tagtgtatgc ggcgaccgag ttgctcttgc    11820
ccggcgtcaa tacgggataa taccgcgcca catagcagaa ctttaaaagt gctcatcatt    11880
ggaaaacgtt cttcggggcg aaaactctca aggatcttac cgctgttgag atccagttcg    11940
atgtaaccca ctcgtgcacc caactgatct tcagcatctt ttactttcac cagcgtttct    12000
gggtgagcaa aaacaggaag gcaaaatgcc gcaaaaaagg gaataagggc gacacggaaa    12060
tgttgaatac tcatactctt ccttttcaa tattattgaa gcatttatca gggttattgt     12120
ctcatgagcg gatacatatt tgaatgtatt tagaaaaata aacaataggg gttccgcgc     12180 acatttcccc gaaaagtgcc acctgacgtc taagaaacca ttattatcat gacattaacc    12240
tataaaaata ggcgtatcac gaggcccttt cgtctcgcgc gtttcggtga tgacggtgaa    12300
aacctctgac acatgcagct cccggagacg gtcacagctt gtctgtaagc ggatgccggg    12360
agcagacaag cccgtcaggg cgcgtcagcg ggtgttggcg ggtgtcgggg ctggcttaac    12420
tatgc                                                                12425
```

<210> SEQ ID NO 34
<211> LENGTH: 20
<212> TYPE: DNA
<213> ORGANISM: Human immunodeficiency virus

<400> SEQUENCE: 34
accggtctac atagtctcta                                                20

<210> SEQ ID NO 35
<211> LENGTH: 17
<212> TYPE: DNA
<213> ORGANISM: Human immunodeficiency virus

<400> SEQUENCE: 35
tacaaccatc ccttcag                                                   17

-continued

```
<210> SEQ ID NO 36
<211> LENGTH: 18
<212> TYPE: DNA
<213> ORGANISM: Human immunodeficiency virus

<400> SEQUENCE: 36
atggaagaag agatccgc                                                 18

<210> SEQ ID NO 37
<211> LENGTH: 18
<212> TYPE: DNA
<213> ORGANISM: Human immunodeficiency virus

<400> SEQUENCE: 37
cctcgtagat gggcaccg                                                 18
```

DNA VECTORS CONTAINING MUTATED HIV PROVIRUSES

RELATED CASE INFORMATION

The present invention claims priority to U.S. Provisional Application No. 60/242,589, filed Oct. 23, 2000 entitled: DNA Vectors Containing Mutated HIV Proviruses and U.S. Provisional Application No. 60/253,432, filed Nov. 28, 2000 entitled: DNA Vectors Containing Mutated HIV Proviruses.

GOVERNMENT SUPPORT

Work described herein was supported by one or more of Grants Nos. AI41365, AI34757 AI-85343 and RR00168 from the National Institutes of Health and Contract No. NO1-CO-56000 awarded by the National Cancer Institute of NIH. The U.S. Government has certain rights in the inventions pursuant to this funding.

BACKGROUND OF THE INVENTION

The technical field of the invention is molecular biology and, in particular, vectors producing non-infectious particles that can be used to induce viral specific immune system responses.

Human immunodeficiency virus (HIV), the virus which causes acquired immune deficiency syndrome (AIDS), is a member of the retrovirus family. In particular, the HIV virus belongs to the lentivirus subfamily of retroviruses. The HIV virus contains two strands of single-stranded genomic ribonucleic acid (RNA) associated with two molecules of reverse transcriptase, an enzyme that catalyzes the process of "reverse transcription" to transcribe genomic RNA into double-stranded DNA. HIV also contains other nucleoid proteins, such as a protease enzyme and an integrase enzyme. The HIV genome, including the nucleoid proteins, is surrounded by a viral coat, known as the nucleocapsid, which consists of two layers of proteins. The HIV genome is further surrounded by an outer envelope coat, which is derived from the membrane of the host-cell.

The single-stranded RNA of the HIV genome encodes three different categories of proteins: the structural proteins encoded by the gag, pol and env genes; the regulatory proteins encoded by the tat and rev genes; and the accessory proteins encoded by the vpu, vpr, vif and nef genes. The HIV genome also has a repeated sequence, known as the long terminal repeat (LTR), at both the 5' and the 3' end of the genome. The 5' LTR contains enhancer and promoter sequences that are necessary for viral transcription, while the 3' LTR sequence is required for polyadenylating the transcripts that are created from the RNA genome. (Kuby, J., *Immunology*, $3^{rd}$ ed. (W. H Freeman and Company (1997)).

Numerous studies have investigated the role of these different proteins, in particular, the role of the structural proteins encoded by the gag and pol genes. To date, attempts have focused on separately mutating proteins such as the reverse transcriptase (RT), integrase (In) and nucleocapsid (NC) in order to characterize and modify their function. (See e.g. Kim, et al., *J. Biol. Chem.*, 271:4872–4878 (1996); Winters et al., *J. Virol.* 74:10707–10713 (2000); Lins et al., *Biophys. J.* 76:2999–3011 (1999); Ellison et al., *J. Biol. Chem.* 270:3320–3326 (1995); Zheng et al., *Proc. Natl. Acad. Sci.* 93:13659–13664 (1996); Leavitt et al., *J. Virol.* 70:721–728 (1996); Tanchou et al., *J. Virol.* 72:4442–4447 (1998); Druillennec et al., *J. Biol. Chem.* 274:11283–11288 (1999); and Schwartz et al., *J. Virol.* 71:9295–9305 (1997)).

In addition, attempts have been made to produce non-infectious virus particles, in particular by targeting the nucleocapsid protein. (See Aldovini et al., *J. Virol.* 64:1920–1926 (1990) and Poon et al., *J. Virol.* 70:6607–6616 (1996)). In U.S. Pat. No. 5,919,458, Aldovini et al., describes one approach to the construction of non-infectious HIV particles. This approach involves generating nucleotide alterations in the cis-acting RNA packaging site, also known as the $\Psi$ site, and in the cysteine rich carboxy-terminal region of the gag gene, to create HIV mutants that were defective for RNA packaging. Another approach to constructing non-infectious HIV particles is described by Poon et al., *J. Virol.* 70:6607–6616, (1996). In this study, non-infectious particles were created by altering the nucleocapsid structure to preclude viral RNA incorporation. However, these studies relied on generating deletion mutants of the NC domain in which entire structural domains of the NC were removed in order to prevent recombination to wild-type HIV. As a consequence, the alteration in the protein structure of the HIV virus prevents the virion from acting as a suitable antigen to elicit an immune response. Furthermore, there still remained the concern for reversion to wild-type virus and the generation of infectious particles.

There is also an interest in the development of vaccines to HIV to protect against, or at least retard the progression of, AIDS. The potential efficacy of such vaccines has been suggested by studies in the simian AIDS model systems and in limited human trials. Challenging the patient with either an attenuated or inactivated whole virion confers some immunity. Studies have shown that vaccines composed of whole, inactivated virions of simian immunodeficiency virus (SIV) confer at least partial protection against challenge with live virus. (See eg., Langlois et al., *Secience* 255: 292–293 (1992); Le Grand et al., *Nature* 355:684 (1992); Osterhaus et al., ibid., pp. 684–685; Cranage et al., ibid., pp. 685–686).

Production of inactivated HIV vaccines involves physical and chemical inactivation treatments necessary to render a non-infectious particle. However, such treatments can result in loss of immunogenicity due to partial destruction of the virions, thereby limiting the effectiveness of the immune response. A method that leaves virion structures intact, yet renders the virions non-infectious, would be a significant improvement in vaccine development.

One approach is the use of a DNA vaccine where the subject is inoculated with DNA molecules carrying a gene that encodes for a defective virion. DNA vaccines have a number of potential advantages over more conventional vaccine formulations. For example, multiple antigens can be expressed from a single DNA construct. In addition, because DNA vaccines express antigens in their native form, both humoral and cellular responses from the immune system are expected to be observed. Of particular importance is the generation of mucosal immunity because the major entry route for these retroviruses is typically through an orifice, which is lined with mucosa.

Accordingly, a need exists for producing a non-infectious virion which retains structural integrity in order to elicit an immune response, while preventing reversion to the wild-type virus. A need also exists for a DNA vaccine comprising a non-infectious virions capable of eliciting appropriate immune response in a subject without the risk of causing infection. A need also exists for DNA vaccines that can be specifically targeted to cells lining the passageways of the body.

SUMMARY OF THE INVENTION

The present invention is based on the discovery that several combinations of point mutations to the wild-type HIV genome can be employed to create composite safeguards in the production of non-infectious HIV particles and reduce or eliminate reversion to wild-type virus. The mutations also ensure that the non-infectious particles retain the ability to elicit an immune response in a subject. The mutations taught herein target various steps in the HIV replication cycle to produce non-infectious HIV particles. The steps of the HIV replication cycle typically include the binding of a mature HIV virion to the host cell membrane, the reverse transcription of the viral RNA to create double-stranded DNA and the incorporation of this double-stranded DNA into the genome of the host cell. Once the viral genome has been integrated into the host cell genome, the host cell's own cell machinery transcribes the HIV genes along with the host cell's own genes, thereby producing the viral proteins that will assemble into mature, infectious HIV particles. The invention targets each of these independent steps to provide a construct with mutations in proteins associated with each step, resulting in a non-infectious particle that retains the necessary structural features required to elicit the desired immune response, yet is unable to revert to a wild-type virus and cause infection. These mutations are designed to create a composite safety net, diminishing the possibility of generating an infectious particle, while retaining the basic protein content and immunogenic properties of a wild-type HIV virion.

Because replication of the HIV virus requires a mature virion to recognize and bind to the target host cell, mutating the NC protein so as to prevent the viral RNA from packaging into a mature genome will preclude the production of a mature virion. If the viral RNA were to package and form a mature genome, mutations in the RT protein that prevent the reverse transcription and the synthesis of double-stranded DNA would produce a HIV particle that is incapable of integrating into the genome of the host cell, and thus, non-infectious. If a double-stranded DNA copy of the viral genome were produced, mutations in the In protein that would prevent viral DNA from infiltrating the genome of a host cell would prevent the HIV genome from being transcribed and translated by the host cell's own cell mechanisms, thereby rendering the particle non-infectious. Thus, the novel combination of these mutations yields numerous safety precautions that will ensure the production of non-infectious, non-replicating HIV particles.

The present invention pertains to a nucleic acid construct capable of producing human immunodeficiency virus particles that can be used to elicit immune responses without causing viral infection. In particular, these mutations are made in one or more distinct regions of the viral genome, such as the NC encoding region, the RT encoding region and the In encoding region. These mutations are designed to alter the functionality of the nucleocapsid protein, the reverse transcriptase protein and the integrase protein, while preserving the tertiary (or quarternary) structure of each protein. The mutated HIV genome expresses mutant NC, RT and In proteins that can assemble into non-infectious particles which contain immunogenic components of the virus, but which are unable to infect cells. These mutations allow the production of non-infectious, immunogenic particles and provide a means for obtaining vaccines and other diagnostic reagents based on particles that are immunogenic, but not infectious.

In one aspect of the present invention, two or more mutations are made in a wild-type HIV genome. The preferred mutations are introduced in at least one amino acid position of the NC protein in combination with at least one other mutation in an amino acid position of the RT protein or the In protein. In one embodiment, the mutations to the native HIV genome may also be made in at least one amino acid position of the NC protein, at least one position in the RT protein, and at least one position in the In protein. In another embodiment, the mutations to the native HIV genome may be introduced in clusters, where two or more mutations are made in the NC protein, the RT protein, the In protein, or any combinations thereof.

In another aspect of the present invention, the mutated HIV construct is transfected into a mammalian cell line to produce mutant, non-infectious, non-replicating HIV particles.

In yet another aspect, the mutated HIV construct is used as a vaccine to generate an immune response, eg. a mucosal or systemic immune response in a subject. These non-infectious viral particles provide an alternative and advantageous method for the preparation of a whole virus vaccines. Such vaccines can be used to induce an anti-HIV response in an individual, either prior to or after infection with HIV, resulting in enhanced resistance by the individual to the virus.

DETAILED DESCRIPTION

Figure 1:
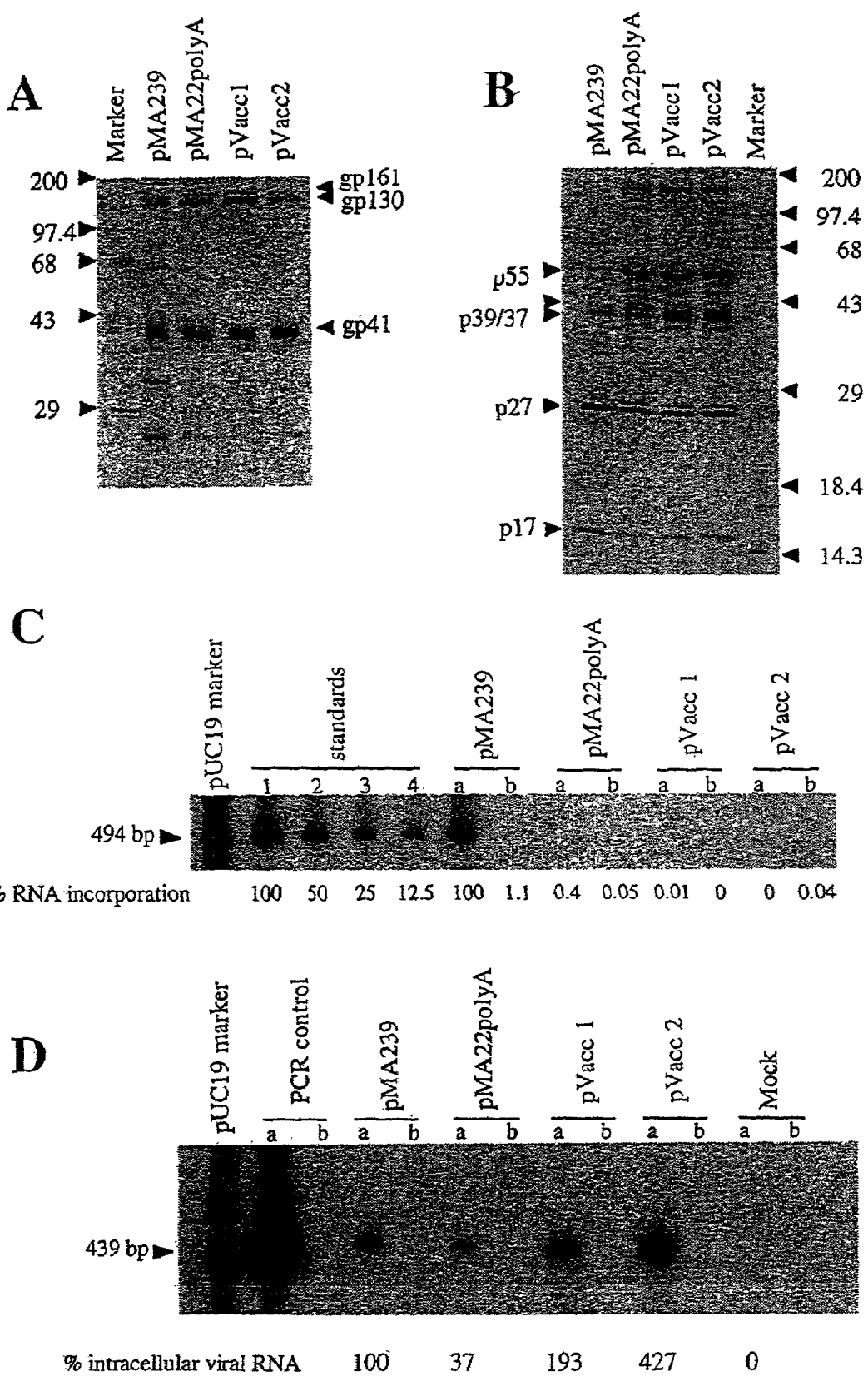
FIG. 1A is a photograph of a Western blot of viral particle production by SIV mutated constructs upon transfection into 293T cells. The blot was probed with a macaque SIV polyclonal serum that reacts predominantly with the SIV Env products.
FIG. 1B is a photograph of a Western blot of viral particle production by SIV mutated constructs upon transfection into 293T cells. The blot was probed with a macaque SIV polyclonal serum that reacts predominantly with the SIV Gag products.
FIG. 1C is a photograph of an agarose gel displaying RT-PCR analysis of the genomic RNA content of SIV mutated particles. RNA amplification was carried out with SIV gag-related primers on viral RNA extracted from pelleted virions. Lanes a and b are respectively RT-PCR and PCR reactions carried out on the RNA samples.
FIG. 1D is a photograph of an agarose gel displaying RT-PCR analysis of total viral RNA accumulated intracellularly 48 hours after transfection with SIV constructs. Nucleic acid amplification was carried out with SIV tat-related primers on total cellular RNA extracted from transfected 239T cells. Lanes a and b are RT-PCR (a) and PCR (b) reactions carried out on the total cellular RNA samples.

So that the invention is more clearly understood, the following terms are defined:

The term "HIV," as used herein, refers to all strains and permutations of HIV. The term HIV can include, but is not limited to HIV-1 and HIV-2.

The term "mutation," as used herein, refers to any alteration of the gag and/or pol gene that inactivates the functionality of the protein produced by that gene. Such mutations can include, but are not limited to, an amino acid substitution wherein a native amino acid is replaced with an alanine or other biologically comparable amino acid residue, including, but not limited to glycine, valine, and leucine, or a deletion of any portion of the gag and/or pol gene.

The term "portion" or "fragment" as used herein refers to an amino acid sequence of the gag or pol genes that has fewer amino acids than the entire sequence of the gag and/or pol genes.

The term "cluster" or "cluster of mutations" as used herein refers to any mutations made in two or more residues that are located within three, five, seven, nine or eleven amino acid positions of each other. Preferably, cluster refers to two or more mutations within seven amino acids. Cluster can also refer to mutations made within 1 amino acid residue upstream or downstream of the site-specific mutation or within 2 amino acid residues upstream or downstream of the site-specific mutation.

The term "coding sequence" or a sequence which "encodes" or sequence "encoding" a particular protein, as used herein refers to a nucleic acid molecule which is transcribed (in the case of DNA) and translated (in the case of messenger mRNA) into a polypeptide in vitro or in vivo when placed under the control of appropriate regulatory sequences The terms "5'", "3'", "upstream" or "downstream" are art-recognized terms that describe the relative position of nucleotide sequences in a particular nucleic acid molecule relative to another sequence.

The term "promoter" is used herein refers to the art recognized use of the term of a nucleotide region comprising a regulatory sequence, wherein the regulatory sequence is derived from a gene which is capable of binding RNA polymerase and initiating transcription of a downstream (3'-direction) coding sequence.

The term "regulatory sequence" is art-recognized and intended to include control elements such as promoters, enhancers and other expression control elements (e.g., polyadenylation signals), transcription termination sequences, upstream regulatory domains, origins of replication, internal ribosome entry sites ("IRES"), enhancers, enhancer sequences, post-regulatory sequences and the like, which collectively provide for the replication, transcription and translation of a coding sequence in a recipient cell. Not all of these regulatory sequences need always be present so long as the selected coding sequence is capable of being replicated, transcribed and translated in an appropriate host cell. Such regulatory sequences are known to those skilled in the art and are described in Goeddel, *Gene Expression Technology: Methods in Enzymology* 185, Academic Press, San Diego, Calif. (1990), the teachings of which are herein incorporated in their entirety by reference. It should be understood that the design of the viral vector may depend on such factors as the choice of the host cell to be transfected and/or the amount of protein to be expressed.

The term "operably linked" as used herein refers to an arrangement of elements wherein the components are configured so as to perform their usual function. Thus, control elements operably linked to a coding sequence are capable of effecting the expression of the coding sequence. The control elements need not be contiguous with the coding sequence, so long as they function to direct the expression of the coding sequence. For example, intervening untranslated yet transcribed can be present between a promoter sequence and the coding sequence and the promoter sequence can still be considered "operably linked" to the coding sequence.

The term "transfection" is used herein refers to the uptake of an exogenous nucleic acid molecule by a cell. A cell has been "transfected" when exogenous nucleic acid has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197, the teachings of which are herein incorporated in their entirety by reference. Such techniques can be used to introduce one or more exogenous nucleic acid molecules into suitable host cells. The term refers to both stable and transient uptake of the nucleic acid molecule.

The term "gene transfer" or "gene delivery" as used herein refers to methods or systems for reliably inserting foreign DNA into host cells. Such methods can result in transient expression of non-integrated transferred DNA, extra-chromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. (See, e.g., U.S. Pat. No. 5,399,346, the teachings of which are herein incorporated in their entirety by reference).

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The terms "polypeptide" and "protein" are used interchangeably herein and refer to a polymer of amino acids and includes full-length proteins and fragments thereof. As will be appreciated by those skilled in the art, the invention also includes nucleic acids that encode those polypeptides having slight variations in amino acid sequences or other properties from a known amino acid sequence. Amino acid substitutions can be selected by known parameters to be neutral and can be introduced into the nucleic acid sequence encoding it by standard methods such as induced point, deletion, insertion and substitution mutants. Minor changes in amino acid sequence are generally preferred, such as conservative amino acid replacements, small internal deletions or insertions, and additions or deletions at the ends of the molecules. These modifications can result in changes in the amino acid sequence, provide silent mutations, modify a restriction site, or provide other specific mutations. Additionally, they can result in a beneficial change to the encoded protein.

The term "homology" or "identity" as used herein refers to the percentage of likeness between nucleic acid molecules or protein molecules, including codon-optimized nucleic acid molecules. To determine the homology or percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) *J. Mol. Biol.* (48):444–453, the teachings of which are herein incorporated in their entirety by reference) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In another example, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In yet another example, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty.

The present invention pertains to the introduction of a number of inactivating mutations into a viral genome of an immunodeficiency virus. The viral genome can be that of HIV. All strains and permutations of HIV are within the scope of this invention, for example HIV-1 and HIV-2. The accession numbers of HIV-1 and HIV-2 are NC001802 and NC001722, respectively, and are available from the NCBI database. Moreover, molecular clones of the HIV virus, including, but not limited to, HXB2 are within the scope of this invention. The nucleotide sequence of HXB2 is shown in SEQ ID NO: 1, and the amino acid sequence of HXB2 is shown in SEQ ID NO: 2. Different genetic regions within the HXB2 that are particularly important in the present invention include the reverse RT gene, the In gene, and the NC gene. The nucleotide sequence of the RT gene is shown in SEQ ID NO: 3, and the amino acid sequence of RT is shown in SEQ ID NO: 4. The nucleotide sequence of the In gene is shown in SEQ ID NO: 5, and the amino acid sequence of In is shown in SEQ ID NO: 6. The nucleotide sequence of the NC gene is shown in SEQ ID NO: 7, and the amino acid sequence of NC is shown in SEQ ID NO: 8. The nucleotide sequence of gag gene is SEQ ID NO: 9 and the amino acid sequence is SEQ ID NO: 10. The amino acid sequence of molecular clones like HXB2 can be obtained from a database, e.g., NCBI, and the actual clone from the NIH AIDS Research and Reference Reagent Program Catalog.

The mutated viral genome of the invention is used to transfect a host cell. Once inside the host cell, the viral genome can undergo cellular processing, including transcription. The expressed mutated and wild-type viral proteins are used to assemble a defective (non-infectious) viral particles (also known as virions). These mutated (or defective) viral particles have a protein content that is similar to the wild-type (or native) virion, thus the defective viral particle retains immunogenic properties similar to wild-type virions.

Further details of the invention are described in the following sections:

I. The Nucleocapsid, Reverse Transcriptase, and Integrase Proteins of HIV

The present invention provides a novel combination of mutations to the wild-type HIV genome that create numerous safety precautions to ensure the production of non-infectious HIV particles. The mutations taught herein target various steps in the HIV replication cycle that are catalyzed or controlled by the NC, RT and In proteins. These mutation sites are conservative sites found throughout the various strains of HIV.

In one embodiment of the instant invention, mutant HIV viruses are disclosed wherein at least two independent genes are mutated. In this embodiment, at least one mutation is made in the NC gene and one or more mutations also occurs in the RT gene and/or the In gene. This HIV construct is capable of eliciting an immune response in an inoculated host, thereby providing immunological protection against the HIV virus. In one aspect of the current invention, immunity is specifically elicited by the introduction of a mutated HIV construct into different tissues. In a preferable embodiment, one or more mutations occurs in all three genes encoding the NC, RT and In proteins. These genes can be mutated by site directed mutagenesis.

Some amino acid residues that appear to be important to the function of NC, RT and In have been characterized. (See Ellison et al., *J. Biol. Chem.* 270:3320–3326 (1995); Kim et al., *J. Biol. Chem.* 271:4872–4878 (1996), the teachings of which are incorporated herein in their entirety by reference). Some of these amino acid residues were chosen as mutation sites because they retain the tertiary (or quaternary) structure of the mutated protein so that it resembles the wild-type protein with respect to immunogenic properties. It is not sufficient that the mutated protein has immunogenicity itself, it must have the same or similar immunogenic properties as found in the wild-type protein in order to elicit the desired immune response. In addition, amino acid residues selected for site specific mutation were those that would prevent viral RNA packaging, as well as disrupting RT and In function.

Accordingly, the present invention targets regions in the nucleocapsid p7 protein (NCp7), the p66/p51 reverse transcriptase protein (RT) and the p32 integrase protein (In). The region of the gag gene that encodes the NCp7 has been targeted, because NCp7 is known to play a significant role in the creation of mature virus particles. NCp7 has been shown to be responsible for the packaging of viral RNA in the HIV virus. According to these studies, packaging of retroviral RNA requires an interaction between the NCp7 domain of the Gag polypeptide precursor and the RNA packaging site (also referred to as the Ψ-site), located in the HIV genome between the 5' LTR and the gag initiation codon. (See Aldovini et al., *J. Virol.* 64:1920–1926 (1990); Poon et al., J. Virol 70: 6607–6616 (1996), the teachings of which are herein incorporated in their entirety by reference).

For the purposes of the invention, the NCp7 has been divided into five regions, which include the 5' flanking region (amino acids 1–14), the first zinc finger domain, also known as the 5' Cys-His box (residues 15–28 of SEQ ID NO: 8), the basic amino acid linking region (residues 29–35 of SEQ ID NO: 8), the second zinc finger, also known the 3' Cys-His box (residues 36–49 of SEQ ID NO: 8) and the 3' flanking region (residues 50–55 of SEQ ID NO: 8). The two, highly conserved Cys-His boxes, which take the form of $CX_2CX_4HX_4C$, are in well-defined spatial proximity, while the N-terminal and C-terminal sequences remain flexible. (Druillennec et al., *Proc. Natl. Acad. Sci.* 96:4886–4891 (1999), the teachings of which are herein incorporated in their entirety by reference). The NCp7 protein has been found to interact with the reverse transcriptase protein to form a 1:1 complex. These studies have shown that the 5' and 3' Cys-His boxes, and the linking region, are necessary for reverse transcriptase binding. Alterations in these domains prevent the formation of the NCp7-reverse transcriptase complex. (Druillennec et al., *J. Biol. Chem.* 274:11283–11288 (1999), the teachings of which are herein incorporated in their entirety by reference).

A previous study by the present inventor and others found that mutations in the NCp7 domain of the gag precursor polypeptide reduced the efficiency of RNA packaging in the HIV virus. (Poon, et al. *J. Virol.* 70:6607–6616 (1996), the teachings of which are incorporated herein in their entirety by reference). In this study, the highly basic NCp7 protein was mutated using an alanine amino acid to replace various positively-charged amino acid residues. The positively-charged amino acid residues of the NCp7 protein include five amino acid residues in the N-terminal region (arginine 3, arginine 7, arginine 10, lysine 11 and lysine 14), three amino acid residues in the 5' Cys-His box (lysine 20, histidine 23 and arginine 26), four amino acid residues in the linking region (arginine 29, arginine 32, lysine 33 and lysine 34), four amino acid residues in the 3' Cys-His box (lysine 38, lysine 41, histidine 44 and lysine 47), and one amino acid residue in the C-terminal region (arginine 52). The twenty-eight mutants studied by Poon et al. included single mutations at each of the basic amino acid positions, as well as "clusters" of mutations within the regions, and combinations thereof. Clusters has been defined as mutations in two or more amino acid residues that are located within three, five, seven, nine or eleven amino acid positions of each other. (See Table 1).

TABLE 1

Mutations in the NCp7 protein

| Sequence: M Q R G N F R N Q R K I V K C F N C G K E G H T A R N C R A P R K K G C W K C G K E G H Q M K D C T E R Q A N | mutated a.a.# | construct name |
|---|---|---|
| Alanine scanning mutations aligned to sequence above | 3 | pR3 |
| | 7 | pR7 |
| | 10 | pR10 |
| | 11 | pK11 |
| | 14 | pK14 |
| | 20 | pK20 |
| | 23 | pH23 |
| | 26 | pR26 |
| | 29 | pR29 |
| | 32 | pR32 |
| | 33 | pK33 |
| | 34 | pK34 |
| | 38 | pK38 |
| | 41 | pK41 |
| | 44 | pH44 |
| | 47 | pK47 |
| | 52 | pR52 |
| | 14-20-26-29-32-33-34-38-41-47 | pM1-2/BR |
| | 14-20-26-38-41-47 | pM1-2 |
| | 14-20-26 | p14-20-16 |
| | 20-26 | p20-26 |
| | 38-41-47 | p38-41-47 |
| | 29-32-33-34 | pBR |
| | 29-33 | p29-33 |
| | 10-11-52 | p10-11-52 |
| | 10-11 | p10-11 |
| | 10-52 | p10-52 |
| | 11-52 | p11-52 |

Schematic representation of alanine scanning mutations within the HIV-1 NC p7 protein. The amino acid sequence of HIV-1 NC p7 is listed above the alanine substitutions for each mutant. The specific amino acid residue(s) (aa) modified in each mutant and the name of the corresponding plasmid construct are shown on the right.

The results of this study by Poon et al. show that several NCp7 mutants produced non-infectious HIV particles. Of the twenty-eight mutants studied, eleven were found to reduce or eliminate the infectivity of the resulting HIV mutant particles. (See Table 2, below). The results in Table 2 show two constructs (pR3 and pK14) in which single amino acid substitutions resulted in non-infectious particles. These mutants include two single amino acid mutations, one at arginine 3 and the other at position lysine 14, which immediately precedes the 5' Cys-His box. The other mutants that yielded non-infectious particles included clusters of mutations in the 5' flanking region, the 5' Cys-His box, in the basic amino acid linker region, and in the 3' Cys-His box, as well as combinations thereof. In addition to the mutations in the NC protein, the present invention combines mutations in the NC protein with mutations in the RT and/or the In proteins to provide additional safeguards for preventing reversion to an infectious virus.

TABLE 2

Effects of alanine substitutions in NC p7 on viral genomic RNA incorporation and infectivity*

| Construct | RNA incorporation (% of wt) | Infectivity | Group |
|---|---|---|---|
| pHXB2gpt | 100 | +++ | A |
| pR3 | 81.63 + 11.46 | − | C |
| pR7 | 52.80 + 5.22 | + | B |
| pR10 | 47.20 + 4.29 | + | B |
| pK11 | 24.90 + 3.13 | + | B |
| pK14 | 22.30 + 1.67 | − | C |
| pK38 | 63.90 + 2.58 | + | B |
| pK47 | 59.46 + 1.71 | + | B |
| pM1-2/BR | 0.33 + 0.33 | − | C |
| pM1-2 | 1.33 + 0.23 | − | C |
| p14-20-26 | 12.56 + 2.51 | − | C |
| p38-41-47 | 0.70 + 0.35 | − | C |
| pBR | 14.03 + 2.12 | − | C |
| p10-11-52 | 10.30 + 3.85 | − | C |
| p10-11 | 32.83 + 5.18 | − | C |
| p10-52 | 48.03 + 3.15 | + | B |
| p11-52 | 56.76 + 9.22 | + | B |

*Relative nucleic acid content of viral particles was measured by RT-PCR. RT-PCRs using gag-specific primers were carried out to detect viral genomic RNA incorporation. The average of values + standard error from three independent experiments is reported for each mutant. The infectivity group to which each mutant was assigned is also listed. wt, wild type.

Accordingly, in addition to the mutations in the NC protein, the present invention also targets the portion of the pol gene that encodes the integrase protein. The integrase enzyme is responsible for incorporating the viral DNA into the DNA of the host cell. Once the viral DNA has been inserted, the host cell's own transcription and translation mechanisms cause the cell to produce viral particles.

Formed from a single polypeptide chain, the integrase protein has three functional domains. These three domains consist of the N-terminal domain (residues 1–50 of SEQ ID NO: 6), the core region (residues 51–212 of SEQ ID NO: 6), and the C-terminal domain (residues 213–280 of SEQ ID NO: 6). (See e.g., Lins et al., *Biophys. J.* 76:2999–3011 (1999); Leavitt et al. *J. Virol.* 70:721–728 (1996); Ellison et al., *J. Biol. Chem.* 270:3320–3326 (1995); Zheng et al., *Proc. Natl. Acad. Sci.* 93:13659–13664 (1996), the teachings of which are incorporated herein in their entirety by reference).

The N-terminal domain of integrase contains a pair of highly conserved His and Cys residues, also known as the HHCC motif, which has been found to bind zinc with a stoichiometry of one zinc ion per integrase protein. (Zheng et al., *Proc. Natl. Acad. Sci.*, 93:13659–13664 (1996), the teachings of which are herein incorporated in their entirety by reference). Studies have shown that mutations in the HHCC domain affect the ability of integrase to bind zinc ions, which in turn affects the catalytic activity of the integrase enzyme. (See e.g., Ellison et al., *J. Biol. Chem.* 270:3320–3326 (1995); Zheng et al., *Proc. Natl. Acad. Sci.*, 93:13659–13664 (1996), the teachings of which are herein incorporated in their entirety by reference). When the integrase protein binds a zinc ion, its catalytic reaction rate is between 5- and 15-fold greater than an integrase enzyme that contains no zinc. (Zheng et al., *Proc. Natl. Acad. Sci.*, 93:13659–13664 (1996), the teachings of which are herein incorporated in their entirety by reference).

The core domain of the integrase protein contains the highly conserved amino acid sequence of two aspartic acid residues followed by a glutamic acid residue (commonly referred to as the D,D35E motif), with a conserved spacing of 35 residues between the second and third acidic residues. These D,D35E residues (aspartic acid 66, aspartic acid 118 and glutamic acid 154) are commonly called the catalytic triad, because they form the active site of the catalytic domain. (Lins et al. *Biophys. J.*, 76:2999–3011 (1999), the teachings of which are herein incorporated in their entirety by reference). Mutations at each of these residues impairs the ability of the HIV virus to integrate into a host cell and form a provirus. (Leavitt, et al., *J. Virol.* 70:721–728 (1996), the teachings of which are incorporated in their entirety by reference).

The present invention also targets the region of the pol gene that encodes for the reverse transcriptase protein. Reverse transcriptase is formed by cleaving the Gag-Pol polypeptide precursor to produce a homodimer of two p66 molecules. Initially, each p66 molecule contains a polymerase and an RNase H domain, but the RNase H domain of one subunit is subsequently removed to create a p66-p51 reverse transcriptase heterodimer. The polymerase domain of the reverse transcriptase protein consists of four subdomains, commonly referred to as the "fingers," "palm," "thumb" and "connection" regions. The "fingers" region (residues 1–84 and 120–150 of SEQ ID NO: 4) contains mixed β-strands and three α-helices. In particular, the β3–β4 loop encodes for amino acids 67–78 of the reverse transcriptase protein. The five β-strands of the "palm" region (residues 85–119 and 151–243 of SEQ ID NO: 4) interact and form hydrogen bonds with the four β-strands of the "thumb" region (residues 244–322 of SEQ ID NO: 4). The "connection" subdomain (residues 323–437 of SEQ ID NO: 4), which connects the polymerase and RNase H domains, is composed of a large β-sheet and two α-helices. Studies have shown that the residues of the "fingers," "palm" and "thumb" subdomains form the majority of RT-DNA contacts when the enzyme binds to DNA. (Turner et al., *J. Mol. Biol.* 285:1–32 (1999), the teachings of which are herein incorporated in their entirety by reference).

While the polymerase subdomains of the p51 and p66 have identical amino acid sequences, the packaging of the subdomains found within each molecule is drastically different. In the p66 molecule, the subdomains of the polymerase region pack together to form a configuration, commonly referred to as an "open-right hand," in which the three catalytic residues, aspartic acid 110, aspartic acid 185 and aspartic acid 186, are exposed. The subdomains of the p51 molecule, however, are packaged so that the "fingers" close over the "palm" region and, thus, cover the catalytic residues. Consequently, p51 is a catalytically inactive molecule.

(Turner et al., *J. Mol. Biol.* 285:1–32 (1999), the teachings of which are herein incorporated in their entirety by reference).

Other regions of the HIV genome can also be mutated in combination with the mutations made in the NC, RT and/or In genes. For example, the nucleotide sequence coding for the long terminal repeats (LTR) can be mutated. (See e.g., U.S. Pat. Nos. 5,912,338, 5,439,809, 5,866,320 & 5,889, 176, the entire teaching of which is incorporated herein by reference). These viral genes when mutated along with the RT and In gene provide for additional safety by minimizing the possibility of viral reversion.

Also within the scope of the invention is a construct that comprises an envelope gene, and variations thereof, in addition to one or more mutations in the NC, In and/or RT genes. The HIV envelope protein has been extensively described, and the amino acid and RNA sequences encoding HIV envelope from a number of HIV strains are known (Myers et al., 1992. Human Retroviruses and AIDS. A compilation and analysis of nucleic acid and amino acid sequences. Los Alamos National Laboratory, Los Alamos, N. Mex.). The envelope protein has hypervariable domains that have extensive amino acid substitutions, insertions and deletions. Sequence variations in these domains result in up to 30% overall sequence variability between envelope molecules from the various viral isolates.

In one embodiment of this invention, a mutated HIV genome is packaged into an appropriate plasmid vehicle. A host cell is then transfected using this mutated construct. Once the viral construct enters the host cell, the mutated viral genome can be transcribed and translated leading to mutated viral proteins that are able to assemble into a non-infectious viral particle.

II. Construction of the DNA Vaccine

The HIV construct comprising mutations in viral genes and regulatory elements can be used to produce a DNA vaccine. DNA vaccines have a number of demonstrated and potential advantages over more conventional vaccine formulations. Stimulation of both humoral and cellular responses is usually observed, as antigens are expressed in their native form and correctly presented to the immune system. These responses can involve MHC class I-restricted cytotoxic T-lymphocytes (CTLs), even in animal models that do not normally exhibit strong CTL responses to vaccination. Multiple antigens can also be expressed from a single vaccine construct. A variety of different routes and methods of immunization are available for DNA vaccination including subcutaneous, intradermal, intramuscular, nasal, vaginal and mucosal. DNA can be delivered in a liposome formulation by injection or by gene gun delivery. The DNA can be delivered in such a way as to generate a systemic response and a mucosal response at the same time. The DNA may be administered to generate a systemic response first, followed by a mucosal response. Because prolonged antigen stimulation can be achieved with DNA vaccination, it is possible that a single dose, or a limited number of doses of the vaccine will be adequate to achieve protection. DNA is a relatively stable molecule, facilitating storage and handling. Finally, the ease of manufacture, scale-up and distribution of DNA vaccines makes this technology very attractive. One example of an HIV DNA vaccine is the pVacc10 HIV DNA vaccine. The generation of the pVacc10 HIV construct is described in Example 1.

In one embodiment of the instant invention, a nucleic acid construct encodes mutant HIV particles that produce non-infectious HIV particles when expressed in mammalian cells or injected into primates. The construct has a number of mutations in the NC and RT and/or In genes of a wild-type HIV genome. Specifically, the nucleocapsid gene is mutated, such that the amino acid sequence of the encoded protein is altered, wherein the alteration occurs in at least one amino acid selected from the group consisting of lysine 14, lysine 20, arginine 26, arginine 29, arginine 32, lysine 33, lysine 34, lysine 38, lysine 41, lysine 47 and combinations thereof. Moreover, either the reverse transcriptase gene, or the integrase gene, or both is mutated, such that the amino acid sequence of the encoded protein is altered. Mutations of the reverse transcriptase gene that result in an alteration of the amino acid sequence of the encoded protein occur in at least one amino acid position selected from the group consisting of tryptophan 71, arginine 72, arginine 78 and combinations thereof. Mutations in the integrase gene that alter the amino acid sequence of the encoded protein occur in at least one amino acid selected from the group consisting of histidine 14, histidine 18, cysteine 42, cysteine 45, aspartic acid 66, aspartic acid 118, glutamic acid 154 and combinations thereof.

The nucleotide sequence of mutated RT is shown SEQ ID NO: 27 and the corresponding amino acid sequence of the mutated RT is shown in SEQ ID NO: 28 displaying the mutation at positions 71, 72 and 78. The nucleotide sequence of mutated In is shown in SEQ ID NO: 29 and the corresponding amino acid sequence of the mutated In is shown in SEQ ID NO: 30 displaying the mutation at positions 14, 18,42, 45, 66, 118 and 154. The nucleotide sequence of the mutated NC is shown in SEQ ID NO: 31 and the corresponding amino acid sequence of the mutated NC is shown in SEQ ID NO: 32 displaying the mutation at positions 14, 20,26, 29, 32, 33, 34, 38, 41, and 47. The nucleotide sequence of pVacc10 construct comprising all the mutations, as shown in SEQ ID NO: 33.

III. Recombinant Technologies

The instant invention relates to nucleic acid molecules encoding mutated HIV molecules. This invention relates to DNA constructs comprising a nucleic acid molecule encoding HIV proteins operatively linked to recombinant host cells. As appropriate, nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. The nucleotide sequence can include at least a fragment of the amino acid coding sequence along with additional noncoding sequences such as introns and non-coding 3' and 5' sequences (including regulatory sequences, for example). Additionally, the nucleotide sequence can be fused to a marker sequence, for example, a sequence which encodes a polypeptide to assist in isolation or purification of a viral protein(s). Such sequences include, but are not limited to, those which encode a glutathione-S-transferase (GST) fusion protein and those which encode a hemagglutin-A (HA) peptide marker for influenza. Various promoters have been engineered to drive expression of genes, such as the HIV genes, as different promoters might produce different levels of antigen in the various cells targeted by DNA vaccination. All constructs of the present invention contain multiple CpG motifs, which are associated with improved immunostimulatory properties of DNA vaccines. (Krieg, *Trends Microbiol.* 7:64–65 (1999), the teachings of which are incorporated herein in their entirety by reference).

The invention provides expression vectors containing a nucleic acid sequence encoding one or more viral proteins described herein. Many such vectors are commercially available, and other suitable vectors can be readily prepared by the skilled artisan. The invention also relates to expression vectors comprising the nucleic acid molecule encoding the virus which are transfected into host cells, such as bacterial cells, insect cells, yeast cells, avian cells, fungal cells, plant cells, insect cells and mammalian cells. It should be understood that the design of the expression vector may depend on such factors as the choice of the host cell to be transformed and/or the type of protein desired to be expressed. For instance, the proteins of the present invention can be produced by ligating the HIV nucleic acid sequence, or a portion thereof, into a suitable vector for expression in either prokaryotic cells, eukaryotic cells, or both. (See, for example, Broach, et al., *Experimental Manipulation of Gene Expression*, ed. M. Inouye (Academic Press, 1983) p. 83; *Molecular Cloning: A Laboratory Manual*, 2$^{nd}$ Ed., ed. Sambrook et al. (Cold Spring Harbor Laboratory Press, 1989) Chapters 16 and 17, the teachings of which are herein incorporated in their entirety by reference). Typically, expression vectors will contain one or more selectable markers, including, but not limited to, the gene that encodes dihydrofolate reductase and the genes that confer resistance to neomycin, tetracycline, ampicillin, chloramphenicol, kanamycin and streptomycin resistance.

Eukaryotic or prokaryotic host cells transfected by the described vectors are also provided by this invention. For instance, cells which can be transfected with the vectors of the present invention include, but are not limited to, mammalian cells, such as Chinese hamster ovary cells (CHO), COS cells, CEM leukemic lymphocytes, MCF-7 breast cancer cells, H9 and 293T cells.

Thus, a nucleotide sequence described herein can be used to produce a recombinant form of a viral protein via an eukaryotic cellular processes. Similar procedures, or modifications thereof, can be employed to prepare recombinant peptides according to the present invention by microbial means or tissue/cell culture technology. Accordingly, the invention pertains to the production of described peptides by recombinant technology.

The present invention pertains to the transfection of host cells with a mutated viral genome. There are several methods of transfection that one of ordinary skill in the art may employ. For example, transfection can be accomplished by calcium phosphate precipitation. In this method, a precipitate containing calcium phosphate and DNA is formed by slowly mixing a HEPES-buffered saline solution with a solution containing about 2.5 M calcium chloride and about 10 to 50 µg of DNA. This precipitate adheres to the surface of the host cell. The additional use of about 10% solution (vol/vol) of glycerol or dimethyl sulfoxide will increase the amount of DNA absorbed in some host cells. (Ausubel et al. (eds.), *Current Protocols in Molecular Biology*, Greene Publishing Associates and Wiley-Interscience, 5$^{th}$ ed., 1991), vol. 1, pp. 9.1.1–9.1.3, the teachings of which are herein incorporated in their entirety by reference).

Transfection may also be accomplished by electroporation of the host cell. Electroporation can be used for both transient and stable transfection. The host cell is placed in suspension and put into an electroporation cuvette and then the DNA is added. The cuvette is connected to a power supply, and the cells are subjected to a high-voltage pulse of defined magnitude and length, for example, shocks at 1 to 2 kV with a 3-µF capacitance is employed. The cell is then allowed to recover briefly before the media is changed.

(Ausubel, et al. (eds.), *Current Protocols in Molecular Biology*, Greene Publishing Associates and Wiley-Interscience, 5$^{th}$ ed., 1991), vol. 1, pp. 9.3.1–9.3.4, the teachings of which are herein incorporated in their entirety by reference). Both of these transfection methods, calcium precipitation and electroporation, are known to one skilled in the art.

Transfection may also be liposome-mediated. This method is well known to the skilled artisan. Generally, using liposomes to deliver DNA into different cell types results in higher efficiency and greater reproducibility than other transfection methods. Essentially, plasmid DNA derived from either crude (miniprep) or purified (through cesium chloride centrifugation) preparations is mixed with a commercially available liposome suspension comprising cationic lipids. The DNA-liposome complex is applied to approximately $5 \times 10^5$ cells/well and grown overnight in a $CO_2$ incubator at about 37° C. to around 80% confluency. after overnight incubation with the liposome-DNA complex, the cells can be harvested by scrapping, trypsinization, or freeze thaw methods as described by Ausubel et al. (eds.), *Current Protocols in Molecular Biology*, Greene Publishing Associates and Wiley-Interscience, 5$^{th}$ ed., 1991), vol. 1, pp. 9.4.1–9.4, the teachings of which are herein incorporated in their entirety by reference.

IV. Codon Optimization and Homology

Also included within the scope of the invention are conservative mutations. For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methoinine. (See e.g., Biochemistry, 2nd ed, Ed. by L. Stryer, W H Freeman and Co.: 1981).

DNA molecules that code for the viral peptides can easily be determined from the list of codons in Table 3, below. In fact, since there is a fixed relationship between DNA codons and amino acids in a peptide, any discussion in this application of a replacement or other change in a peptide is equally applicable to the corresponding DNA sequence or to the DNA molecule, recombinant vector, transformed microorganism, or transfected eukaryotic cells in which the sequence is located (and vice versa). An important and well known feature of the genetic code is its redundancy, whereby, for most of the amino acids used to make proteins, more than one coding nucleotide triplet may be employed. Therefore, a number of different nucleotide sequences may code for a given amino acid sequence. Such nucleotide sequences are considered functionally equivalent since they can result in the production of the same amino acid sequence in all organisms, although certain strains may translate some sequences more efficiently than they do others.

TABLE 3

The genetic code
GENETIC CODE

| | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp,D) | GAC, GAT |
| Cysteine (Cys, C) | TGC, TGT |
| Glutamic acid (Glu,E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe,F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

Key: Each 3-letter triplet represents a trinucleotide of DNA having a 5' end on the left and a 3' end on the right. The letters stand for the purine or pyrimidine bases forming the nucleotide sequence. A = adenine, G = guanine, C = cytosine, T = thymine Codons can be chosen for use in a particular host organism in accordance with the frequency with which a particular codon is utilized by that host, if desired, to increase the rate at which expression of the peptide occurs, a process known as "codon optimization." Codon bias has been observed in many species. The preferential use of codons for a given gene is positively correlated with its expression efficiency. Codons are DNA triplets that constitute "one information unit" for protein synthesis; 64 distinct triplet sequences exist. The 20 amino acids are encoded by 61 codons and the remaining 3 codons encode protein synthesis termination signals. Each codon is specific for a single amino acid. In most cases, however, a single amino acid, can be identified by more than one codon. Thus different DNA sequences can code for the same protein. Not all codons are used with the same frequency between species. Some codons are more commonly used while others are not. Codons which are "rare" usually correlate with a reduced intracellular level of aminoacyl-tRNAs, the biochemical building blocks used by ribosomes to match a codon with the correct amino-acid during protein synthesis. If a particular aminoacyl-tRNA is deficient, then use of the corresponding codon will slow the rate of protein synthesis and can decrease yield of a desired protein product. (See e.g., Sharp et al., *Nucleic Acids Res.*, 17:5029–39 (1989), the teachings of which are herein incorporated in their entirety by reference).

The relative frequency of use for each codon can vary significantly between species. Codon usage for a wide variety of organisms is cataloged by the National Institute of Health of Japan. Engineering a construct in which the codons have been optimized would result in a different DNA sequence that has been uniquely optimized for expression of the desired protein sequence in any host cell. Accordingly, nucleic acid constructs that have been codon optimized are intended to be within the scope of the invention.

The terms "codon optimization" and/or "codon optimized for humans" are used herein to encompass various synthetic gene sequences which encode proteins, such as the NC, RT and IN proteins of the non-infectious viral particles of the present invention, wherein at least one non-preferred or less preferred codon in the natural gene encoding the protein has been replaced by a preferred codon encoding the same amino acid.

For increased human expression the preferred codons can include one or more of the following: Ala (gcc); Arg (cgc); Asn (aac); Asp (gac) Cys (tgc); Gln (cag); Gly (ggc); His (cac); Ile (atc); Leu (ctg); Lys (aag); Pro (ccc); Phe (ttc); Ser (agc); Thr (acc); Tyr (tac); and Val (gtg). Less preferred codons will typically include one or more of the following: Gly (ggg); Ile (att); Leu (ctc); Ser (tcc); Val (gtc). In general, the degree of preference of particular codon is indicated by the prevalence of the codon in highly expressed human genes as indicated, for example, in U.S. Pat. No. 5,795,737, herein incorporated by reference. For example, "atc" represents 77% of the Ile codons in highly expressed mammalian genes and is the preferred Ile codon; "att" represents 18% of the Ile codons in highly expressed mammalian genes and is the less preferred Ile codon. The sequence "ata" represents only 5% of the Ile codons in highly expressed human genes and thereof is a non-preferred codon.

Replacing a codon with another codon that is more prevalent in highly expressed human genes will generally increase expression of the gene in mammalian cells. Accordingly, the invention includes replacing a less preferred codon with a preferred codon as well as replacing a non-preferred codon with a preferred or less preferred codon. A "synthetic gene" is a nucleotide sequence encoding a naturally occurring protein in which a portion of the naturally occurring codons have been replaced by other codons. For example, a non-preferred codon is replaced with preferred codon or a less preferred codon encoding the same amino acid. In addition a less preferred codon can be replaced by a preferred codon. Synthetic genes generally encode proteins normally expressed by eukaryotic cells, including mammalian cells. However, by replacing codons to create a synthetic gene the expression in mammalian cells (especially human cells) of a viral genes described herein can be increased compared to the expression of the naturally occurring gene.

In preferred embodiments, the synthetic gene is capable of expressing the NC, RT or IN gene protein at a level which is at least 110%, 150%, 200%, 500%, or more of that expressed by said natural gene under identical conditions (i.e., same cell type, same culture conditions, same expression vector). In the present invention the codon bias present in the HIV gag and pol proteins can be overcome by replacement of a portion of the non-preferred and/or less preferred codons found in the HIV genes with preferred codons to produce a vector capable of higher level expression.

Accordingly, in one embodiment, preferred codons for the viral constructs of the present invention can be selected from the group consisting of gcc, cgc, aac, gac, tgc, cag, ggc, cac, atc, ctg, aag, ccc, ttc, agc, acc, tac, and gtg, while less preferred codons can be selected from the group consisting of ggg, att, ctc, tcc, and gtc and all codons other than the preferred codons and the less preferred codons can be considered non-preferred.

Codon optimization of the HIV-1 gag-pol gene has also been described by Kotsopoulou et al. who has constructed a HIV-1 gag-pol gene where the nucleotide sequence has been altered in the majority of the codons to retain the primary amino acid sequence, but to exploit the favored codon usage of human cells. (Kotsopoulou et al. *J. Virol.* (2000) 74: 4839–4852.) Codon optimization of the gag gene has been described by Graf et al. who found increased expression of the gag protein in mammalian cells (Graf et al. *J. Virol.* (2000) 74: 10822–10826. In addition, codon optimization has been demonstrated to increase the expression levels and the immunogenicity of DNA vaccines encoding gag, as described by Deml et al. *J. Virol.* (2001) 75: 10991–101001.

It will be appreciated by those skilled in the art that one or more DNA polymorphisms that lead to changes in the amino acid sequence are within the scope of the invention. Such genetic polymorphisms may exist due to natural allelic variation. Any and all such nucleotide variations and resulting amino acid polymorphisms that are a result of natural allelic variations and that do not alter the functional activity of the different HIV regions, are also intended to be within the scope of the invention.

EXAMPLES

Example 1

Generation of the pVacc10 Construct

The parental DNA clone used in the development of pVacc10 is the plasmid pM1–2/BR which was a derivative of the biologically active pHXB2gpt. (See Poon et al., *J. Virol.* 70 (10): 6607–6616 (1996), the teachings of which are incorporated herein in their entirety by reference). In order to construct a plasmid with HIV-1 sequences, SIV sequences in pVacc3 were substituted with HIV-1 sequences using the Nar 1-Xho1 fragment (where the Xho11 site has been filled in by Clainow polymerase) from pM1–2/BR which replaced a Nar1-SnaB1 fragment in pVacc3. This manipulation resulted in a plasmid carrying HIV-1 coding sequences under the control of the CMV promoter instead of the HIV-1 LTR. Furthermore, the 3' HIV-1 LTR was no longer present and it was substituted by the SV40 polyA. In this vector, arginine and lysine of the HIV-1 NC (nucleocapsid) gene were mutated to alanines. Oligo-mediated site-specific mutagenesis by overlap extension was performed on pHXB2gpt to obtain pM1–2/BR. (See Horteon et al., "Methods in Enzymology," 217:270–279 (1993), Academic Press, San Diego, the teachings of which are incorporated herein in their entirety by reference). For each codon mutated to encode an alanine, the first two bases were changed to a G (guanine) and a C (cytosine) while the third base was left unaltered. Additionally, a total of 12 mutations were introduced in the RT and Integrase genes using the QuickChange Mutagenesis kit (Statagene). Oligonucleotides used for the mutagenesis correspond to the forward and reverse (complementary, (C)) primers for the different HIV genes. The underlined regions indicate the points of mutation.

```
(a) RT mutagenesis:
Forward:
HIV-2750 5'cagtactaaagcggcaaaattagt(SEQ. ID. NO:11)
              agatttcgcagaacttaat
Reverse:
HIV-2750C5'attaagttctgcgaaatctacta (SEQ. ID. NO:12)
              attttgccgctttagtactg
```

```
(b) Integrase mutagenesis:
Forward:
HIV-4250 5'ggcccaagatgaagctgagaaat (SEQ. ID. NO:13)
              atgccagtaattgg
Reverse:
HIV-4250C5'ccaattactggcatatttctcag (SEQ. ID. NO:14)
              cttcatcttgggcc
Forward:
HIV-4338 5'gtagccagcgct-gataaagct  (SEQ. ID. NO:15)
              cagctaaaagg
Reverse:
HIV-4338C5'cctttagctgagctttatcagc (SEQ. ID. NO:16)
              gctggctac
Forward:
HIV-4411 5'ggcaactagcttgtacacattta (SEQ. ID. NO:17)
              gaagg
Reverse:
HIV-4411C5'ccttctaaatgtgtacaagctag (SEQ. ID. NO:18)
              ttgcc
Forward:
HIV-4564 5'caatacatactgccaatggcagc (SEQ. ID. NO:19)
Reverse:
HIV-4564C5'gctgccattggcagtatgtattg (SEQ. ID. NO:20)
Forward:
HIV-4674 5'ggagtagt-agcatctatgaata (SEQ. ID. NO:21)
              aag
Reverse:
HIV-4674C5'ctttattcatagatgctactact (SEQ. ID. NO:22)
              cc
```

```
(c) Nucleocapsid mutagenesis:
Forward
pBR 5'-AATTGCGCGGCCCCTGCGGCAGCGGGC (SEQ. ID. NO:23)
                                    TGT
Reverse:
pBRC 5'-ACAGCCCGCTGCCGCAGGGGCCGCGCA(SEQ. ID. NO:24)
                                    ATT
Forward:
pM1-2 5'-AGGGCCCCTAGGAAAAAGGGCTGTT (SEQ. ID. NO:25)
GGGCATGTGGAGCGGAAGGACACCAAATGGCAG
                      ATTGTACTGAG
Reverse:
pM1-2C 5'-GCCCTTTTTCCTAGGGGCCCTGCA (SEQ. ID. NO:26)
ATTTGCGGCTGTGTGCCCTTCTGCGCCACAATTG
                  AAACACGCAACAATCTT
```

All mutations were confirmed by dideoxy sequencing. All DNA manipulations were performed according to standard procedures. (Ausubel et al., (1987) Current Protocol in Molecular Biology, John Wiley and Sons, Inc., NY, the teachings of which are incorporated herein in their entirety by reference).

Example 2

Production of Viral Particles Using pVAcc10

To investigate the production of viral particles generated using the pVacc10 construct, recombinant cell lines were created. One example of a recombinant cell line was created using the cell line 293T. The cell line 293T was maintained in Dulbecco modified Eagle medium (GIBCO/BRL, Bethesda, Md.) supplemented with 10% fetal bovine serum (GIBCO) at 37° C. under 5% $CO_2$. Another cell-line, the H9 T-lymphoid cell line was also used and maintained as previously described. (Hanke, T., et al., 1999. *J. Virol.* 73(9): 7524–7532, the teachings of which are incorporated herein in their entirety by reference). Transfection of 293T cells by calcium phosphate precipitation and analysis of viral mutants were carried out as described previously. (Aldovini et al., *J. Virol.* 64: 1920–1926 (1990), and Almond et al., AIDS 12 (Suppl A): S133–140 (1998), the teachings of which are incorporated herein in their entirety by reference). Supernatants from transfected 293T cell cultures were harvested 48 hours post-transfection and assayed for p24 antigen using an enzyme-linked immunosorbent assay (ELISA) (p24 core profile kit, DuPont) and for RT activity (as described by Bernstein et al., *Vaccine* 17:1681–1689 (1999), the teachings of which are incorporated herein in their entirety by reference). Viral supernatants derived from two independent transfections of pVacc10 were tested in infectivity assays. Cells, specifically 5×10$^5$ H9 cells, were exposed to amounts of virus from transfected cells equivalent to 25 ng of p24 in 2 ml of medium. After 3 hours of infection, cells were washed, resuspended in 2 ml of tissue culture medium and maintained in 24 well plates. Cultures were fed every 4 days by removing 1.5 ml of the 2 ml of cell culture suspension and replacing it with fresh medium. Cell density increased from 5×10$^5$ just after feeding to 2×10$^6$ four days later. At each 4-day interval, cleared supernatants were utilized for p24 ELISA and harvested cells were assayed by immunofluorescence. Each time point of each culture was evaluated in duplicate in both assays. Cultures were carried for 30 days after infection. Viral particles produced by pVacc10 were not infectious in culture.

Example 3

Investigation of RNA Viral Packaging Using pVacc10

To investigate whether RNA was packaged using the pVacc10 construct the following procedure was used. After evaluation of p24 in the medium, supernatant from cells transfected with pVacc10 containing virus particles equivalent to 15 ng of p24 was centrifuged to pellet the virions, viral RNA was extracted and quantitative RT-PCR was performed on RNA samples according to a previously described procedure. (Fuller et al., *Immunol. Cell Biol.* 75(4):389–396 (1997), the teachings of which are incorporated herein in their entirety by reference). Briefly, the pellet was resuspended in 0.5 ml of Solution D (4.2 M guanidine thiocyanate, 0.1 M sodium citrate, 0.5% SDS, 7.2% 2-mercaptoethanol) containing 120 mg/ml of yeast tRNA as a carrier to monitor final RNA recovery. The RNA was extracted with phenol-chloroform and precipitated with ethanol. In order to eliminate contaminating transfection or cellular DNA, the RNA was then treated with 16 units of RQ1 DNase I (Promega) in the buffer recommended by the manufacturer (40 mM Tris, pH8, 10 mM NaCl, 6 mM MgCl$_2$, 10 mM CaCl$_2$) in the presence of 80 units of recombinant RNasin Ribonuclease Inhibitor (Promega) for 1 hour at 37° C. The DNase I was denatured with Solution D and the RNA was precipitated with ethanol. DNase I-treated viral RNAs were resuspended in diethyl pyrocarbonate (DEPC)-treated water and the yeast tRNA concentration was adjusted to 0.5 mg/ml. RNA samples were obtained from three independent transfections. RNA samples corresponding to 2 ng of p24 were reverse transcribed in a 30 μl reaction with Superscript II™ (GIBCO/BRL) using a gag-specific primer (HIVc1686, 5'-ACCGGTCTACATAGTCTCTA-3'; SEQ. ID. NO: 34). Three ml of this reaction were subjected to PCR with AmpliTaq™ DNA Polymerase (Perkin Elmer), in the presence of $^{32}$P-dCTP, employing the same primer used in the RT reaction and paired with an upstream gag-specific primer (HIV979, 5'-TACAACCATCCCTTCAG-3'; SEQ. ID. NO: 35). The negative controls included a sample from an RT-PCR reaction lacking input RNA, and an RT-PCR reaction with RNA extracted from a mock transfected supernatant. A PCR reaction on an equivalent amount of RNA which did not undergo reverse transcription was carried out for each sample to exclude incomplete DNase I treatment. An RT-PCR reaction using actin-related primers (ACT1, 5'-ATGGAAGAAGAGATCCGC-3' (SEQ. ID. NO: 36) and ACTR2, 5'-CCTCGTAGATGGGCACCG-3' (SEQ. ID. NO: 37)) was carried out to eliminate cellular RNA contamination. Equal volumes of RT-PCR or PCR samples were subjected to polyacrylamide gel electrophoresis (PAGE) and autoradiography. The intensity of each band was quantitated using a Molecular Dynamics PhosphorImager with ImageQuant software (Molecular Dynamics). The viral particles generated by pVacc10 do not incorporate detectable viral RNA.

Example 4

Vector Construction for SIV-Based Systems

To further determine the in-vivo efficacy of the vaccination protocol and the generation of the immune response, the art-recognized SIV-based experimental system was employed. The SIV constructs have the same mutations in the same amino acid residue positions as the pVAcc10 construct. In particular, mutations were made in the nucleocapsid protein at amino acid positions lysine 14, lysine 20, arginine 26, arginine 29, arginine 32, lysine 33, lysine 34, lysine 38, lysine 41, and lysine 47; in the RT protein at amino acid positions tryptophan 71, arginine 72, and arginine 78; in the In protein at positions histidine 14, histidine 18, cysteine 42, cysteine 45, aspartic acid 66, aspartic acid 118, and glutamic acid 154.

The same rationale was employed using the SIV virus as was employed for the HIV virus. Specifically, certain mutations were made in the SIV genome in order to produce an SIV virus that was incapable of infection but that could stimulate a host's immune system, in this case the host was the rhesus macaques monkey. To summarize the results presented below, the protocol established herein for making a viral DNA-based vaccine resulted in the stimulation of the specific-immune system, including the elaboration of specific IgA molecules particular to the mucosa.

All mutants of SIVmac239 were constructed using the infectious clone pMA239 (14110 bp) which carries a full copy of the molecular clone of SIV mac239. Mutations were introduced into the nucleocapsid (NC), reverse transcriptase (RT) and integrase (IN) genes of the SIV genome using oligonucleotide-mediated site directed mutagenesis by overlapping extension PCR (Table 4). (See Horton, R. M., et al., In: R. Wu (ed.). *Methods in Enzymology* Vol. 217 Part H (1993), Academic Press, San Diego, Calif., the teachings of which are incorporated herein in their entirety by reference).

TABLE 4

SIV proviral DNA constructs

| construct | 5'end | Gag NC | RT | IN | 3'end |
|---|---|---|---|---|---|
| pMA239 | LTR | wt | wt | wt | nef-stop, 3' LTR |
| pMA22polyA | LTR | 12 mutations[1] | 3 mutations[2] | 7 mutations[3] | Δnef, polyA[4] |
| pVacc 1 | CMV[5] | 12 mutations | 3 mutations | 7 mutations | Δnef, polyA |
| pVacc 2 | EF1a[6] | 12 mutations | 3 mutations | 7 mutations | Δnef, polyA |

[1]The NC mutations are Q3:G, C3:W, five R:A, and five K:A.
[2]The RT mutations are W71:A, R72:A, and R78:A.
[3]The IN mutations are alanine substitutions of the histidine and cysteine in the HHCC domain and of the aspartic and glutamic acid residues in the DD35E domain.
[4]The SV40 polyadenylation site replaces the 3'end of the SIV genome from the termination codon of the env gene to the end of the 3' LTR.
[5]The cytomegalovirus promoter (CMV) replaces the SIV 5' LTR from the beginning of the SIV sequence in pMA239 to the SIV NarI site in pVacc1.
[6]The eukaryotic polypeptide chain elongation factor 1a promoter (EF1a) replaces the SIV 5' LTR from the beginning of the SIV sequence in pMA239 to the SIV NarI site in pVacc2.

The oligonucleotides used in the mutagenesis are listed in Table 5 (oligonucleotides #1–18).

TABLE 5

Oligonucleotide primers used in generation of recombinant viruses (Codon mutations or restriction endonuclease sites introduced in the primer for construction of SIV recombinant are underlined).

| Primer | Sequence |
|---|---|
| 1. SIV2103 | 5'-ATGGATCCAACTGGGGTTGCA |
| 2. SIV2517C/NC | 5'-TGCAGAGTGTCCCTCTGCCCCACAAT TCCAACACGCAATTGGCGCTGCTGGTCCCGC CTGTTC |
| 3. SIV2506/NC | 5'-GAGGGACACTCTGCAGCGCAATGCGCAG CCCCAGCAGCACAGGGATGCTGGGCATGGGG AGCAATGGAC |
| 4. SIV2709C | 5'-CACAGCTGGGTCCTCTGGGGGAG |
| 5. SIV2630 | 5'-GAAAGAAGCCCCGCAATTTCC |
| 6. SIV3347C/RT | 5'-TAGTTCCGCAAAATCTATCAGCATTGCC GCTTTGTTGTTATC |
| 7. SIV3309/RT | 5'-AAGAACAAAGCGGCAATGCTGATAGA TTTTGCGGAACTAAAT |
| 8. SIV3632C | 5'-ATTTGCCTTCCTGAAGGGTTC |
| 9. SIV4513 | 5'-AACAGACTACTAATCAACAAG |
| 10. SIV4880C/INT-HH | 5'-CACTATTCTGGGTAATCCAAATTTGAAT ACCAATTCTTTTACATTACTAGCGTATTTAT CAGCTTCTTCTTGT |
| 11. SIV4857/INT-CC | 5-AAATTTGGATTACCCAGAATAGTGGCCAG ACAGATAGTAGACACCGCTGATAAAGCTCAT CAGAA |
| 12. SIV5464C | 5'-TAATAGACCCGAAAATTTTTA |
| 13. SIV4964/INT-D | 5'-TTGGCAAATGGCTTGTACCCATCT |
| 14. SIV4986C/INT-D | 5'-GATGGGTACAAGCCATTTGCCAAG |
| 15. SIV5120/INT-D | 5'-TCTACACACAGCTAATGGTGCTAA |
| 16. SIV5142C/INT-D | 5'-TAGCACCATTAGCTGTGTGTAGAT |
| 17. SIV5228/INT-E | 5'-GGGAGTAGTGGCAGCAATGAATCA |
| 18. SIV5250C/INT-E | 5'-GATTCATTGCTGCCACTACTCCCT |
| 19. A22/BlpI | 5'-AACAGCTTAGCTCTAGAGTCGACCAGAC AT |
| 20. A22C/SnabI | 5'-AACATACGTATATTAAAGCAGTACTTGT TA |
| 21. CMV4062/SfI | 5'-TTGCTCACATGGCCTCAGAGGCCTTCAA TATTGGCC |
| 22. CMV824C/BspEI | 5'-TCGAGACTGTTGTGTCCGGAGCACTGAC TG |
| 23. EF522/SfI | 5'-AATGGACCTTCTAGGGCCTCAGAGGCCT GG |
| 24. EF1770C/BspEI | 5'-TCTCGAGGTCGAGGGATCTCCGGAGAAT TCTTCACGACA |

In addition, the SIV 5' LTR was replaced by the Cytomegalovirus promoter (CMV) or eukaryotic polypeptide chain elongation factor 1a promoter (EF1a) and the SIV 3' LTR was substituted with the polyadenylation site (polyA) from pSG5 (Stratagene). Paired primers, 19 and 20, (Table 5) were used to obtain the polyA fragment from the pSG5 vector by using PCR, which was used as a template. The fragment was digested with BlpI/SnaBI and ligated to a SnaBI site that was introduced in the wild-type proviral DNA to replace sequences 9505–10709 of SIVmac239 and to the unique BlpI site present in pMA239. To change the SIV 5' LTR to a CMV promoter, primers 23 and 25 (adding, respectively, SfiI and BspEI sites at the two ends of the fragment) were used to obtain the CMV promoter fragment from the pRL CMV vector. (See Regier et al., *AIDS Res. Hum. Retroviruses* 6:1221–1231 (1990), the teachings of which are incorporated herein in their entirety by reference). A SfiI site was introduced in the pUC18 sequence of pMA239, and this site was introduced 220 nucleotides 3' of the AatII site. The fragment containing the CMV promoter replaced the sequences from the SfiI site to the NarI site of pMA239. The modified plasmid is designated Vacc1 and contains the CMV promoter, multiple mutations in the SIV structural genes, and a replacement of the 3' LTR with a polyA site.

A similar strategy was used to replace the 5' LTR with an EF1a promoter (NCBI Accession No. AF16376). Primers 26 and 27 were used to amplify the EF1a promoter from pEBB by PCR. (See Tanaka et al., *Mol. Cell. Biol.* 15:6829–6837 (1995), the teachings of which are incorporated herein in their entirety by reference). The fragment obtained replaces the fragment from the SfiI site to the NarnI site of pVacc1, to obtain the plasmid, designated pVacc2. All mutated viral sequences were confirmed by dideoxy sequencing, and the DNA manipulations were carried out according to previously published procedures. (Ausubel et al., *Current Protocol in Molecular Biology*, John Wiley and Sons, Inc., New York (1987), the teachings of which are incorporated herein in their entirety by reference).

Example 5

Transfection of Cells Using the SIV Construct

Eukaryotic cell transfections: 293T cells were seeded at a density of $10^6$/100-mm plate, 24 hours prior to transfection, in DME medium supplemented with 10% fetal calf serum and incubated at 37° C. in 5% $CO_2$. Transfection was generally carried out by a calcium phosphate method using 10 µg of plasmid DNA/100 mm plate as described by Chen and Okayama. (Chen et al., *Mol. Cell. Biol.* 7:2745–2752

(1987), the teachings of which are incorporated herein in their entirety by reference). Transfection efficiency was evaluated after 48 hours by immunoperoxidase staining of transfected cells using an SIV-specific polyclonal serum and a rabbit-anti monkey IgG conjugated with peroxidase (Sigma).

Example 6

Nucleic Acid Analysis

RNA was extracted from 293T cells using the Triazol reagent (Gibco/BRL). In order to eliminate contaminating transfection or cellular DNA, the RNA was treated with 16 units of RQ1 DNase I (Promega) in the buffer recommended by the manufacturer and quantitative RT-PCR was performed on RNA samples according to a previously described procedure. (Poon et al., *J. Virol.* 72:1983–1993 (1998), the teachings of which are incorporated herein in their entirety by reference). Signals were detected by autoradiography with Kodak XAR film using a Dupont Quanta III screen. The intensity of each band was quantitated using a Molecular Dynamics PhosphorImager with ImageQuant software (Molecular Dynamics).

Example 7

Particle Characterization

Particles produced from the vectors were characterized biochemically. Supernatants from transfected cells were collected, filtered through a 0.45 micron filter and centrifuged through a 3 ml cushion of 15% (w/vol.) sucrose at 27,000 rpm for 3 hours in an SW28 rotor (Beckman). Each pellet was resuspended in 10 mM Tris, (pH6.8) with 0.1% Triton and the p27 Capsid Antigen (CA) content determined by ELISA assay. Samples equivalent to approximately 25 ng of CA were resuspended in Laemmli buffer (5% glycerol, 1% SDS, 31.875 mM Tris (pH6.8), 0.005% bromophenol blue), subjected to sodium dodecyl sulfate-polyacrylamide gel electrophoresis (SDS-PAGE). The proteins were transferred to nitrocellulose, and probed with SIV positive serum as described previously. (Poon et al., *J. Virol.* 72:1983–1993 (1998), the teachings of which are incorporated herein in their entirety by reference). $^{125}$I-Protein A (New England Nuclear) was used to detect HIV specific proteins by autoradiography.

After evaluation of SIV CA in the medium of all the transfectants, supernatants containing virus particles equivalent to 250 ng of CA were centrifuged to pellet the virions. Viral RNA extraction was carried out in presence of equal amounts of added tRNA, which was used to monitor the final recovery of RNA. RNA samples were resuspended in DEPC treated $H_2O$ to obtain identical concentrations of tRNA (1 µg/µl). Quantitative RT-PCR was performed on RNA samples equivalent to 4 ng of p27 according to a previously described procedure. (Poon et al., *J. Virol.* 70: 6607–6616 (1996), the teachings of which are incorporated herein in their entirety by reference). Electron microscopy (EM) was carried out on sections of embedded particles according to standard procedures.

Example 8

Infectivity Assays

Viral supernatants derived from two independent transfections per construct were tested in infectivity assays. Cells, specifically $5 \times 10^5$ CEMx174 cells, were exposed to amounts of virus from transfected cells equivalent to 250 ng of p27 in 2 ml of medium. After 3 hours of infection, cells were washed, resuspended in 2 ml of tissue culture medium and maintained in 24-well plates. Cultures were fed every 4 days by removing 1.5 ml of the 2 ml cell culture suspension and replaced with fresh medium. Cell density increased from $5 \times 10^5$ just after feeding to approximately $2 \times 10^6$ 4 days later. At each 4 day interval, cleared supernatants were tested for virus content by SIV p27 ELISA. Cultures were maintained for 30 days after infection. Nested PCR was performed on cellular DNA, and RT-PCR on RNA, from pelleted supernatants from cultures that scored negative in SIV p27 ELISA.

Example 9

Vaccine Formulation Using the SIV Constructs

The candidate vaccine plasmids were grown from a single *E. coli* colony in Luria Broth with 100 µg/ml ampicilin at 30° C. for no more than 18 hours. DNA was purified by CsCl gradient followed by passage through an endotoxin-free column (Quiagene). (See Ausubel et al., *Current Protocol in Molecular Biology*, John Wiley and Sons, Inc., New York (1987), the teachings of which are incorporated herein in their entirety by reference). The vaccines were formulated in a variety of different ways. For intradermal and intramuscular administration of the DNA vaccine, saline solution (Sigma) was used to resuspend the DNA and the concentration was adjusted to 1 µg/µl.

For mucosal administration, the vaccine DNA was formulated in liposomes, at a concentration of 0.5 mg/ml. Briefly, lyophilized DOTAP:Cholesterol in equimolar ratio (Calbiochem) was hydrated in 5% dextrose/$H_2O$ (D5W) to give 20 mM DOTAP/20 mM Cholesterol (1×). (See Templeton et al., *Nat. Biotechnol.* 15:647–652 (1997), the teachings of which are incorporated herein in their entirety by reference). The hydrated lipid mixture was sonicated for 5 minutes at 50° C. and heated for 10 minutes at 50° C. The mixture was sequentially extruded through decreasing size filters from 1 to 0.1 µm. Whatman Anotop filters with an aluminum oxide membrane specially made for liposome extrusion were used. The liposome/DNA complexes were made by mixing together 60 µl of 20 mM liposome suspension plus 90 µl of D5W, and 15 µl of a 10 mg/ml DNA stock plus 135 µl of D5W.

For administration using a gene gun, the gold particle-associated DNA preparation was formulated according to the manufacturer protocol (Bio-Rad). Plasmid DNA was precipitated onto 1.6 µm gold particles at a DNA loading ratio (DLR) of 5 µg DNA/mg gold. The microcarrier loading quantity (MLQ) was 0.5 mg gold/cartridge. The coated particles were accelerated using hand-held helium-powered Helios Gene Gun SyStem (BioRad).

Example 10

In Vivo Studies with Macaque Vaccination and Challenge

Nine Rhesus macaques were vaccinated at time 0, 9 weeks and 25 weeks with the SIV construct i.d. (group 1), i.d. and at the rectal mucosa (i.d/R) (group 2), i.d., R and i.m (group 3). When DNA was given intradermally, the animals in all vaccine groups received 0.5 mg of pVacc1 DNA (0.4 mg of DNA in saline by needle injection and 0.1 mg DNA by gene gun) in the skin that covers the gluteal area. For the mucosal vaccination of groups 2 and 3, 1 mg of pVacc1 DNA mixed with liposomes, prepared according to the protocol described above was administered to the rectal mucosa approximately 5 cm from the anal verge with a small syringe without needle. The intramuscular vaccination of group 3 consisted of the administration of 1 mg of vaccine pVacc2 DNA in 1 ml of saline in the gluteal muscle. When challenged, the macaques in this experiment received 5000 TCID$_{50}$ of cloned SIVmac239, administered to the rectal mucosa by syringe without needle. This amount of virus is equivalent to 9 ng of p27 and is estimated to be approximately 10 rectal macaque infectious doses (AID$_{50}$). This challenge dose corresponds to $10^5$ AID$_{50}$ by i.v. titration.

Collection and Processing of Rectal Secretions

Rectal secretions were collected before and at intervals after immunization with absorbent Weck-Cel sponges (WQindsor BioMedical, Newton, N.H.) using a modified wicking method. (Kozlowski et al., Comparison of the oral, rectal, and vaginal immunization routes for induction of antibodies in rectal and genital tract secretions of women, *Infect. Immun.* 65:1387–1394 (1997), the teachings of which are incorporated herein in their entirety by reference). This tampon applicator-based technique has been described in detail elsewhere. (Kozlowski et al., *J. Acquir. Immune Defic. Syndr.* 24(4):297–309 (2000), the teachings of which are incorporated herein in their entirety by reference). Briefly, a sponge moistened with 50 μl saline and housed within a pipet was inserted 6 cm into the rectum and exposed to rectal surfaces by withdrawing the pipet 1.5 cm while holding the sponge in place. After 5 minutes, the sponge was gently pulled back into the pipet, the entire apparatus was removed from the rectum, and sponges were stored at −80° C. in Eppendorf tubes. To extract secretions, each sponge was placed in the upper chamber of a double-chambered spin assembly soaked with 100 μl PBS containing 0.5% Igepal detergent (Sigma) and protease inhibitors then centrifuged at 20,000×g at 4° C. for 30 minutes. The volume of secretion eluted from each sponge and dilution factors introduced by the pre-moistening saline and elution buffer were calculated based on weights of fluid centrifuged into 2 ml microcentrifuge lower chamber tubes. Blood contamination in secretions was assessed by using ChemStrips 4 (Boehringer-Mannheim) to measure hemoglobin, which in our hands was found negligible, representing only 0.01% of that in blood on average.

Example 11

Antibody Detection

SIV-Specific IgG and IgA Detection

SIV-specific antibodies were measured by ELISA, using plates coated with whole virus or purified virus-derived gp130. Incubations were performed in duplicate and multiple double dilutions of each sample were evaluated. In assays for SIV-specific serum IgG antibodies, samples were tested initially at two dilutions (1:20 and 1:100). (Wyand et al., *J. Virol.* 70:3724–3733 (1996), the teachings of which are incorporated herein in their entirety by reference). Samples highly positive at 1:100 were re-tested and further diluted at 1:80, 1:160, 1:320, 1:640 and so on. Bound SIV-specific antibodies were detected by incubation with an affinity purified donkey anti-human IgG-alkaline phosphatase conjugate (Jackson Laboratories).

For detection of SIV and gp130-specific IgA and IgG in rectal secretions and virus-specific IgA in serum, Nunc MaxiSorp microtiter plates were coated with 250 ng/well SIV viral lysate or purified native gp130 (both from Advanced Biotechnologies, Rockville, Md.). Antibodies measured in these SIV ELISAs likely do not include those to gp130 as this envelope protein could not be detected on plates coated with viral lysate using 5 μg/ml of anti-gp130 antibody (Advanced Biotechnologies), the working standard in gp130 ELISAs. Plates were reacted at 4° C. with two-fold dilutions of samples in 4% goat serum/0.05% Tween/PBS and developed the following day with a highly specific anti-monkey IgA mouse IgG monoclonal antibody (provided by Dr. Susan Jackson, University of Alabama at Birmingham), followed by biotinylated goat anti-mouse IgG antibody (Southern Biotechnology Associates, Birmingham, Ala.) from which antibodies cross-reactive with monkey IgG had been removed by passage through a column of CNBr-activated Sepharose (Pharmacia) conjugated to monkey IgG. (See Ward et al., *J. Med. Primatol.* 24:74–80 (1995), the teachings of which are incorporated herein in their entirety by reference).

In assays for SIV-specific IgG in rectal secretions, plates were developed with goat anti-monkey IgG antibody (Accurate, Westbury, N.Y.) that had been biotinylated in the laboratory using the Pierce (Rockford, Ill.) Sulfo-NHS-LC-Biotin EZ-link kit. Optimal dilutions of all antibodies were determined by checkerboard serial titration as described. (Margulies, *Criss-cross serial dilution analysis to determine optimal reagent concentrations*. In: Coico R., ed. Current Protocol in Immunology. New York: John Wiley & Sons, 1998:2.1.17–2.1.18, the teachings of which are incorporated herein in their entirety by reference). Color development was monitored after reacting plates with avidin-labeled peroxidase and ABTS/H$_2$O$_2$ substrate as described in Kozlowski et al., (1997). *Infect. Immun.* 65:1387–1394. To determine endpoint titers of antibody in secretions, the last sample dilution producing an absorbance value≧mean absorbance+3 SD in 8 control wells (containing sample buffer with 4% goat serum in PBS-Tween) was multiplied by the dilution factor introduced into the secretion during elution from sponges. Pooled serum from SIV-infected monkeys was arbitrarily assigned 10,000 unit/ml of anti-SIV IgA antibody and used to generate standard curves in these assays for interpolation of antibody concentrations in samples.

To determine with accuracy whether rectal secretions contained significant levels of SIV-specific antibodies and to facilitate comparisons among animals in which total Ig concentrations in secretions are highly variable, measured antibody concentrations were divided by total IgA or total IgG concentration in each sample. Total IgA and IgG were similarly quantitated by ELISA using plates coated with goat anti-monkey IgA or IgG (Accurate, Westbury, N.Y.), a calibrated monkey serum standard provided by Dr. M. W. Russell of the University of Alabama at Birmingham and the above secondary reagents.

Neutralizing antibody assays: Antibody-mediated neutralization of SIV was measured in a CEMx174 cell-killing assay as described previously. (Langlois et al., *J. Virol.*, 72:6950–6955 (1998), and Montefiori et al., *J. Immunol.* 157:5528–5535 (1996), the teachings of which are incorporated herein in their entirety by reference). Specifically, 50 μl of cell-free virus containing 500 TCID$_{50}$ was added to multiple dilutions of test serum in 100 μl of growth medium in triplicate in 96-well culture plates. The mixtures were incubated at 37° C. for 1 hour followed by the addition of CEMx174 cells ($5 \times 10^4$ cells in 100 µl) to each well. Infection led to extensive syncytium formation and virus-induced cell killing in approximately 4–6 days in the absence of antibodies. Neutralization was measured by staining viable cells with Finter's neutral red in poly-L-lysine-coated plates. Percent protection was determined by calculating the difference in absorption ($A_{540}$) between test wells (cells+serum sample+virus) and virus control wells (cells+virus), dividing this result by the difference in absorption between cell control wells (cells only) and virus control wells, and multiplying by 100. Neutralization was measured at a time when virus-induced cell-killing in virus control wells was greater than 70% but less than 100%. Neutralizing antibody titers ere given as the reciprocal dilution required to protect 50% of cells from virus-induced killing. Neutralization was measured with two stocks of SIV: 1) a laboratory-adapted stock of SIVmac251 produced in H9 cells and 2) molecularly cloned SIVmac239/nef-open produced in rhesus PBMC by using a vial of the original animal challenge virus as seed stock. The former virus is highly sensitive to neutralization whereas the latter virus is extremely difficult to neutralize in vitro.

Example 12

Cytotoxic T lymphocyte Assays

To investigate the immune response the following procedures were used:
(a) In vitro stimulation of PBMC: Autologous herpes papiotransformed B lymphoblastoid cell lines (B-LCL) were infected at an MOI of 10 pfu/cell with a recombinant vaccinia vector expressing the SIV mac251 Gag/Pol and the SIV mac239 Env (provided by Dr. Panicali, Therion Biologics, Cambridge Mass.). No recombinant vaccinia viruses expressing the SIVmac239 Gag/Pol are currently available, but the SIVmac251 and SIVmac239 molecular clones are almost identical in Gag and Pol proteins. Vaccinia viruses expressing the SIVmac251 Gag/Pol proteins were used to detect CTL induced by the SIVmac239-derived vaccine. After an overnight incubation, cells were washed, resuspended in 10 µg/ml psoralen in RPMI with 10% FCS (R-10), and irradiated with a long wave UV light source for 5 minutes. Following three washes, B-LCL were used as stimulator cells at a stimulator/responder ratio of 1:10 with $2-4 \times 10^6$ PBMC/ml. Recombinant IL-2 was added on day 4, and cultures were fed with fresh medium containing IL-2 twice per week until tested for CTL activity between 10 and 14 days following restimulation. (Johnson et al., *J. Virol.* 71:7711–7718 (1997), the teachings of which are incorporated herein in their entirety by reference).
(b) $^{51}$Cr release assay: Target cells consisted of B-LCL infected with recombinant vaccinia viruses expressing the SIVmac251 Gag, SlVmac251 Pol or the SIVmac239 Env, or as a negative control, the unmodified vaccinia virus NYCBH. Vaccinia-infected targets were prepared by incubating $2.5-10 \times 10^6$ B-LCL in log-phase growth with recombinant vaccinia at 10 pfu/cell for 16 hours at 37° C. Cells were labeled with 100–150 µCi of $Na_2(^{51}CrO_4)$ for 60 minutes and washed 3 times with R10. Cytolytic activity was determined in a standard $^{51}$Cr-release assay using U-bottom microtiter plates containing $10^4$ targets per well. Lysis was generally examined at effector to target ratios (E:T) of 40:1, 20:1 and 10:1, although in some cases lower E:T ratios were used due to a low number of effector cells. To decrease background CTL activity and enhance the detection of SIV-specific activity and enhance the detection of SIV-specific activity, autologous unlabeled B-LCL (cold target inhibition) at a cold:hot target ratio of 15:1 were employed. Plates were incubated in a humidified incubator at 37° C. for either 4 or 5 hours. All assays were performed in duplicate or triplicate. Supernatants (30 µl) were harvested and counted in an automated scintillation plate reader (Wallac MicroBeta-Plus Liquid Scintillation Counter) using scintillation plates (Lumaplates). Based on examination of SIV-specific CTL activity in over 20 negative controls studied to date, SIV-specific CTL activity of $\geq 5\%$ at two different E/T ratios was considered significant.

Example 13

PBMC CTL Tetramer Analysis

In the subset of vaccinated animals that express the Mamu-A*01 allele, the frequency of CD3+CD8+ cells specific for the SIV gag 11C-M epitope was determined using MHC tetramers (100). Monkeys were typed for the presence of the Mamu-A*01 allele as described, using Mamu-A*01-specific PCR primers followed by sequencing to confirm the presence of the Mamu-A*01 allele. (Knapp et al., *Tissue Antigens* 50:657–661 1997), the teachings of which are incorporated herein in their entirety by reference). The gag 11C-M epitope was immunodominant in vaccinated or infected Mamu-A*01+ animals, and thus flow cytometric analysis of the frequency of Mamu-A*01/gag 11C-M T cells was likely to be representative of the SIV-specific CTL response as a whole. (Egan et al., *J. Virol.* 73:5466–5472 (1999), the teachings of which are incorporated herein in their entirety by reference). The frequency of tetramer-binding cells in peripheral blood was analyzed using MHC tetramers consisting of the Mamu-A*01 molecule complexed with the SIV gag 11C-M peptide and complexed with streptavidin-APC (Molecular Probes, Eugene, Oreg.) (kindly provided by Dr. John Altman, Emory University). Antibodies used included FITC-conjugated anti-human CD3 (SP34, Pharmingen, San Diego, Calif.), and PerCP-conjugated anti-human CD8 (Becton Dickinson, Mountain View, Calif.). Simultest reagents were used as FITC/PE isotype controls (Becton Dickenson). Analysis was performed using a FACSCalibur flow cytometer (Becton Dickenson). In general, more than 200,000 events were acquired and analysis of tetramer staining cells was carried out on $CD3^+$ $CD8^+$ gated lymphocytes. Concurrent negative controls consisting of vaccinated or infected Mamu-A*01-negative animals were carried out at each time point and gates established so as to yield less than 0.01 to 0.04% tetramer-binding cells in negative controls.

Example 14

RT-PCR to Investigate RNA Viral Loads

Plasma SIV RNA levels were measured by a real time RT PCR assay, essentially as described. (Suryanarayana et al., *AIDS Res. Hum. Retroviruses* 14:183–189 (1998), the teachings of which are incorporated herein in their entirety by reference). The assay has a threshold sensitivity of 300 copy Eq/ml. Interassay variation is <25% (coefficient of variation).

Example 15

PBMC Limiting Dilution and Flow Cytometry

Cell-associated virus loads were measured by limiting dilution culture of PBMC every month during the post-challenge time course. (Wyand et al., *J. Virol.* 70:3724–3733

(1996), the teachings of which are incorporated herein in their entirety by reference). Twelve 3-fold dilutions of PBMC, starting with $10^6$ PBMC in the first dilution, were prepared. Each dilution was assayed in duplicate. The PBMC were co-cultured with a constant number of CEMx174 cells for 21 days, after which the supernatant was harvested and assayed for virus-associated p27. The titer was defined as the dilution where 50% of the wells were positive. Therefore a titer of 1 means that $10^6$ PBMC are needed to produce infection in one of the duplicates of the dilution and a titer of 12 means that 6 PBMC are sufficient to produce one positive CEMx174 culture of the two tested.

Whole blood collected in EDTA was analyzed for lymphocyte subset CD4 (OKT4a, Ortho, and/or Anti-Leu 3a, Becton Dickinson), CD8 (Anti-Leu 2a, Becton Dickinson), and CDw29 (4B4, Coulter Immunology) by a whole blood lysis technique previously described in Wyand et al., *J. Virol.* 70:3724–3733 (1996). Specifically, antibody (volume dependent upon antibody) was added to 100 µl of whole blood and incubated for 10 minutes in the dark. Lysing solution (Becton Dickinson) was added and cells were fixed with 0.5% paraformaldehyde. Samples were analyzed on Becton Dickinson FACScan cytometer.

Example 16

Testing for Infectivity and Morphology of Mutant SIV Particles

The SIV vectors constructed were tested for particle production and lack of infectivity in a tissue culture system. Viral supernatants derived from transfection were tested in infectivity assays using CEMx174 cells. A time course analysis of infections by all viruses was carried out for 30 days after infection, during which the level of particle-associated p27 was measured. Nested PCR on cellular DNA and RT-PCR on RNA from pelleted supernatants were carried out on cultures that scored negative in p27 ELISA. The results of PCR and RT-PCR were consistent with the other assays, indicating that the cell cultures were not infected (data not shown). Particles produced from the vectors were also characterized biochemically (FIGS. 1A–C). As expected, a particle whose protein composition was similar to that of wild-type virions was assembled even when the genomic RNA cannot be packaged (FIGS. 1A and B). Multiple mutations can be combined with no significant effect on particle assembly. Viral RNA was extracted from particles and quantitative RT-PCR was subsequently performed on RNA samples. These SIV vectors, containing a total of 22 mutations affecting the function of three essential genes of SIV, produced efficient non-infectious particles containing all major SIV proteins and no detectable viral RNA (FIG. 1C).

The different promoter efficiencies were measured by evaluating genomic viral RNA accumulation by RT-PCR in 293T transfected cells 48 hours after transfection (FIG. 1D). The construct pVacc2, containing the EF1a promoter, produced higher levels of RNA than construct pVacc1, containing the CMV promoter, or pMA22polyA, containing the SIV LTR, and the increased RNA accumulation correlated with the increase in particle production from the transfected cells.

Figure 2:
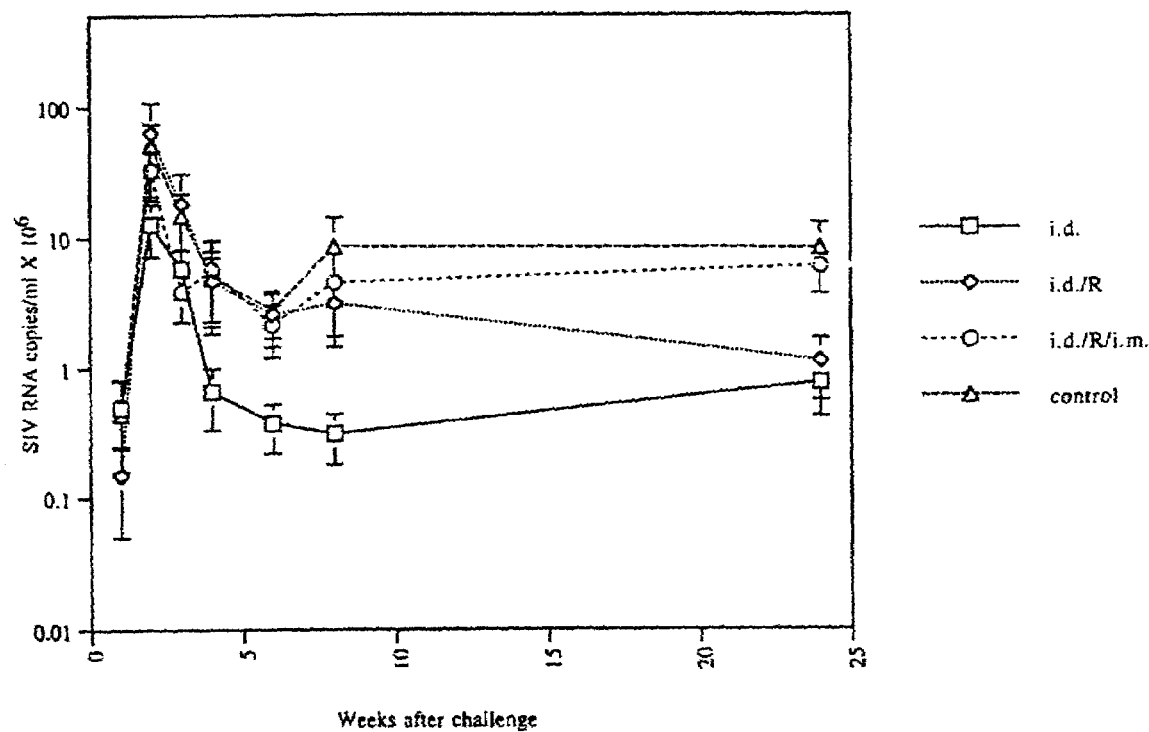
FIG. 2 is a graph depicting SIV viral loads in macaques challenged rectally by SIVmac239 (serum RT-PCR). Each time point represents the average and standard error of the values of viral loads detected in the three animals of one regimen group and reported in Table 10.

The morphology of the mutant particles was examined using electron microscopy (FIG. 2). SIV mutant particles produced from transiently transfected cells have cores that are less electron dense than mature wild-type particles. Without be bound by theory, lack of an electron dense core could be due to the absence or incorrect positioning of the RNA and/or to less efficient precursor processing. It is possible that the presence of an RNA dimer is critical for achieving the correct morphology of the particle, as the RNA might function as a scaffold in particle assembly and maturation. (Campbell et al., *J. Virol.* 69:6487–6497 (1995), the teachings of which are incorporated herein in their entirety by reference).

Example 17

Generation of Mucosal and Systemic Immunity

Mucosal immunity involves some unique aspects. For example, IgA is elaborated upon a sufficient immunogenic challenge to the mucosal area. The immune system particular to the mucosal area is of great importance given that the infectious agent, e.g., virus, can be prevented from entering the rest of the host, hence preventing systemic infection. Evaluation of the induction of SIV specific mucosal and systemic immunity in primates was performed. Nine rhesus macaques were inoculated with SIV DNA (groups 1–3) and 3 rhesus macaques with the control plasmid pUC19 (group 4). Three different vaccination regimens were used in order to investigate the ability of the DNA vaccine to prime different immunological compartments. The rationale was to compare a relatively simple regimen of immunization to more complex regimens.

A first regimen involved intradermal DNA immunization with DNA delivered to a region of the skin whose lymphatics drain to the iliac lymph nodes. A second regimen involved simultaneous inoculation at 1) the intradermal site used in the first regimen, and 2) the rectal mucosa. A third regimen was identical to the second, except that it included, in addition, intramuscular delivery of the DNA. The skin has the advantage that antigen presenting cells such as dendritic cells and Langerhans cells occur at high density in the epidermis and dermis, and this may be responsible for the relative efficiency of immunostimulation achieved through this route. Expression of DNA in the epidermis might be shorter lived than in muscle since epidermal cells ultimately migrate to more superficial layers during maturation and are sloughed off, but transfection of subepidermal cells could also occur and some of these may migrate to draining lymphoid organs. DNA was delivered intramuscularly in the third regimen in the hope of creating conditions for long lasting stimulation, as DNA has been found to be expressed for a considerable length of time when introduced into the skeletal muscle. (Wolff et al., *Hum. Mol. Genet.* 1:363–369 (1992), the teachings of which are incorporated herein in their entirety by reference). Our rationale was that the simplest regimen (group 1) could induce both systemic antibodies and possibly local secretory antibodies at mucosal surfaces that are drained by iliac lymph nodes. In the more complex regimens, parenteral and mucosal immunity was simultaneously stimulated. The vaccination schedule mimics the timetable used for hepatitis B vaccination. Because hepatitis B is the only chronic virus for which a protective vaccine is available and only one schedule could be investigated with the limited number of animals available.

Various samples were harvested during the course of the immunizations and the following immunological assays were performed: SIV-specific IgG, IgA and neutralizing activity in the serum, SIV-specific IgA and IgG in the rectal secretions, CTL activity in PBMC, and tetramer staining in Mamu A*01 positive macaques (2 of the 9 that received the vaccine). The results of the immune response assays prior to live virus challenge are briefly summarized in Table 6.

TABLE 6

Summary of immune responses to SIV DNA vaccines

| Group | Route | Antibody responses | | | Tetramer |
|---|---|---|---|---|---|
| | | SIV IgG[7] | SIV IgA[8] | CTL[9] | staining[10] |
| I (3, pVacc1) | i.d. | 3/3 | 1/3 | 3/3 | |
| II (3, pVacc1) | i.d./R | 2/3 | 3/3 | 1/3 | 2/2 |
| III (3, pVacc1/2) | i.d./R/i.m. | 3/3 | 1/3 | 2/3 | |
| IV (3, pUC18) | i.d./R/i.m. | 03/ | 0/3 | 0/3 | |

[7]IgG: serum samples 1:100–1:2560 dilution

[8]IgA: rectal secretion samples 1:23–1:2179

[9]SIV-specific CTL activity was scored positive when ≧5%, at any time after vaccination

[10]Tetramer staining of Mamu-A*01 positive animals (2) with 11/C-M Gag peptide, was considered positive when higher than 0.05%

The most striking of all measured immune responses were the levels of virus-specific IgA detected in rectal secretions of animals in group 2, which received the i.d./R. regimen. SIV-specific IgG titres in serum were weak in all groups, as has been observed previously with DNA vaccines. Virus-specific CTL activity was generally low and sporadic.

The analysis of SIV-specific IgA antibodies in rectal secretions collected two weeks after the third vaccination is shown in Table 7.

TABLE 7

SIV specific IgA antibodies in rectal secretions on day of challenge

| Group | | Route | SIV IgA | | gp130 IgA | | SIV IgG |
|---|---|---|---|---|---|---|---|
| | | | Specific activity[a] | Fold Increase[b] | Specific activity | Fold increase | Fold increase |
| I | 19775 | i.d. | 0.6 | 0.7 | 0.91 | 6.0+ | nd[c] |
| | 19796 | | 0.65 | 2.2 | 0 | | nd |
| | 19831 | | 0.89 | 1.3 | 0.32 | 2.7 | 5.2+ |
| II | 19777 | i.d./M | 1.68 | 23.9+ | 0 | | nd |
| | 19786 | | 7.06 | 54.1+ | 28.94 | 87.5+ | 17.55+ |
| | 19821 | | 1.65 | 39.5+ | 1.19 | 26.2+ | nd |
| III | 18781 | i.d./M/ | 0 | | 0 | | nd |
| | 18784 | i.m. | 0.60 | 3.0 | 0.42 | 1.7 | 1.3 |
| | 19856 | | 1.23 | 6.6+ | 0 | | nd |
| IV | 19783 | i.d./M/ | 0.69 | 3.2 | 0.11 | 1.0 | 1.6 |
| | 19816 | i.m. | 0 | | 0 | | nd |
| | 19845 | controls | 0.49 | 3.0 | 0.16 | 1.3 | nd |

+indicates samples with significant levels of virus specific IgA antibodies.
Significance: values of specific activity above the mean of all preimmune samples I 3 standard deviations (99% confidence inteval)
[a]Specific activity:

TABLE 7-continued

SIV specific IgA antibodies in rectal secretions on day of challenge

| Group | Route | SIV IgA | | gp130 IgA | | SIV IgG |
|---|---|---|---|---|---|---|
| | | Specific activity[a] | Fold Increase[b] | Specific activity | Fold increase | Fold increase |

Anti-SIV IgA units/micrograms total IgA, signifcant at ≧1 U/μg
anti-gp 130 IgA/micrograms total IgA, significant at ≧0.46 ng/μg
[b]Fold Increase: ratio between specific activity in post-immunization sample and specific activity in preimmune sample
[c]nd—no detectable SIV specific IgG antibodies
Total IgA concentration (microgram/ml) in secretions from significant responders were respectively: 1290 (19775), 23.5 (19777), 34.8 (19786), 3.8 (19821), and 32.9 (19856).

Samples from five of nine vaccinated animals were positive at a secretion dilution of 1:23 to 1:2179. No virus-specific IgA was detected in serum samples collected at the same time (data not shown). The secretions from two animals were also SIV-IgG positive. Analysis of SIV-specific IgA content in secretions collected one month after the first and second vaccinations indicated that three rectal mucosal doses were necessary to induce significant and consistent SIV-specific IgA levels (data not shown). The data show that the administration of a DNA vaccine at the rectal mucosa can stimulate significant SIV-specific IgA responses in primate rectal secretions. The absence of detectable SIV specific serum IgA indicates that the IgA was locally produced. The magnitude of the increase in SIV-specific IgA content in most of the positive rectal samples was substantially higher than that seen thus far in any other sample analyzed in SIV-vaccinated animals or in animals infected with SIV.

The intramuscular administration of DNA together with rectal and intradermal inoculations appeared to negatively affect the mucosal responses (compare fold increase in animals of groups 2 and 3 in Table 7). The instant invention provides evidence that simultaneous mucosal and intramuscular DNA vaccination may not be beneficial. However, the outcome might be different if simultaneous mucosal and systemic antigenic stimulation is provided by vaccines that are not DNA-based or are administered via different routes.

Humoral systemic virus-specific immunity was investigated by measuring SIV-specific serum IgG in an ELISA assay. As expected with DNA vaccines SIV specific IgG responses were weak, ranging from 1:100 to 1: 2560 on the day of challenge (Table 8). (See Hosie et al., *J. Virol.* 72:7310–7319 (1998), and Robinson et al., *Nat. Med.* 5:526–534 (1999), the teachings of which are incorporated herein in their entirety by reference). Neutralization assays carried out with the same samples were negative when SIVmac251 or SIVmac239 was used in the assay. These serum samples had no detectable neutralizing activity against the challenge virus (i.e., molecularly cloned SIV-mac239), which is consistent with the low sensitivity of this latter virus to antibody-mediated neutralization in and makes it uncertain that neutralizing antibodies were a component of protection in this study. Neutralization assays were not carried out with the rectal secretions, as detergent present in these samples made them unsuitable for cell culture.

TABLE 8

SIV-specific serum IgG titers during DNA immunization and after challenge

| Group | | DNA route | week 13 4 w post v2[a] | week 25 16 w post v2 | week 27 2 w post v 3 | week 28 1 w post chall | week 29 2 w post chall | week 30 3 w post chall | week 31 4 w post chall | week 39 12 w post chall | week 51 21 w post chall |
|---|---|---|---|---|---|---|---|---|---|---|---|
| I | 19775 | i.d. | N | N | 100(N) | 100 | 2560 | 2560(443) | 5120 | 10240 | (3964) |
|  | 19796* | i.d. | N | N | 1280(N) | 640 | 320 | 100(N) | 20 | 20 | (N) |
|  | 19831 | i.d. | N | N | 160(N) | 100 | 640 | 2560(3827) | 2560 | 5120 | (5218) |
| II | 19777 | i.d./M | 100 | N | 640(N) | 2560 | 5120 | 2560(313) | 5120 | 10240 | (4064) |
|  | 19786 | i.d./M | N | N | N(N) | N | N | 100(58) | 80 | 5120 | (3964) |
|  | 19821* | i.d./M | N | N | 100(N) | 100 | 20 | 20(N) | 20 | 20 | (N) |
| III | 19781 | i.d./M/i.m. | 20 | N | 320(N) | 320 | 2560 | 2560(310) | 2560 | 100 | (1376) |
|  | 19784 | i.d./M/i.m. | 160 | 20 | 1280(N) | 640 | 5120(1034) | 20480(1589) | 10240 | 20480 | (3372) |
|  | 19856 | i.d./M/i.m. | 80 | N | 2560(N) | 1280 | 5120(415) | 20480(415) | 5120 | 5120 | (4620) |
| IV | 19783 | pUVC19 | N | N | N | N | N | 40(107) | 100 | 10240 | (5353) |
|  | 19816 | i.d./M/i.m. | N | N | N | N | N | 40(334) | 80 | 5120 | (6439) |
|  | 19845 | pUVC19 | N | N | N | N | N | 100(252) | 100 | 5120 | (2612) |

[a] 4 s post v 2 = 4 weeks after second dose of vaccine
*indicates animals that did not become infected after challenge. Samples collected 4 weeks after first and 2 weeks after second dose of vaccine were SIV antidody negative. Numbers in parentheses indicate liter of neutralizing antibodies. All samples were tested in neutralization assays with SIVmac239 and SIVmac251. N = negative with both SIVmac239 and SIVmac251.

Systemic cell-mediated immunity was investigated by measuring virus-specific CTL activity in PBMCs. CTL responses were sporadically present at different levels in different animals (Table 9).

TABLE 9

SIV specific cell-mediated immunity during DNA immunizations

| Group | | DNA route | Week 4 4 post vacc 1 | Week 8 8 post vacc 1 | Week 15 6 post vacc 2 | Week 17 8 post vacc 2 | Week 21 12 post vacc 2 | Week 25 16 post vacc 2 | Week 27 2 post vacc 3 day of challenge | Week 29 2 post challenge | Week 30 2 post challenge | Week 31 3 post challenge | Week 36 9 post challenge |
|---|---|---|---|---|---|---|---|---|---|---|---|---|---|
| I | 19775 | i.d. | —/—/— | —/—/— | —/—/— | —/—/— | —/—/— | 5/4/9 | —/50/25 | | | 40/53/44 | NA |
|  | 19796 | " | —/—/— | 6/—/— | —/—/— | —/—/— | —/—/— | —/—/— | —/—/— | | | 9/—/— | 10/—/-7 |
|  | 19831 | " | 10/8/— | —/—/— | —/—/— | —/—/— | —/—/— | 20/18/15 | 7/—/12 | | | 20/21/45 | 21/29/23 |
| II | 19777 | id/R | 5/—/—12 | —/—/— | —/—/— | 10/7/6 | —/—/— | 11/9/7 | —/—/— (005) | (1049) | (373) | NA (121) | 9/9/13 (054) |
|  | 19786 | " | NA | —/—/— | —/—/— | —/—/— | —/—/— | —/—/— | —/—/— | | | —/—/— | —/—/— |
|  | 19821 | " | —/—/— | —/—/— | —/—/— | —/—/— | —/—/— | —/—/— | —/—/— (012) | (01) | (007) | —/—/— (005) | —/—/— (006) |
| III | 19781 | Id/R/im | 12/—/—11 | —/6/13 | 11/17/32 | —/5/8 | NA | —/5/15 | —/—/— | | | 33/—/— | —/—/— |
|  | 19856 | " | —/6/— | —/—/— | —/—/— | —/—/— | —/—/— | —/—/— | —/—/— | | | —/7/30 | —/—/— |
|  | 19784 | " | —/—/— | —/—/— | —/—/— | —/—/— | —/—/— | —/—/— | —/—/— | | | —/—/— | 7/—/41 |
| IV | 19783 | pC19id/R/im | ND | ND | ND | ND | ND | ND | —/—/— | | | —/—/10 | NA |
|  | 19816 | pC19id/R/im | ND | ND | ND | ND | ND | ND | NA | | | 5/—/46 | 8/—/28 |
|  | 19845 | pC19id/R/im | ND | ND | ND | ND | ND | ND | —/—/— | | | 9/—/9 | 9/9/13 |

The three results reported at each time point for each animal are percentage of CTI activity for the following different targets. Gag/Pol/Env, Number indicates percentage of lysis at highest ET ratio after background subtraction. Numbers in parenthesis indicate percentage of tetramer staining. Tetramer assays were carried out on PBMC from two Mamu-A*01 positive animals (19777 and 19821) and from one Mamu-*01 negative animal
ND not done
NA not available because of technical reasons Animals with different genetic backgrounds respond differently to a vaccine and it is possible that additional injections could have achieved more homogeneous levels of CTL responses. One animal (19775) showed a very high level of CTL activity against env (25%) and pol (50%) when assayed two weeks after the third vaccination, indicating that this vaccine has the potential to stimulate significant cellular responses. No clear difference in the level of SIV-specific CTL activity after challenge was noted between vaccinated and unvaccinated infected macaques.

The significant levels of IgA antibodies in rectal secretions elicited in all three animals vaccinated i.d./R provided an opportunity for a preliminary evaluation of the role of virus-specific IgA in prevention of infection. The small size of the animal groups prevents a meaningful statistical analysis of the challenge results. Therefore these results are reported anecdotally. Investigation of larger groups of animals immunized via the mucosal route is necessary to elucidate the role of virus specific mucosal immunity in infection and disease prevention.

Animals in all groups were challenged with live virus two weeks after the third immunization with 5000 TCID$_{50}$ of RT-PCR was carried out to detect RNA viral loads in serum samples from the day of challenge, weeks 1 to 25 after challenge (Table 10 and FIG. 2), and for cell-associated virus loads measured in a limiting dilution co-cultivation assay (data not shown).

In the infected animals, viral loads peaked two weeks post-challenge and subsequently decreased. Average viral loads were lower for the group vaccinated intradermally than for the control group, with differences of approximately 10 fold as measured by RT-PCR (FIG. 2). Two of the nine vaccinated animals (19796 of the i.d. group and 19821 of the i.d./R group) remained RT-PCR negative up to week 25 post-challenge (last available measurement). They also remained virus negative in a limiting dilution co-cultivation assay of their PBMC with CEMx174 cells carried out up to 63 weeks post-challenge. PCR analysis of PBMC DNA obtained from samples collected two weeks after challenge, when viremia peaked in all infected animals, was negative in the two animals that resisted challenge (data not shown). These animals did not show IgG anamnestic responses, possibly suggesting lack of or locally contained infection.

TABLE 10

SIV RNA viral loads post-challenge

RNA copy number (× $10^6$)

| Group | | DNA route | Day of challenge | week 1 | week 2 | week 3 | week 4 | week 6 | week 8 | week 25 |
|---|---|---|---|---|---|---|---|---|---|---|
| I | 19775 | i.d. | < | 1.3 | 23 | 8.8 | 0.59 | 0.53 | 0.46 | 0.8 |
| | 19796* | " | < | < | < | < | < | < | < | < |
| | 19831 | " | < | 0.17 | 15 | 8.6 | 1.4 | 0.58 | 0.47 | 1.5 |
| II | 19777 | i.d./R | < | 0.38 | 20 | 5.8 | 9.9 | 3 | 5.8 | 2.4 |
| | 19786 | " | < | 0.06 | 170 | 49 | 4 | 4.7 | 3.6 | 0.99 |
| | 19821* | " | < | < | < | < | < | < | < | < |
| III | 18781 | i.d./R/i.m. | < | 0.23 | 51 | 4.7 | 15 | 4.1 | 12 | 6.7 |
| | 19784 | " | < | 1.2 | 3.8 | 0.16 | 0.28 | 0.19 | 0.34 | 6.8 |
| | 19856 | " | < | 0.14 | 44 | 6.6 | 1.7 | 2.1 | 1.2 | 4.7 |
| IV | 19783 | PUC19 | < | 0.28 | 3.4 | 0.6 | 12 | 2.6 | 3.3 | 5.8 |
| | 19816 | i.d./R/i.m. | < | 0.54 | 55 | 30 | 2.4 | 5.2 | 22 | 19 |
| | 19845 | " | < | 0.51 | 98 | 14 | 0.58 | 0.56 | 0.17 | 0.28 |

Viral loads were measured by quantitative RT-PCR.
< indicates samples that are below level of detection (threshold sensitivity: 300 copy Eq/mL)
*indicates animals that were not infected after challenge.

cvloned SIVmac239, administered to the rectal mucosa. This irus amount corresponds to approximately 10 rectal (animal infectious dose$_{50}$) AID$_{50}$. Animals were bled weekly to assay for the presence of virus in peripheral blood and to determine whether an anamnestic response to SIV antigens was stimulated by exposure to the virus.

Anamnestic IgG responses were observed in all the animals that were previously SIV-IgG positive and became infected. Seroconversion could be documented by an increase in SIV-specific serum IgG in control animals 3 weeks after challenge (Table 8). Clear evidence of an anamnestic neutralizing antibody response was detected in serum from two animals (19831 and 19784) two to three weeks after challenge, suggesting that priming for neutralization epitopes was induced by the DNA vaccine. This anamnestic response was detected with a laboratory-adapted stock of SIVmac251 that is highly sensitive to neutralization (Table 8). There was no evidence of an anamnestic neutralizing antibody response as measured with SIVmac239.

PBMC FACS analysis was carried out for the T-cell immunological markers CDw29, CD4 and CD8 (Table 11). CDw29 measures a subpopulation of CD4 cells (memory CD4 cells) (Morimoto et al., Selective immunomodulation: utilization of CD29/VLA molecules. *Artif. Organs.* 20:828–831 (1996)), and its decline has been observed as an early indicator of the immunological decline that is correlated with subsequent disease progression. (Heinkelein et al., *J. Acquir. Immune Defic. Syndr.* 16:74–82 (1997), the teachings of which are incorporated herein in their entirety by reference). Two consecutive measurements of this marker that are below 10% are considered an indication of incipient immunological decline. SIV-infected animals vaccinated intradermally maintained values of CDw29, CD4 and CD8 within the normal range for a longer period of time than the other infected animals, while a decline affecting in particular the CDw29 marker was evident in most of the other infected animals. Animals 19781 and 19784 in group 3 and 19816 in group 4 were diagnosed with an AIDS-related illness and euthanized 41 to 49 weeks after challenge.

TABLE 11

PBMC FACS analysis

| Group | | DNA route | CDw29 | | | | CD4 | | | | CD8 | | | |
|---|---|---|---|---|---|---|---|---|---|---|---|---|---|---|
| | | | 0[a] | 35 | 47 | 63 | 0 | 15 | 47 | 63 | 0 | 35 | 47 | 63 |
| I | 19775 | i.d. | 16 | 9 | 10 | 9 | 27 | 22 | 23 | 17 | 15 | 24 | 27 | 21 |
| | 19796* | " | 17 | 18 | 13 | 18 | 25 | 29 | 30 | 37 | 30 | 39 | 33 | 38 |
| | 19831 | " | 21 | 12 | 8 | 12 | 38 | 35 | 29 | 35 | 30 | 42 | 43 | 43 |
| II | 19777 | i.d./R | 12 | 5 | 2 | 3 | 20 | 13 | 8 | 8 | 27 | 47 | 35 | 27 |
| | 19786 | " | 12 | 5 | 3 | 3 | 20 | 14 | 11 | 8 | 16 | 39 | 36 | 28 |
| | 19821* | " | 14 | 14 | 11 | 15 | 22 | 30 | 31 | 39 | 33 | 34 | 31 | 29 |
| III | 18781+ | i.d./R/i.m. | 9 | 8 | 4 | 3 | 13 | 22 | 17 | 16 | 21 | 42 | 40 | 52 |
| | 19784 | " | 20 | 9 | 1 | 2 | 35 | 22 | 5 | 7 | 31 | 37 | 40 | 21 |
| | 19856 | " | 17 | 9 | 6 | 8 | 33 | 28 | 22 | 25 | 28 | 44 | 23 | 41 |
| IV | 19783 | PUC19 i/d/R/i.m. | 8 | 12 | 4 | 4 | 10 | 35 | 15 | 20 | 13 | 29 | 24 | 22 |
| | 19816+ | " | 17 | 8 | 4 | 5 | 31 | 51 | 42 | 47 | 15 | 28 | 32 | 42 |
| | 19845 | " | 15 | 7 | 9 | 10 | 29 | 20 | 27 | 35 | 19 | 24 | 26 | 30 |

Numbers indicate percent age of PBMC that stains with antibodies CDw29, CD4, and CD*. Two consecutive measurements of the CDw29 marker that are below 10% are considered an indication of immunological decline.
[a]numbers indicate weeks from first immunization. Weeks 35, 47 and 63 correspondence to respectively 8, 20 and 36 weeks after challenge.
*indicates animals that did not become infected after challenge.
+indicates animals that were diagnosed with AIDS and euthanized 9.5 months after challenge.

Those skilled in the art will recognize, or be able to ascertain using no more than routine experimentation, many equivalents to the specific embodiments on the present invention. Such equivalents are intended to be encompassed by the following claims. All documents, patents and other publications cited herein are expressly incorporated by reference.

The invention claimed is:

1. A nucleic acid construct which encodes non-infectious HIV particles, the construct comprising:
   a) at least one replacement mutation in the gag gene of a HIV genome of a HIV particle wherein the gag gene encodes the amino acid sequence of the nucleocapsid (NC) protein, wherein the replacement mutation produces a single amino acid substitution in at least one position selected from the group consisting of the 5' flanking region (amino acids 1–14 of SEQ ID NO: 8), the 5' Cys-His box (amino acids 15–28 of SEQ ID NO: 8), to peptide linker region (amino acids 29–35 of SEQ ID NO: 8), the 3' Cys-His box (amino acids 36–49 of SEQ ID NO: 8) and the 3' flanking region (amino acids 50–55 of SEQ ID NO: 8), such that the replacement mutation prevents viral RNA packaging; and
   b) at least one further replacement mutation in the pol gene of said HIV genome selected from the group consisting of
      (i) at least one replacement mutation in the region of the pol gene that encodes the amino acid sequence in the finger domain (amino acid 1 to 84 of SEQ ID NO: 4) of the reverse transcriptase (RT) protein, wherein the replacement mutation produces a single amino acid substitution in the finger domain such that a dysfunctional reverse transcriptase protein is produced to prevent viral RNA conversion to DNA and
      (ii) at least one replacement mutation in the region of the pol gene that encodes the amino acid sequence of the catalytic (amino acids 51–212 of SEQ ID NO: 6) or multimerization domain (amino acids 1–50 of SEQ ID NO: 6) of the Integrase (In) protein, wherein the replacement mutation produces a single amino acid substitution in the catalytic or multimerization domain such that dysfunctional Integrase protein is produced to prevent a transcribed viral DNA molecule from integrating into a host cell genome.

2. The construct of claim 1, wherein the mutation in the NC protein is made in the 5' flanking region.

3. The construct of claim 2, wherein the mutation in the 5' flanking region is made in at least one position selected from the group consisting of arginine 3, arginine 10, lysine 11 and lysine 14.

4. The construct of claim 3, wherein the at least one position are substituted with alanine.

5. The construct of claim 1, wherein the mutation in the NC protein is made in the 5' Cys-His box.

6. The construct of claim 5, wherein the mutation in the 5' Cys-His box is made in at least one position selected from the group consisting of lysine 20, histidine 23 and arginine 26.

7. The construct of claim 6, wherein the at least one position are substituted with alanine.

8. The construct of claim 1, wherein the mutation in the NC protein is made in the peptide linker region.

9. The construct of claim 8, wherein the mutation in the peptide linker region is made in at least one position selected from the group consisting of arginine 29, arginine 32, lysine 33 and lysine 34.

10. The construct of claim 9, wherein the at least one position are substituted with alanine.

11. The construct of claim 1, wherein the mutation in the NC protein is made in the 3' Cys-His box.

12. The construct of claim 11, wherein the mutation in the 3' Cys-His box is made in at least one position selected from the group consisting of lysine 38, lysine 41, histidine44 and lysine 47.

13. The construct of claim 12, wherein the at least one position are substituted with alanine.

14. The construct of claim 1, wherein the mutation in the NC protein is made in the 3' flanking region.

15. The construct of claim 14, wherein the mutation in the 3' flanking region is made at position arginine 52.

16. The construct of claim 15, wherein the position arginine 52 is substituted with alanine.

17. The construct of claim 1, wherein the mutation in the RT protein is made in at least one position selected from the group consisting of tryptophan 71, arginine 72 and arginine 78.

18. The construct of claim 17, wherein the at least one position are substituted with alanine.

19. The construct of claim 1, wherein the mutation in the In protein is made in the catalytic domain.

20. The construct of claim 19, wherein the mutation in the catalytic domain is made in at least one position selected front the group consisting of aspartic acid 66, aspartic acid 118 and glutamic acid 154.

21. The construct of claim 20, wherein the at least one position are substituted with alanine.

22. The construct of claim 1, wherein the mutation in the In protein is made in the multimerization domain.

23. The construct of claim 22, wherein the mutation in the multimerization domain is made in at least one position selected from the group consisting of histidine 14, histidine 18, cysteine 42 and cysteine 45.

24. The construct of claim 23, wherein the at least one position are substituted with alanine.

25. The construct of claim 1, wherein the construct comprises a cluster of mutations, wherein the cluster of mutations is made in a region selected from the group consisting of the 5' flanking region of the NC protein, the 5' Cys-His box of the NC protein, the peptide linker region of the NC protein, the 3' Cys-His box of the NC protein, the 3' flanking region of the NC protein, a β3–β4 loop of the RT protein, the catalytic domain of the In protein and the multimerization domain of the In protein.

26. The construct of claim 1, wherein the construct comprises mutations in the NC protein at positions lysine 14, lysine 20, arginine 26, arginine 29, arginine 32, lysine 33, lysine 34, lysine 38, lysine 41 and lysine 47, mutations in the RT protein at positions tryptophan 71, arginine 72 and arginine 78, and mutations in the In protein at positions histidine 14, histidine 18, cysteine 42, cysteine 45, aspartic acid 66, aspartic acid 118 and glutamic acid 154.

27. The construct of claim 26, wherein the at least one position are substituted with alanine.

28. The construct of claim 1, further comprising a cytomegalovirus (CMV) promoter replacing a HIV 5' long terminal repeat (LTR) sequence.

29. The construct of claim 28, wherein the cytomegalovirus (CMV) promoter replaces the HIV 5' long terminal repeat (LTR) sequence from nucleotide 1 to nucleotide 636 of SEQ ID NO: 1.

30. The construct of claim 1, further comprising an elongation factor 1a (EF1a) promoter replacing a HIV 5' long terminal repeat (LTR) sequence.

31. The construct of claim 30, wherein the elongation factor 1a (EF1a) promoter replaces the HIV 5' long terminal repeat (LTR) sequence from nucleotide 1 to nucleotide 636 of SEQ ID NO: 1.

32. The construct of claim 1, further comprising an SV40 polyadenylation signal replacing a HIV 3' long terminal repeat sequence.

33. The construct of claim 32, wherein the SV40 polyadenylation signal replaces the HIV 3' long terminal repeat (LTR) sequence from nucleotide 8902 to the end of SEQ ID NO: 1.

34. The construct of claim 1, wherein the construct further comprises a selectable marker gene.

35. The construct of claim 34, wherein said selectable marker gene encodes a selectable marker which is selected from the group consisting of neomycin resistance, hygromycin resistance and dihydrofolate reductase.

36. A mammalian culture cell line, transfected with the construct of claim 1, which produces mutant virions.

37. The cell line of claim 36, wherein the construct is stably integrated in the genome of the cell line, and the cell line stably produces the non-infectious HIV particles.

38. An immunogenic composition to reduce viral load comprising the nucleic acid construct of claim 1.

39. An immunogenic composition to reduce viral load comprising the nucleic acid construct of claim 26.

40. An immunogenic composition to reduce viral load comprising the nucleic acid construct of claim 1, where at least one gag codon and at least one pol codon are optimized according to the codon usage in man.

41. An immunogenic composition to reduce viral load comprising the nucleic acid construct of claim 26, where at least one gag codon and at least one pol codon are optimized according to the codon usage in man.

42. A nucleic acid construct which encodes non-infectious HIV particles, the construct comprising:
  a) at least one mutation in the gag gene of a HIV genome of a HIV particle wherein the gag gene encodes the amino acid sequence of the nucleocapsid (NC) protein, wherein the mutation is made in the 5' flanking region (amino acids 1–14 of SEQ ID NO: 8), such that the mutation prevents viral RNA packaging; and
  b) at least one further mutation in the pol gene of said HIV genome selected from the group consisting of
    (i) at least one mutation in the region of the pol gene that encodes the amino acid sequence in the finger domain (amino acid 1 to 84 of SEQ ID NO: 4) of the reverse transcriptase (RT) protein, such that a dysfunctional reverse transcriptase protein is produced to prevent viral RNA conversion to DNA and
    (ii) at least one mutation in the region of the pol gene that encodes the amino acid sequence of the catalytic (amino acids 51–212 of SEQ ID NO: 6) or multimerization domain (amino acids 1–50 of SEQ ID NO: 6) of the Integrase (In) protein, such that dysfunctional Integrase protein is produced to prevent a transcribed viral DNA molecule from integrating into a host cell genome.

43. The construct of claim 42, wherein the mutation in the 5' flanking region is made in at least one position selected from the group consisting of arginine 3, arginine 10, lysine 11 and lysine 14.

44. The construct of claim 43, wherein the at least one position are substituted with alanine.

45. A nucleic acid construct which encodes non-infectious HIV particles, the construct comprising:
  a) at least one mutation in the gag gene of a HIV genome of a HIV particle wherein the gag gene encodes the amino acid sequence of the nucleocapsid (NC) protein, wherein the mutation is made in the 5' Cys-His box in at least one position selected from the group consisting of lysine 20, histidine 23 and arginine 26, such that the mutation prevents viral RNA packaging; and
  b) at least one further mutation in the pol gene of said HIV genome selected from the group consisting of
    i) at least one mutation in the region of the pol gene that encodes the amino acid sequence in the finger domain (amino acid 1 to 84 of SEQ ID NO: 4) of the reverse transcriptase (RT) proton, such that a dysfunctional reverse transcriptase protein is produced to prevent viral RNA conversion to DNA and
    (ii) at least one mutation in the region of the pol gene that encodes the amino acid sequence of the catalytic (amino acids 51–212 of SEQ ID NO: 6) or multimerization domain (amino acids 1–50 of SEQ ED NO: 6) of the Integrase (In) protein, such that dysfunctional Integrase protein is produced to prevent a transcribed viral DNA molecule from integrating into a host cell genome.

46. The construct of claim 45, wherein the at least one position are substituted with alanine.

47. A nucleic acid construct which encodes non-infections HIV particles, the construct comprising:
  a) at least one mutation in the gag gene of a HIV genome of a HIV particle wherein the gag gene encodes the amino acid sequence of the nucleocapsid (NC) protein, wherein the mutation is made in the peptide linker region (amino acids 29–35 of SEQ ID NO: 8), such that the mutation prevents viral RNA packaging; and b) at least one further mutation in the pol gene of said HIV genome selected from the group consisting of
  (i) at least one mutation in the region of the pol gene that encodes the amino acid sequence in the finger domain (amino acid 1 to 84 of SEQ ID NO: 4) of the reverse transcriptase (RT) protein, such that a dysfunctional reverse transcriptase protein is produced to prevent viral RNA conversion to DNA and
  (ii) at least one mutation in the region of the pol gene that encodes the amino acid sequence of the catalytic (amino acids 51–212 of SEQ ID NO: 6) or multimerization domain (amino acids 1–50 of SEQ ID NO: 6) of the Integrase (In) protein, such that dysfunctional Integrase protein is produced to prevent a transcribed viral DNA molecule from integrating into a host cell genome.

48. The construct of claim 47, wherein the mutation in the peptide linker region is made in at least one position selected from the group consisting of arginine 29, arginine 32, lysine 33 and lysine 34.

49. The construct of claim 48, wherein the at least one position are substituted with alanine.

50. A nucleic acid construct which encodes non-infectious HIV particles, the construct comprising:
a) at least one mutation in the gag gene of a HIV genome of a HIV particle wherein the gag gene encodes the amino acid sequence of the nucleocapsid (NC) protein, wherein the mutation is made in the 3' Cys-His box (amino acids 36–49 of SEQ ID NO: 8), such that the mutation prevents viral RNA packaging; and
b) at least one further mutation in the pol gene of said HIV genome selected from the group consisting of
  (i) at least one mutation in the region of the pol gene that encodes the amino acid sequence in the finger domain (amino acid 1 to 84 of SEQ ID NO: 4) of the reverse transcriptase (RT) protein, such that a dysfunctional reverse transcriptase protein is produced to prevent viral RNA conversion to DNA and
  (ii) at least one mutation in the region of the pol gene that encodes the amino acid sequence of the catalytic (amino acids 51–212 of SEQ ID NO: 6) or multimerization domain (amino acids 1–50 of SEQ ID NO: 6) of the Integrase (In) protein, such that dysfunctional Integrase protein is produced to prevent a transcribed viral DNA molecule from integrating into a host cell genome.

51. The construct of claim 50, wherein the mutation in the 3' Cys-His box is made in at least one position selected from the group consisting of lysine 38, lysine 41, histidine 44 and lysine 47.

52. The construct of claim 51, wherein the at least one position are substituted with alanine.

53. A nucleic acid construct which encodes non-infectious HIV particles, the construct comprising:
a) at least one mutation in the gag gene of a HIV genome of a HIV particle wherein the gag gene encodes the amino acid sequence of the nucleocapsid (NC) protein, wherein the mutation is made in the 3' flanking region (amino acids 50–55 of SEQ ID NO: 8), such that the mutation prevents viral RNA packaging; and
b) at least one further mutation in the pol gene of said HIV genome selected from the group consisting of
  (i) at least one mutation in the region of the pol gene that encodes the amino acid sequence in the finger domain (amino acid 1 to 84 of SEQ ID NO: 4) of the reverse transcriptase (RT) protein, such that a dysfunctional reverse transcriptase protein is produced to prevent viral RNA conversion to DNA and
  (ii) at least one mutation in the region of the pol gene that encodes the amino acid sequence of the catalytic (amino acids 51–212 of SEQ ID NO: 6) or multimerization domain (amino acids 1–50 of SEQ ED NO: 6) of the Integrase (In) protein, such that dysfunctional Integrase protein is produced to prevent a transcribed viral DNA molecule from integrating into a host cell genome.

54. The construct of claim 53, wherein the mutation in the 3' flanking region is made at position arginine 52.

55. The construct of claim 54, wherein the at least one position are substituted with alanine.

56. A nucleic acid construct which encodes non-infectious HIV particles, the construct comprising:
a) at least one mutation in the gag gene of a HIV genome of a HIV particle wherein the gag gene encodes the amino acid sequence of the nucleocapsid (NC) protein, wherein the mutation is made in at least one position selected from the group consisting of the 5' flanking region (amino acids 1–14 of SEQ ID NO: 8), the 5' Cys-His box (amino acids 15–28 of SEQ ID NO: 8), the peptide linker region (amino acids 29–35 of SEQ ID NO: 8), the 3' Cys-His box (amino acids 36–49 of SEQ ID NO: 8) and the 3' flanking region (amino acids 50–55 of SEQ ID NO: 8), such that the mutation prevents viral RNA packaging; and
b) at least one replacement mutation in the pol gene of said HIV genome selected from the group consisting of
  (i) at least one replacement mutation in the region of the pol gene that encodes the amino acid sequence in the finger domain (amino acid 1 to 84 of SEQ ID NO: 4) of the reverse transcriptase (RT) protein, wherein the replacement mutation in the RT protein produces a single amino acid substitution in at least one position selected from the group consisting of tryptophan 71, arginine 72 and arginine 78, and wherein the amino acid positions are substituted with alanine, such that a dysfunctional reverse transcriptase protein is produced to prevent viral RNA conversion to DNA and
  (ii) at least one replacement mutation in the region of the pol gene that encodes the amino acid sequence of the catalytic (amino acids 51–212 of SEQ ID NO: 6) or multimerization domain (amino acids 1–50 of SEQ ID NO: 6) of the Integrase (In) protein, wherein the replacement mutation produces a single amino acid substitution in the catalytic or multimerization domain such that dysfunctional Integrase protein is produced to prevent a transcribed viral DNA molecule from integrating into a host cell genome.

57. A nucleic acid construct which encodes non-infectious HIV particles, the construct comprising:
a) at least one mutation in the gag gene of a HIV genome of a HIV particle wherein the gag gene encodes the amino acid sequence of the nucleocapsid (NC) protein, wherein the mutation is made in at least one position selected from the group consisting of the 5' flanking region (amino acids 1–14 of SEQ ID NO: 8), the 5' Cys-His box (amino acids 15–28 of SEQ ID NO: 8), the peptide linker region (amino acids 29–35 of SEQ ID NO: 8), the 3' Cys-His box (amino acids 36–49 of SEQ ID NO: 8) and the 3' flanking region (amino acids 50–55 of SEQ ID NO: 8), such that the mutation prevents viral RNA packaging; and
b) at least one replacement mutation in the pol gene of said HIV genome selected from the group consisting of (i) at least one replacement mutation in the region of the pol gene that encodes the amino acid sequence in the finger domain (amino acid 1 to 84 of SEQ ID NO: 4) of the reverse transcriptase (RT) protein, wherein the replacement mutation produces a single amino acid substitution in the finger domain such that a dysfunctional reverse transcriptase protein is produced to prevent viral RNA conversion to DNA and (ii) at least one replacement mutation in the region of the pol gene that encodes the amino acid sequence of the catalytic domain (amino acids 51–212 of SEQ ID NO: 6) of the Integrase (In) protein, wherein the replacement mutation in the catalytic domain produces a single amino acid substitution in at least one position selected from the group consisting of aspartic acid 66, aspartic acid 118 and glutamic acid 154, and wherein the amino acid positions are substituted with alanine, such that dysfunctional Integrase protein is produced to prevent a transcribed viral DNA molecule from integrating into a host cell genome.

58. A nucleic acid construct which encodes non-infectious HIV particles, the construct comprising:

a) at least one mutation in the gag gene of a HIV genome of a HIV particle wherein the gag gene encodes the amino acid sequence of the nucleocapsid (NC) protein, wherein the mutation is made in at least one position selected from the group consisting of the 5' flanking region (amino acids 1–14 of SEQ ID NO: 8), the 5' Cys-His box (amino acids 15–28 of SEQ ID NO: 8), the peptide linker region (amino acids 29–35 of SEQ ID NO: 8), the 3' Cys-His box (amino acids 36–49 of SEQ ID NO: 8) and the 3' flanking region (amino acids 50–55 of SEQ ID NO: 8), such that the mutation prevents viral RNA packaging; and b) at least one replacement mutation in the pol gene of said HIV genome selected from the group consisting of (i) at least one replacement mutation in the region of the pol gene that encodes the amino acid sequence in the finger domain (amino acid 1 to 84 of SEQ ID NO: 4) of the reverse transcriptase (RT) protein, wherein the replacement mutation produces a single amino acid substitution in the finger domain such that a dysfunctional reverse transcriptase protein is produced to prevent viral RNA conversion to DNA and (ii) at least one replacement mutation in the region of the pol gene that encodes the amino acid sequence of the multimerization domain (amino acids 1–50 of SEQ ID NO: 6) of the Integrase (In) protein, wherein the replacement mutation in the multimerization domain produces a single amino acid substitution in at least one position selected from the group consisting of histidine 14, histidine 18, cysteine 42 and cysteine 45, and wherein the amino acid positions are substituted with alanine, such that dysfunctional Integrase protein is produced to prevent a transcribed viral DNA molecule from integrating into a host cell genome.

59. A nucleic acid construct which encodes non-infectious HIV particles, the construct comprising:

a) at least one mutation in the gag gene of a HIV genome of a HIV particle wherein the gag gene encodes the amino acid sequence of the nucleocapsid (NC) protein, wherein the mutation is made in at least one position selected from the group consisting of the 5' flanking region (amino acids 1–14 of SEQ ID NO: 8), the 5' Cys-His box (amino acids 15–28 of SEQ ID NO: 8), the peptide linker region (amino acids 29–35 of SEQ ID NO: 8), the 3' Cys-His box (amino acids 36–49 of SEQ ID NO: 8) and the 3' flanking region (amino acids 50–55 of SEQ ID NO: 8), wherein the mutations in the NC protein are at positions lysine 14, lysine 20, arginine 26, arginine 29, arginine 32, lysine 33, lysine 34, lysine 38, lysine 41 and lysine 47, such that the mutations prevents viral RNA packaging; and b) at least one further mutation in the pol gene of said HIV genome selected from the group consisting of (i) at least one mutation in the region of the pol gene that encodes the amino acid sequence in the finger domain (amino acid 1 to 84 of SEQ ID NO: 4) of the reverse transcriptase (RT) protein, wherein the mutations in the RT protein are at positions tryptophan 71, arginine 72 and arginine 78, such that a dysfunctional RT protein is produced to prevent viral RNA conversion to DNA and (ii) at least one mutation in the region of the pol gene that encodes the amino acid sequence of the catalytic (amino acids 51–212 of SEQ ID NO: 6) or multimerization domain (amino acids 1–50 of SEQ ID NO: 6) of the Integrase (In) protein, wherein the mutations in the In protein at positions histidine 14, histidine 18, cysteine 42, cysteine 45, aspartic acid 66, aspartic acid 118 and glutamic acid 154, such that dysfunctional In protein is produced to prevent a transcribed viral DNA molecule from integrating into a host cell genome.

60. The construct of claim 58, wherein the at least one position are substituted with alanine.

61. The nucleic acid construct of claim 1, wherein the construct further comprises a cytomegalovirus (CMV) promoter replacing a HIV 5' long terminal repeat (LTR) sequence.

62. The construct of claim 61, wherein the cytomegalovirus (CMV) promoter replaces the HIV 5' long terminal repeat (LTR) sequence from nucleotide 1 to nucleotide 636 of SEQ ID NO: 1.

63. An immunogenic composition to reduce viral load comprising the nucleic acid construct of claim 59.

* * * * *